US008691793B2

(12) United States Patent
Prestwich et al.

(10) Patent No.: US 8,691,793 B2
(45) Date of Patent: Apr. 8, 2014

(54) MODIFIED MACROMOLECULES AND ASSOCIATED METHODS OF SYNTHESIS AND USE

(75) Inventors: Glenn D. Prestwich, Salt Lake City, UT (US); Xiao Zheng Shu, Salt Lake City, UT (US); Yanchun Liu, Franklin, TN (US)

(73) Assignee: University of Utah Research Foundation, Salt Lake City, UT (US)

( * ) Notice: Subject to any disclaimer, the term of this patent is extended or adjusted under 35 U.S.C. 154(b) by 84 days.

(21) Appl. No.: 13/184,401

(22) Filed: Jul. 15, 2011

(65) Prior Publication Data

US 2012/0142907 A1 Jun. 7, 2012

Related U.S. Application Data

(63) Continuation of application No. 10/581,571, filed as application No. PCT/US2004/040726 on Dec. 6, 2004, now Pat. No. 7,981,871.

(60) Provisional application No. 60/526,797, filed on Dec. 4, 2003.

(51) Int. Cl.
*A01N 43/04* (2006.01)
*A61K 31/715* (2006.01)
*A61K 31/727* (2006.01)
*C07H 5/04* (2006.01)
*C07H 5/06* (2006.01)
*C08B 37/00* (2006.01)
*C08B 37/10* (2006.01)

(52) U.S. Cl.
USPC ............ 514/54; 536/18.7; 536/21; 514/56

(58) Field of Classification Search
USPC .................. 514/54, 56; 536/18.7, 21
See application file for complete search history.

(56) References Cited

U.S. PATENT DOCUMENTS

| | | | |
|---|---|---|---|
| 5,135,919 A | 8/1992 | Folkman et al. |
| 5,290,807 A | 3/1994 | Folkman et al. |
| 5,463,022 A | 10/1995 | Inoue et al. |
| 5,504,074 A | 4/1996 | D'Amato et al. |
| 5,616,568 A | 4/1997 | Pouyani et al. |
| 5,639,725 A | 6/1997 | O'Reilly et al. |
| 5,652,347 A | 7/1997 | Pouyani et al. |
| 5,661,143 A | 8/1997 | D'Amato et al. |
| 5,698,586 A | 12/1997 | Kishimoto et al. |
| 5,733,876 A | 3/1998 | O'Reilly et al. |
| 5,792,845 A | 8/1998 | O'Reilly et al. |
| 5,854,205 A | 12/1998 | O'Reilly et al. |
| 5,854,221 A | 12/1998 | Cao et al. |
| 5,861,372 A | 1/1999 | Folkman et al. |
| 5,874,417 A | 2/1999 | Prestwich et al. |
| 5,880,270 A | 3/1999 | Berninger et al. |
| 5,885,795 A | 3/1999 | O'Reilly et al. |
| 5,892,069 A | 4/1999 | D'Amato et al. |
| 5,945,403 A | 8/1999 | Folkman et al. |
| 6,017,954 A | 1/2000 | Folkman et al. |
| 6,024,688 A | 2/2000 | Folkman et al. |
| 6,086,865 A | 7/2000 | Folkman et al. |
| 6,174,861 B1 | 1/2001 | O'Reilly et al. |
| 6,251,959 B1 | 6/2001 | Kawahara et al. |
| 6,387,978 B2 | 5/2002 | Ronan et al. |
| 6,521,223 B1 | 2/2003 | Calias et al. |
| 6,534,591 B2 | 3/2003 | Rhee et al. |
| 6,548,081 B2 | 4/2003 | Sadozai et al. |
| 6,551,610 B2 | 4/2003 | Shalaby et al. |
| 6,562,363 B1 | 5/2003 | Mantelle et al. |
| 6,617,450 B1 | 9/2003 | Stocker et al. |
| 6,630,457 B1 | 10/2003 | Aeschlimann et al. |
| 6,635,622 B2 | 10/2003 | Tomiyama et al. |
| 6,656,714 B2 | 12/2003 | Holmes et al. |
| 6,913,764 B2 * | 7/2005 | Vogt et al. ............ 424/423 |
| 2002/0183265 A1 | 12/2002 | Vogt et al. |
| 2003/0087877 A1 | 5/2003 | Calias et al. |
| 2004/0072338 A1 | 4/2004 | Tsuzuki et al. |
| 2004/0157328 A1 | 8/2004 | Tsuzuki et al. |

FOREIGN PATENT DOCUMENTS

| | | |
|---|---|---|
| EP | 0045665 B1 | 9/1985 |
| JP | 2004-033135 A | 2/2004 |
| JP | 2004-513071 A | 4/2004 |
| JP | 2004-141053 A | 5/2004 |
| WO | WO 01/93846 A2 | 12/2001 |
| WO | WO 02/06373 A1 | 1/2002 |
| WO | WO 02/090390 A1 | 11/2002 |
| WO | WO 03/053489 A2 | 7/2003 |
| WO | WO 2004/037164 A1 | 5/2004 |

OTHER PUBLICATIONS

Tokura, S., Nishi, N., Tsutsumi, A., Somorin, O. (1983) Studies on Chitin VIII. Some Properties of Water Soluble Chitin Derivatives. Polymer Journal, vol. 15, No. 6, p. 485-489.*
Gunstone, F. (1996) Fatty Acid and Lipid Chemistry, p. 49-53.*
Almquist et al., "Synthesis and biological activity of a ketomethylene analogue of a tripeptide inhibitor of angiotensin converting enzyme", Journal of Medicinal Chemistry, vol. 23, pp. 1392-1398 (1980).
Benner, "Expanding the genetic lexicon: incorporating non-standard amino acids into proteins by ribosome-based synthesis", Trends in Biotechnology, vol. 12, pp. 158-163 (1994).
Cahill et al., "Site-specific mutagenesis with unnatural amino acids", Trends in Biochemical Sciences, vol. 14, No, 10, pp. 400-403 (1989).
Cao et al., "Comparative study of the use of poly(glycolic acid), calcium alginate and pluronics in the engineering of autologous porcine cartilage", J. Biomaterials Sci. Polymer Edn., vol. 9, pp. 475-487 (1998).

(Continued)

*Primary Examiner* — Scarlett Goon
(74) *Attorney, Agent, or Firm* — Susan T. Evans; McDermott Will & Emery

(57) ABSTRACT

Described herein are compounds such as macromolecules that have been modified in order to facilitate crosslinking and methods of making and using thereof.

8 Claims, 49 Drawing Sheets

(56) References Cited

OTHER PUBLICATIONS

Chen and Abatangelo, "Functions of hyaluronan in wound repair", Wound Repair and Regeneration, vol. 7, pp. 79-89 (1999).
Creighton, "Postranslational covalent modifications of polypeptide chains", *Proteins: structure and molecular properties*, W.H. Freeman & Co., San Francisco, pp. 78-86 (1983).
Hann et al., "On the double bond isostere of the peptide bond: preparation of an enkephalin analogue", J.C.S. Perkin Trans, 1, The Royal Society of Chemistry, pp. 307-314 (1982).
Hennink and Van Nostrum, "Novel crosslinking methods to design hydrogels", Adv. Drug Del. Rev., vol. 54, pp. 13-36 (2002).
Holladay et al., "Synthesis of hydroxyethylene and ketomethylene dipeptide isosteres", Tetrahedron Letters, vol. 24, No. 41, pp. 4401-4404 (1983).
Houlihan et al., "The relative solution and interfacial hydrophoobicity of ethylene oxide-propylen oxide-ethylene oxide block copolymers", vol. 69, pp. 147-153 (1992).
Hruby, "Conformational restrictions of biologically active peptides via amino acid side chain groups", Life Sciences, vol. 31, No. 3, pp. 189-199 (1982).
Hudson et al., "Methionine enkephalin and isosteric analogues, I. Synthesis on a phenolic resin support", International Journal of Peptide and Protein Research, vol. 14, No. 3, pp. 177-185 (1979).
Ibba and Hennecke, "Towards engineering proteins by site-directed incorporation in vivo of non-natural amino acids", Biotechnology, vol. 12, No. 7, pp. 678-682 (1994).
Ibba, "Strategies for in vitro and in vivo translation with non-natural amino acids", Biotechnology & Genetic Engineering Reviews, vol. 13, pp. 197-216 (1995).
Ishikawa et al., "Novel [2,3]-sigmatropic rearrangement for carbon—nitrogen bond formation", J. Am. Chem. Soc., vol. 123, No. 31, pp. 7734-7735 (2001).
Jaeger et al., "Predicting optimal and suboptimal secondary structure for RNA", Methods in Enzymology, vol. 183, pp. 281-306 (1989).
Jaeger et al., "Improved predictions of secondary structures for RNA", PNAS USA vol. 86, No. 20, pp. 7706-7710 (1989).
Jennings-White and Almquist, "Synthesis of ketomethylene analogs of dipeptides", Tetrahedron Letters, vol. 23, No. 25, pp. 2533-2534 (1982).
Jones et al., "Multivalent poly(ethylene glycol)-containing conjugates for in vivo antibody suppression", Bioconjugate Chem., vol. 14, No. 6, pp. 1067-1076 (2003).
Knudson and Knudson, "Cartilage proteoglycans", Seminars in Cell and Development Biology, vol. 12, pp. 69-78 (2001).
Letsinger et al., "Cholesteryl-conjugated oligonucleotides: synthesis, properties, and activity as inhibitors of replication of human immunodeficiency virus in cell culture", PNAS USA, vol. 86, No. 17, pp. 6553-6556 (1989).
Li et al., "Surface properties of poly(ethylene oxide)-containing copolymers on colloids", Polymeric Materials Science and Engineering, American Chemical Society, Washington D.C. pp. 62-75 (1993).
Li et al., "Synthesis and biological evaluation of a cross-linked hyaluronan-mitomycin C. hydrogel", Biomacromolecules, vol. 5, No. 3, pp. 895-902 (2004).
Li et al., "Chemical modification of surface active poly(ehtylene oxide)-poly (propylene oxide) triblock copolymers", Biocunjugate Chemistry, vol. 7, pp. 592-599 (1996).
Liu et al., "Crosslinked hyaluronan hydrogels containing mitomycin C reduce postoperative abdominal adhesions", Fertility and Sterility, vol. 83, No. 4, pp. 1275-1283 (2004).
Liu et al., "Disulfide crosslinked hyaluronan-gelatin sponge: growth of fibrous tissue in vivo", J. Biomed. Materials, vol. 68A, pp. 142-149 (2004).
Morley, "K+ channel openers and supression of airway hyperreactivity", Trends Pharm. Sci., vol. 15, No. 12, pp. 463-468 (1994).
Needleman and Wunsch, "A general method applicable to the search for similiarities in the amino acid sequence of two proteins", J. Mol. Biol., vol. 48, No. 3, pp. 443-453 (1970).
Neff et al., "A novel method for surface modification to promote cell attachment to hydrophobic substrates", J. Biomed. Mater. Res., vol. 40, No. 4, pp. 511-519 (1998).
Pearson and Lipman, "Improved tools for biological sequence camparison", PNAS USA, vol. 85, No. 8, pp. 2444-2448 (1988).
Prasad et al., "Surface activity and association of ABA polyoxyethlene-polyoxyproylene block copolymers in aqueous solution", J. Colloid Interface Science, vol. 69, No. 2, pp. 225-232 (1979).
Rizo and Gierasch, "Constrained peptides: models of bioactive peptides and protein substructures", Ann. Rev. Biochem., vol. 61, pp. 387-418 (1992).
Shu et al., "Attachment and spreading of fibroblasts on an RGD peptide-modified injectable hyaluran hydrogel", J. Biomed. Mater. Res., vol. 68A, vol. 365-375 (2004).
Shu et al., "Disulfide crosslinked hyaluronan hydrogels", Biomacromolecules, vol. 3, pp. 1304-1311 (2002).
Shu et al., "Disulfide crosslinked hyaluronan-gelatin hydrogel films: a covalent mimic of the extracellular matrix for in vitro cell growth", Biomaterials, vol. 24, pp. 3825-3834 (2003).
Shu et al., "In situ crosslinkable glycosaminoglycan hydrogels for tissue engineering", Biomaterials, vol. 25, pp. 1339-1348 (2004).
Smith and Waterman, "Comparison of Biosequences", Advances in applied mathematics, vol. 2, pp. 482-489 (1981).
Saptola, *Chemistry and Biochemistry of Amino Acids, Peptides, and Proteins*, Weinstein, ed., Marcel Dekker, New York, Chapter 5, pp. 267-319 (1983).
Saptola et al., "Structure-activity relationships of enkephalins containing serially replaced thiomethylene amide bond surrogates", Life Sciences, vol. 38, pp. 1243-1249 (1986).
Thorson et al., "A biosynthetic approach for the incorporation of unnatural amino acids into proteins", Methods in Molecular Biology, vol. 77, pp. 43-73 (1991).
Toole, "Hyaluronan in morphogenesis", Seminars in Cell & Developmental Biology, vol. 12, No. 79-87 (2001).
Toyokuni et al., "Synthesis of a new heterobifunctional linker, N-[-(aminooxy)butyl]maleimide, for facile access to a thiol-reactive 18F-labeling agent", Biocunjugate Chem., vol. 14, No. 6, pp. 1253-1259 (2003).
Webb et al., "A Novel Surfactent-based immobilization method for varying substrate-bound fibronectin", J. Biomed. Mater. Res., vol. 54, No. 4, pp. 509-518 (2001).
Zoller, "New Recombinant DNA methodology for protein engineering", Current Opinion in Biotechnology, vol. 3, No. 4, pp. 348-354 (1992).
Zuker, "On finding all suboptimal foldings of an RNA molecule" Science, vol. 244, No. 4900, pp. 48-52 (1989).
Mironov et al., "Bioprinting living structures", J. Materials Chemistry, vol. 17, pp. 2054-2060 (2007).

* cited by examiner step 1-2, Journal of Organic Chemistry, 55(9), 2580-6; 1990
step 3-4, Journal of the American Chemical Society, 123(31), 7734-7735; 2001

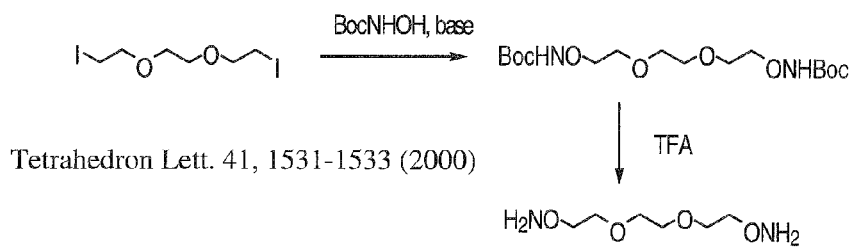
Tetrahedron Lett. 41, 1531-1533 (2000)
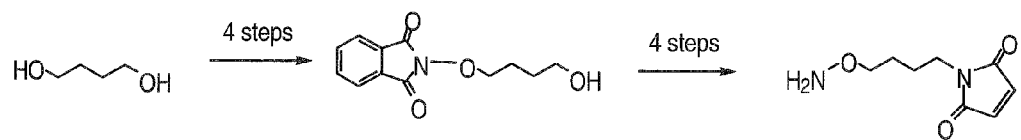
Bioconj. Chem. 14, 1253-1259 (2000)
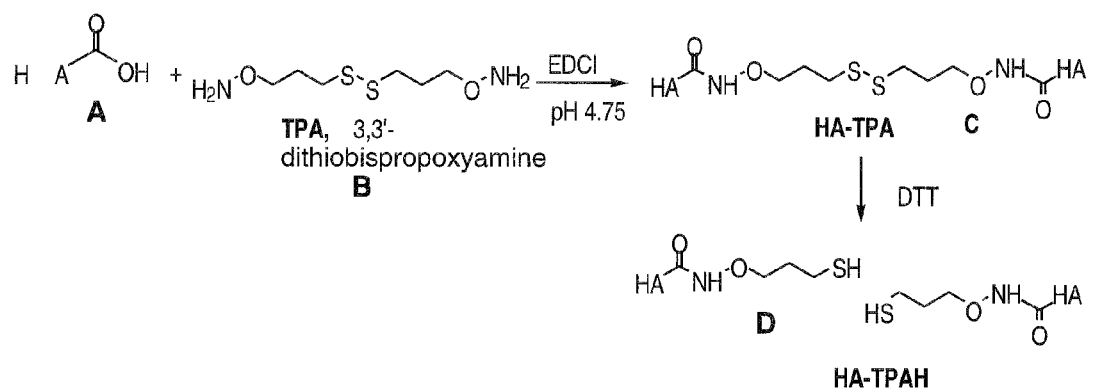
Fig. 2

Carbylan-S-X/Gelatin-DTPH behind the healed T.M.

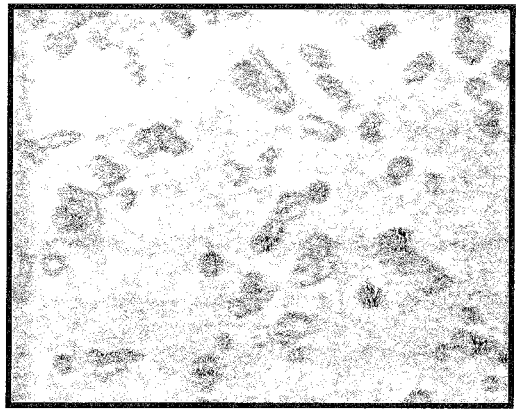 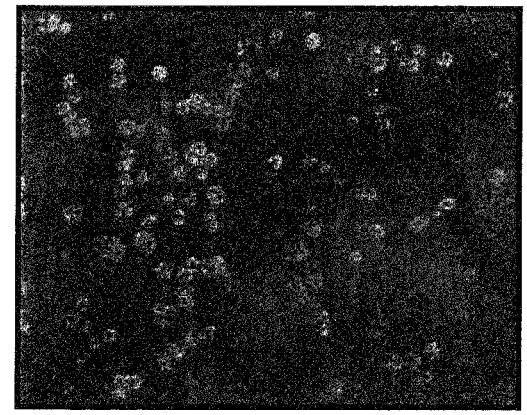
Day 1
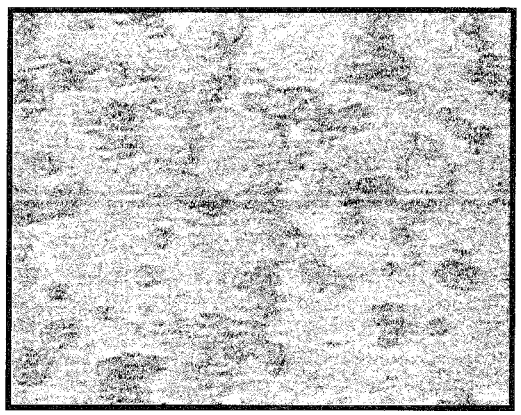 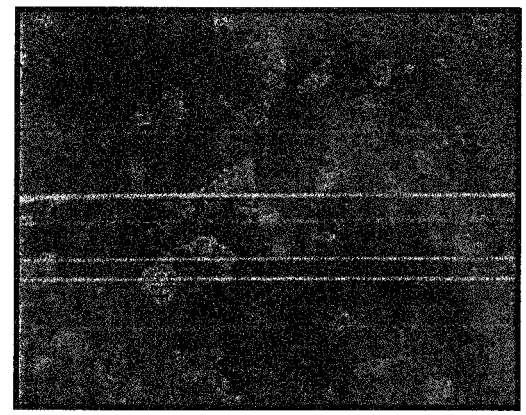
Day 2
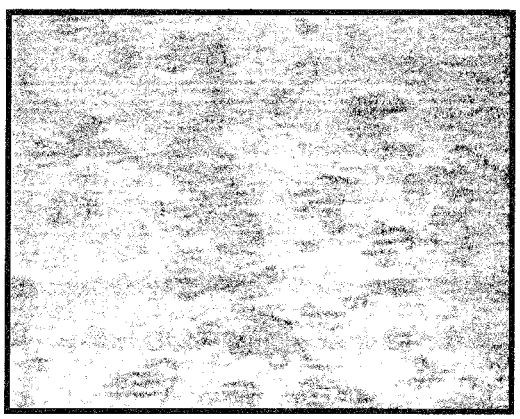 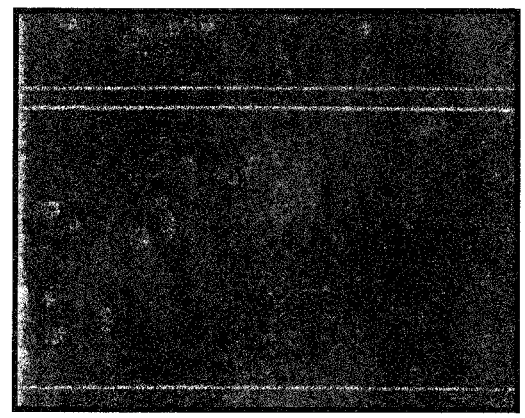
Day 3
Fig. 32

MODIFIED MACROMOLECULES AND ASSOCIATED METHODS OF SYNTHESIS AND USE

CROSS REFERENCE TO RELATED APPLICATIONS

This application is a continuation of U.S. application Ser. No. 10/581,571, filed Jun. 2, 2006 which issued on Jul. 19, 2011 as U.S. Pat. No. 7,981,871, which is a national stage filing, pursuant to 35 U.S.C. §371, of International Application No. PCT/US04/40726, filed Dec. 6, 2004, which claims priority upon U.S. provisional application Ser. No. 60/526,797, filed Dec. 4, 2003, all of which are hereby incorporated by reference in their entirety.

This invention was made with government support under Grant Nos. NIH 5R01 DC04663, R41 DC007015, and R41EB004226 awarded by the National Institutes of Health. The government has certain rights in the invention.

BACKGROUND

The use of macromolecules in pharmaceutical applications has received considerable attention. At times, it is desirable to couple two or more macromolecules to produce new macromolecule scaffolds with multiple activities. Existing technologies used to couple two or macromolecules, however, present numerous difficulties. For example, the alkaline conditions or high temperatures necessary to create hydrogels with high mechanical strength are cumbersome and harsh. Although the use of crosslinkers to produce macromolecular scaffolds has met with some success, the crosslinking agents are often relatively small, cytotoxic molecules, and the resulting scaffold has to be extracted or washed extensively to remove traces of unreacted reagents and byproducts (Hennink, W. E.; van Nostrum, C. F. *Adv. Drug Del. Rev.* 2002, 54, 13-36), thus precluding use in many medical applications. A physiologically compatible macromolecular scaffold capable of being produced in a straightforward manner is needed before they will be useful as therapeutic aids. Described herein are compounds and methods that are capable of coupling two or more molecules, such as macromolecules, under mild conditions.

SUMMARY

Described herein are compounds such as macromolecules that have been modified in order to facilitate crosslinking. In one aspect, the macromolecule is modified via an alkoxyamination reaction, wherein the resultant alkoxyaminated macromolecule can undergo crosslinking with itself or another macromolecule. In another aspect, the macromolecule is modified with a group capable of reacting with a hydrazide compound, which will facilitate crosslinking. Also described herein are methods of making and using the modified macromolecules.

The advantages described herein will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 2 shows a reaction scheme for producing aminooxy ether compounds and thiolated aminooxy-modified hyaluronan.

FIG. 32 shows a hepatocyte culture on a polystyrene plate in L15 medium.

DETAILED DESCRIPTION

Figure 1:
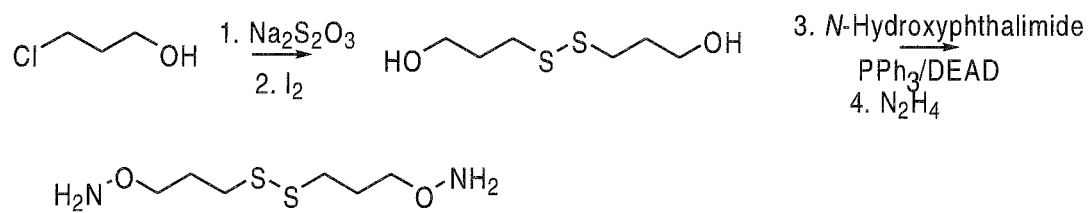
FIG. 1 shows a reaction scheme for producing a bis(aminooxy)ether compound.

Before the present compounds, composites, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A "residue" of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, a polymer having the repeat unit A-B, where one of the B units is modified with C, the resultant polymer can be represented by the formula D-C, where D is the remainder (i.e., residue) of the polymer A-B.

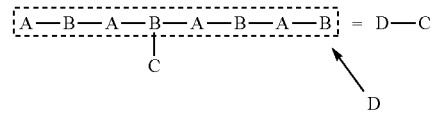

A fragment, as used in the specification and concluding claims, refers to a portion or section of a macromolecule or the entire macromolecule. For example, a polymer having the repeat unit A-B is depicted below, where one of the B repeat units is modified with C. The B-C unit is fragment E of the polymer composed of the repeat unit A-B as depicted below.

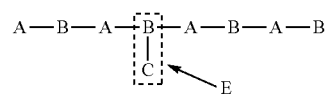

Variables such as $R^1$-$R^5$, $R^7$, $R^8$, $R^{20}$, $R^{25}$-$R^{30}$, n, n', LG, A E, L, J, G, M, Q, U, V, W, X, X', X", Y, and Z used throughout the application are the same variables as previously defined unless stated to the contrary.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "polyalkylene group" as used herein is a group having two or more $CH_2$ groups linked to one another. The polyalkylene group can be represented by the formula —$(CH_2)_n$—, where n is an integer of from 2 to 25.

The term "polyether group" as used herein is a group having the formula —$[(CHR)_nO]_m$—, where R is hydrogen or a lower alkyl group, n is an integer of from 1 to 20, and m is an integer of from 1 to 100. Examples of polyether groups include, polyethylene oxide, polypropylene oxide, and polybutylene oxide.

The term "polythioether group" as used herein is a group having the formula —$[(CHR)_nS]_m$—, where R is hydrogen or a lower alkyl group, n is an integer of from 1 to 20, and m is an integer of from 1 to 100.

The term "polyimino group" as used herein is a group having the formula —$[(CHR)_nNR]_m$—, where each R is, independently, hydrogen or a lower alkyl group, n is an integer of from 1 to 20, and m is an integer of from 1 to 100.

The term "polyester group" as used herein is a group that is produced by the reaction between a compound having at least two carboxylic acid groups with a compound having at least two hydroxyl groups.

The term "polyamide group" as used herein is a group that is produced by the reaction between a compound having at least two carboxylic acid groups with a compound having at least two unsubstituted or monosubstituted amino groups.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "hydrocarbyl group" as used herein means the monovalent moiety obtained upon removal of a hydrogen atom from a parent hydrocarbon. Representative of hydrocarbyl are alkyl of 1 to 20 carbon atoms, inclusive, such as methyl, ethyl, propyl, butyl, pentyl, hexyl, heptyl, octyl, nonyl, undecyl, decyl, dodecyl, octadecyl, nonodecyl, eicosyl, heneicosyl, docosyl, tricosyl, tetracosyl, pentacosyl and the isomeric forms thereof; aryl of 6 to 12 carbon atoms, inclusive, such as phenyl, tolyl, xylyl, naphthyl, biphenyl, tetraphenyl and the like; aralkyl of 7 to 12 carbon atoms, inclusive, such as benzyl, phenethyl, phenpropyl, phenbutyl, phenhexyl, napthoctyl and the like; cycloalkyl of 3 to 8 carbon atoms, inclusive, such as cyclopropyl, cyclobutyl, cyclopentyl, cyclohexyl, cycloheptyl, cyclooctyl and the like; alkenyl of 2 to 10 carbon atoms, inclusive, such as vinyl, allyl, butenyl, pentenyl, hexenyl, octenyl, nonenyl, decenyl, undecenyl, dodecenyl, tridecenyl, pentadecenyl, octadecenyl, pentacosynyl and isomeric forms thereof. Preferably, the hydrocarbyl group has 1 to 20 carbon atoms, inclusive.

The term "substituted hydrocarbyl and heterocarbyl" as used herein means the hydrocarbyl or heterocarbyl moiety as previously defined wherein one or more hydrogen atoms have been replaced with a chemical group, which does not adversely affect the desired preparation of the modified polysaccharide. Representative of such groups are amino, phosphino, quaternary nitrogen (ammonium), quaternary phosphorous (phosphonium), hydroxyl, amide, alkoxy, mercapto, nitro, alkyl, halo, sulfone, sulfoxide, phosphate, phosphite, carboxylate, carbamate groups and the like.

The term "hydrazide compound" as used herein is any compound having at least one hydrazide group having the formula $NH_2NRC(O)$—, wherein R can be hydrogen, a lower alkyl group, an amide group, a carbamate group, a hydroxyl group, or a halogen group.

The term "hydrazide-reactive group" as used herein is any group that can react with the primary or secondary amino group of the hydrazide group to form a new covalent bond. Examples of hydrazide-reactive groups include, but are not limited to, a ketone, an aldehyde, or an activated carboxylate group.

The term "aminooxy ether compound" as used herein is any compound having the formula RONHR', wherein R can be substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof and R' can be hydrogen or a lower alkyl group. The —ONHR' group is referred to herein as an aminooxy group.

The term "aminooxy-reactive group" as used herein is any group that can react with the amino group of the aminooxy group to form a new covalent bond. Examples of aminooxy-reactive groups include, but are not limited to, a ketone, an aldehyde, or an activated carboxylate group.

A. Materials

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Any of the compounds, compositions, and composites described herein can be the pharmaceutically acceptable salt or ester thereof if they possess groups that are capable of being converted to a salt or ester. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like.

In another aspect, if the compound possesses a basic group, it can be protonated with an acid such as, for example, HCl or $H_2SO_4$, to produce the cationic salt. In one aspect, the compound can be protonated with tartaric acid to produce the tartarate salt. In one aspect, the reaction of the compound with the acid or base is conducted in water, alone or in combination with an inert, water-miscible organic solvent, at a temperature of from about 0° C. to about 100° C. such as at room temperature. In certain aspects where applicable, the molar ratio of the compounds described herein to base used are chosen to provide the ratio desired for any particular salts. For preparing, for example, the ammonium salts of the free acid starting material, the starting material can be treated with approximately one equivalent of pharmaceutically-acceptable base to yield a salt.

Ester derivatives are typically prepared as precursors to the acid form of the compounds and accordingly can serve as prodrugs. Generally, these derivatives will be lower alkyl esters such as methyl, ethyl, and the like.

1. Macromolecules

A macromolecule as disclosed herein is any compound having at least one hydrazide-reactive group and/or aminooxy-reactive group. Examples of hydrazide-reactive groups and aminooxy-reactive groups include, but are not limited to, a carboxyl group including the salt or ester thereof or an amide group. The hydrazide-reactive group or the aminooxy-reactive group can be naturally present on the macromolecule, or the macromolecule can be chemically modified to incorporate the hydrazide-reactive group or the aminoalkoxy-reactive group on the macromolecule.

In one aspect, the macromolecule is an oligonucleotide, a nucleic acid or a metabolically stabilized analogue thereof, a polypeptide, a lipid, a glycoprotein, or a glycolipid. In another aspect, the macromolecule is a polysaccharide, a protein, or a synthetic polymer.

a) Oligonucleotides

The term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as modified oligonucleotides having non-naturally-occurring portions which function similarly. An oligonucleotide is a polymer of repeating units generically known as nucleotides or nucleosides. An unmodified (naturally occurring) nucleotide has three components: (1) a nitrogenous base linked by one of its nitrogen atoms to (2) a 5-carbon cyclic sugar and (3) a phosphate, esterified to carbon 5 of the sugar. When incorporated into an oligonucleotide chain, the phosphate of a first nucleotide is also esterified to carbon 3 of the sugar of a second, adjacent nucleotide. The "backbone" of an unmodified oligonucleotide consists of (2) and (3), that is, sugars linked together by phosphodiester linkages between the C5 (5') position of the sugar of a first nucleotide and the C3 (3') position of a second, adjacent nucleotide. Oligonucleotides can be composed of nucleoside or nucleotide sequences sufficient in identity and number to effect specific hybridization with a particular nucleic acid.

(1) Nucleic Acids

Nucleic acids such as deoxyribonucleic acid (DNA), ribonucleic acid (RNA), and peptide nucleic acid (PNA) are polymeric, polyionic molecules soluble in aqueous solution under certain conditions. The assumed three-dimensional structures of nucleic acids in solution as a function of pH, ionic strength, counter ions, charge neutralization, hydration, organic precipitants, molecular composition, etc., are known by those skilled in the art. In one aspect, the nucleic acid can be single or double stranded DNA or RNA.

There are a variety of molecules disclosed herein that are nucleic acid based, including for example the nucleic acids as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U.

(2) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

Thus, nucleic acids are polymers made up of nucleotides, called bases generically. The nucleic acid molecules can be characterized by the number of bases that make up the nucleic acid. For example, in certain embodiments the nucleic acid analytes are at least 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 155, 160, 165, 170, 175, 180, 185, 190, 195, 200, 210, 220, 230, 240, 250, 260, 270, 280, 290, 295, 300, 320, 340, 360, 380, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3200, 3400, 3600, 3800, 4000, 4500, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 50000, 100000, 200000, 300000, 400000, 500000, and 1000000 bases or base pairs long. In another aspect, the DNA or RNA has at least about 1,500 bases or base pairs.

b) Pharmaceutically-Acceptable Compound

In one aspect, the macromolecule can be a pharmaceutically-acceptable compound. Any of the biologically active compounds disclosed in U.S. Pat. No. 6,562,363 B1, which is incorporated by reference in its entirety, can be used as a pharmaceutically-acceptable compound. In one aspect, the pharmaceutically-acceptable compound includes substances capable of preventing an infection systemically in the biological system or locally at the defect site, as for example, anti-inflammatory agents such as, but not limited to, pilocarpine, hydrocortisone, prednisolone, cortisone, diclofenac sodium, indomethacin, 6$\alpha$-methyl-prednisolone, corticosterone, dexamethasone, prednisone, and the like; antibacterial agents including, but not limited to, penicillin, cephalosporins, bacitracin, tetracycline, doxycycline, gentamycin, chloroquine, vidarabine, and the like; analgesic agents including, but not limited to, salicylic acid, acetaminophen, ibuprofen, naproxen, piroxicam, flurbiprofen, morphine, and the like; local anesthetics including, but not limited to, cocaine, lidocaine, benzocaine, and the like; immunogens (vaccines) for stimulating antibodies against hepatitis, influenza, measles, rubella, tetanus, polio, rabies, and the like; peptides including, but not limited to, leuprolide acetate (an LH-RH agonist), nafarelin, and the like. All compounds are available from Sigma Chemical Co. (Milwaukee, Wis.).

In another aspect, the pharmaceutically-acceptable compound can be a substance or metabolic precursor which is capable of promoting growth and survival of cells and tissues or augmenting the functioning of cells is useful, as for example, a nerve growth promoting substance such as a ganglioside, a nerve growth factor, and the like; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF), interleukin-1 (IL-1), vascular endothelial growth factor (VEGF) and keratinocyte growth factor (KGF), dried bone material, and the like; and antineoplastic agents such as methotrexate, 5-fluorouracil, adriamycin, vinblastine, cisplatin, tumor-specific antibodies conjugated to toxins, tumor necrosis factor, and the like.

In another aspect, the pharmaceutically-acceptable compound can include hormones such as progesterone, testosterone, and follicle stimulating hormone (FSH) (birth control, fertility-enhancement), insulin, and the like; antihistamines such as diphenhydramine, and the like; cardiovascular agents such as papaverine, streptokinase and the like; anti-ulcer agents such as isopropamide iodide, and the like; bronchodilators such as metaproternal sulfate, aminophylline, and the like; vasodilators such as theophylline, niacin, minoxidil, and the like; central nervous system agents such as tranquilizer, B-adrenergic blocking agent, dopamine, and the like; antipsychotic agents such as risperidone, narcotic antagonists such as naltrexone, naloxone, buprenorphine; and other like substances. All compounds are available from Sigma Chemical Co. (Milwaukee, Wis.).

c) Lipids

In one aspect, neutral lipids can include, but are not limited to, synthetic or natural phospholipids. Typically, though not required, a neutral lipid has two hydrocarbon chains, e.g., acyl chains, and either a polar, nonpolar, or zwitterionic head group. The two hydrocarbon chains can be any length. In one aspect, the hydrocarbon chain is between about 14 to about 22 carbon atoms in length, and can have varying degrees of unsaturation. In another aspect, the neutral lipid has a high molecular weight and high melting temperature.

Neutral lipids that can be used in the methods and compositions described herein to create neutral liposomes include, but are not limited to, phosphatidylcholine (PC), phosphatidylethanolamine (PE), sphingomyelin (SPM), distearoylphosphatidylcholine (DSPC), dipalmitoylphosphatidylcholine (DPPC), dimyristoylphosphatidylcholine (DMPC), diarachidonoylphosphatidylcholine (DAPC), egg phosphatidylcholine, hydrogenated soy phosphatidylcholine (HSPC), glycosphingolipids and glycoglycerolipids, and sterols such as cholesterol, either alone or in combination with other lipids. In one aspect, the neutral lipid is distearoylphosphatidylcholine. Such neutral lipids can be obtained commercially or can be prepared by methods known to one of ordinary skill in the art.

Suitable anionic lipids include, but are not limited to, phospholipids that contain phosphatidylglycerol, phosphatidylserine or phosphatidic acid headgroups and two saturated fatty acid chains containing from about 14 to about 22 carbon atoms. Other suitable anionic lipids include, but are not limited to, phosphatidylserine (PS), phosphatidylglycerol (PG), phosphatidic acid (PA), phosphatidylinositol (PI), cardiolipin, dimyristoylphosphatidylglycerol (DMPG), and dipalmitoylphosphatidylglycerol (DPPG). In one aspect, the anionic lipid is dimyristoylphosphatidylglycerol. Such anionic lipids can be obtained commercially or can be prepared by methods known to one of ordinary skill in the art.

In one aspect, the lipid can be any phosphoinositide in which the inositol head group has zero, one, or two phosphates. In another aspect, the lipid can be a lysolipid including, but not limited to, lysophosphatidic acid (LPA), lysophosphatidylcholines (LPCs), and lysophosphatidylinositol (LPI). In another aspect, the lipid can be a sphingolipid including, but not limited to, sphingosine-1-phosphate (S1P) or sphingophatidylcholines (LPC). In another aspect, the lipid can be ceramide.

d) Polysaccharides

Any polysaccharide known in the art can be used herein. Examples of polysaccharides include starch, cellulose, glycogen or carboxylated polysaccharides such as alginic acid, pectin, or carboxymethylcellulose. In one aspect, the polysaccharide is a glycosaminoglycan (GAG). A GAG is one molecule with many alternating subunits. For example, HA is (GlcNAc-GlcUA-)x. Other GAGs are sulfated at different sugars. Generically, GAGs are represented by the formula A-B-A-B-A-B, where A is a uronic acid and B is an aminosugar that is either O- or N-sulfated, where the A and B units can be heterogeneous with respect to epimeric content or sulfation.

There are many different types of GAGs, having commonly understood structures, which, for example, are within the disclosed compositions, such as chondroitin, chondroitin sulfate, dermatan, dermatan sulfate, heparin, or heparan sulfate. Any GAG known in the art can be used in any of the methods described herein. Glycosaminoglycans can be purchased from Sigma, and many other biochemical suppliers. Alginic acid, pectin, and carboxymethylcellulose are among other carboxylic acid containing polysaccharides useful in the methods described herein.

In one aspect, the polysaccharide is hyaluronan (HA). HA is a non-sulfated GAG. Hyaluronan is a well known, naturally occurring, water soluble polysaccharide composed of two alternatively linked sugars, D-glucuronic acid and N-acetylglucosamine. The polymer is hydrophilic and highly viscous in aqueous solution at relatively low solute concentrations. It often occurs naturally as the sodium salt, sodium hyaluronate. Methods of preparing commercially available hyaluronan and salts thereof are well known. Hyaluronan can be purchased from Seikagaku Company, Clear Solutions Biotech, Inc., Pharmacia Inc., Sigma Inc., and many other suppliers. For high molecular weight hyaluronan it is often in the range of 100 to 10,000 disaccharide units. In another aspect, the lower limit of the molecular weight of the hyaluronan is from 1,000 Da, 2,000 Da, 3,000 Da, 4,000 Da, 5,000 Da, 6,000 Da, 7,000 Da, 8,000 Da, 9,000 Da, 10,000 Da, 20,000 Da, 30,000 Da, 40,000 Da, 50,000 Da, 60,000 Da, 70,000 Da, 80,000 Da, 90,000 Da, or 100,000 Da, and the upper limit is 200,000 Da, 300,000 Da, 400,000 Da, 500,000 Da, 600,000 Da, 700,000 Da, 800,000 Da, 900,000 Da, 1,000,000 Da, 2,000,000 Da, 4,000,000 Da, 6,000,000 Da, 8,000,000 Da, or 10,000,000 Da where any of the lower limits can be combined with any of the upper limits. In another aspect, Y in formula III is not hyaluronan.

(1) Modified-Glycosaminoglycans

In one aspect, any glycosaminoglycan in the art can be chemically modified so that at least one of the hydroxyl groups present on the glycosaminoglycan is substituted with a hydrazide-reactive group to produce a modified-glycosaminoglycan. Glycosaminoglycans in general possess a plurality of hydroxyl groups. The phrase "at least one of the hydroxyl groups present on the glycosaminoglycan is chemically substituted with a hydrazide-reactive group or aminooxy-reactive group" as used herein refers to replacing or substituting hydrogen of the hydroxyl group with the hydrazide-reactive group or the aminooxy-reactive group via a chemical manipulation of the hydroxyl group present on the glycosaminoglycan.

In one aspect, the modified-glycosaminoglycan is produced by (a) reacting a glycosaminoglycan with a base to produce deprotonated-glycosaminoglycan, and (b) reacting the deprotonated-glycosaminoglycan with a compound comprising at least one hydrazide-reactive group or aminooxy-reactive group. Not wishing to be bound by theory, it is believed that the base deprotonates at least one hydroxyl group to produce the corresponding alkoxide of the glycosaminoglycan. The alkoxide, which may be transient in nature, then reacts with the compound having at least one hydrazide-reactive group or aminooxy-reactive group to produce the modified-glycosaminoglycan. The deprotonated glycosaminoglycan may or may not react with the hydrazide-reactive group or the aminooxy-reactive group depending upon reaction conditions. Steps (a) and (b) can be performed stepwise, where the deprotonated glycosaminoglycan is isolated after step (a) followed by step (b) or, alternatively, steps (a) and (b) can be performed sequentially in situ.

Depending upon reaction conditions such as pH, reaction temperature, solvent, and base, any of the hydroxyl groups present on the glycosaminoglycan can be substituted with the hydrazide-reactive group or the aminooxy-reactive group. Additionally, the number of hydroxyl groups that are substituted with the hydrazide-reactive group or the aminooxy-reactive group will vary depending upon the reaction conditions. The reaction conditions for carrying out the synthesis of the modified-glycosaminoglycan are discussed below.

Any base known in the art can be used to produce the deprotonated glycosaminoglycan. Examples of bases useful herein include, but are not limited to, the base comprises a hydroxide, an alkoxide, a carbonate, an amine, phosphate, or an amide. In one aspect, sodium, potassium, or ammonium hydroxides, alkoxides, and carbonates can be used. Examples of amides useful in the present invention include, but are not limited to, potassium hexamethyldisilazide, sodium hexamethyldisilazide, lithium diisopropylamide, lithium hexamethyldisilazide, and lithium 2,2,6,6-tetramethylpiperidide. It is understood to one of ordinary skill in the art that non-aqueous solvents should be employed when the base is an amide. Examples of secondary amines include, but are not limited to, morpholine, diisopropylamine, pyrrolidine, 2,2,6,6-tetramethylpiperidine. Examples of tertiary amines include, but are not limited to, dimethyl ethyl amine, triethylamine, pyridine, diisopropylethylamine, collidine, or diazabicyclononane (DABCO).

The amount of base used to deprotonate the glycosaminoglycan will also vary depending upon the desired degree of substitution. In one aspect, when deprotonation is performed in an aqueous solution, an excess of base relative to the glycosaminoglycan is used in order to ensure sufficient deprotonation.

The synthesis of the modified-glycosaminoglycan is generally conducted in the presence of a solvent. Water, an organic solvent, or a combination thereof can be used as the reaction solvent. In one aspect, the organic solvent can be an alcohol, an ether, or a halogenated solvent. Examples of organic solvents useful in the present invention include, but are not limited to, dichloromethane, dimethylformamide, dimethylsulfoxide, dioxane, N-methylmorpholine, sulfolane, N-methylpyrrolidone, tetrahydrofuran, diethyl ether, toluene, dimethoxyethane, t-butyl methyl ether, or a mixture thereof.

Reaction temperatures and times can vary when adding the base to the glycosaminoglycan. In one aspect, the base is added to the glycosaminoglycan from −50° C. to 80° C. In another aspect, the lower limit of the reaction temperature is −45° C., −40° C., −35° C., −30° C., −25° C., −20° C., or −15° C., and the upper limit is −5° C., −10° C., −15° C., −20° C., −25° C., 0° C., 20° C., 40° C., or 60° C., where any lower temperature limit can be combined with any upper temperature limit. The base is allowed to react with glycosaminoglycan at from 30 seconds to 100 hours. In another, the lower time limit can be 1, 5, 10, 15 minutes, and the upper limit can be 100 hours, 90 hours, 80 hours, 70 hours, 60 hours, 50 hours, 40 hours, 30 hours, 20 hours, 10 hours, 5 hours, 2 hours, 1 hour, 30 minutes, 15 minutes, 10 minutes, or 5 minutes, where any lower time limit can be combined with any upper time limit.

After the deprotonated glycosaminoglycan is produced, a compound having at least one hydrazide-reactive group or aminooxy-reactive group is allowed to react with the deprotonated glycosaminoglycan. Any compound that possesses a hydrazide-reactive group and/or an aminooxy-reactive group that is capable of reacting with the deprotonated glycosaminoglycan can be used to produce the modified-glycosaminoglycan. In one aspect, the compound having at least one hydrazide-reactive group and/or an aminooxy-reactive group possesses a leaving group, wherein upon reaction with the deprotonated glycosaminoglycan, the bond between the leaving group and the compound is broken and a new bond is formed between the oxygen of the deprotonated glycosaminoglycan and the atom that was bonded to the leaving group, which is usually carbon. A leaving group is any group that is readily liberated from a compound when that compound is allowed to react with a nucleophile. Examples of leaving groups include, but are not limited to, a halogen such as fluoro, chloro, bromo, or iodo, a carbonate, ammonium group, or activated leaving groups such as tosylate, mesylate, phosphate, or triflate. The use of leaving groups for forming new bonds by nucleophilic substitution is widely known in the art. In another aspect, when the hydrazide-reactive group or the aminooxy-reactive group is an ester, the ester is can be activated with a leaving group including, but not limited to, an ammonium group, or a tosylate, mesylate, phosphate, or triflate, where the leaving group is bonded to the carbonyl carbon.

In one aspect, the compound having at least one hydrazide-reactive group or aminooxy group has the formula LG-L-G, wherein LG is a leaving group; L is a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof; and G is a hydrazide-reactive group or aminooxy-reactive group as defined above. In one aspect, LG can be a halogen. In another aspect, L can be a polyalkylene group having the formula $(CH_2)_n$, wherein n is 1, 2, 3, 4, 5, 6, 7, 8, 9, or 10. In another aspect, G can be $CO_2H$ or the salt or ester thereof. When the compound having the formula LG-L-G reacts with the deprotonated glycosaminoglycan, a covalent bond is formed between the deprotonated oxygen of the hydroxyl group and L and $LG^-$ is produced.

As described above, the selectivity and degree of substitution of the glycosaminoglycan will vary depending upon the reaction conditions selected. For example, depending upon the glycosaminoglycan selected, certain hydroxyl protons are more acidic than others. Thus by varying the pH (i.e., the amount and type of base) in the deprotonation step, it is possible to preferentially deprotonate one class of hydroxyl groups over another. In one aspect, a single hydroxyl group to 100% of the hydroxyl groups present on the glycosaminoglycan can be deprotonated and substituted.

In one aspect, the primary hydroxyl group of the glycosaminoglycan is chemically substituted with a hydrazide-reactive group or an aminooxy-reactive group. When the glycosaminoglycan is any compound other than hyaluronan, the primary hydroxyl group of the glycosaminoglycan is the C-6 hydroxyl group of the non-uronic acid sugar component of the repeating disaccharide of the glycosaminoglycan. All other hydroxyl groups present in the glycosaminoglycan are referred to herein as secondary hydroxyl groups.

In one aspect, when the glycosaminoglycan is hyaluronan, at least one primary hydroxyl group is chemically substituted with the hydrazide-reactive group or the aminooxy-reactive group. In the case of hyaluronan, the primary hydroxyl group is the C-6 hydroxyl group of the N-acetyl-glucosamine residue. All other hydroxyl groups present in hyaluronan that are not the primary hydroxyl group are referred to herein as the secondary hydroxyl group.

In one aspect, one primary hydroxyl group of the glycosaminoglycan to 100% of the primary hydroxyl groups can be substituted with the hydrazide-reactive group or aminooxy-reactive group. In one aspect, 0.1% to 40%, 0.1% to 30%, 0.1% to 20%, 0.1% to 10%, or 0.1% to 5% of the primary hydroxyl groups of hyaluronan can be substituted. In another aspect, 0.1%, 0.5%, 1%, 2%, 3%, 5%, 10%, 15%, 20%, 25%, or 30% of the primary hydroxyl groups to 40%, 45%, 50%, 55%, 60%, 65%, 70%, 75%, 80%, 85%, 90%, 95%, or 100% of the primary hydroxyl groups of hyaluronan can be substituted, where any lower endpoint can be combined with any upper endpoint. In another aspect, when one or more primary hydroxyl groups of the glycosaminoglycan are substituted, one or more secondary hydroxyl groups can also be substituted with the hydrazide-reactive group or the aminooxy-reactive group depending upon reaction conditions.

In one aspect, the modified-glycosaminoglycan can be hyaluronan with at least one primary hydroxyl group substituted with $CH_2CO_2H$ or the salt or ester thereof, wherein the $CH_2$ group is covalently bonded to oxide of the deprotonated glycosaminoglycan.

(2) Glycolipids and Glycoproteins

In one aspect, the macromolecule can be a glycolipid having at least one hydrazide-reactive group or aminooxy-reactive group. Examples of glycolipids include, but are not limited to, MGDG, diacylglucopyranosyl glycerols, and Lipid A. The glycolipids disclosed in U.S. Pat. No. 6,635,622, which is incorporated by reference in its entirety, can be used herein.

In another aspect, the macromolecule can be a glycoprotein having at least one hydrazide-reactive group or aminooxy-reactive group. Examples of glycolipids include, but are not limited to, orosomucoid alpha-1-acid glycoprotein (AAG) and alpha-1-glycoprotein. The glycolipids disclosed in U.S. Pat. Nos. 6,617,450 and 6,656,714, which are incorporated by reference in their entirety, can be used herein.

e) Synthetic Polymers

Any synthetic polymer known in the art can be used in the compositions and methods described herein. In one aspect, the synthetic polymer is glucuronic acid, polyacrylic acid, polyaspartic acid, polytartaric acid, polyglutamic acid, or polyfumaric acid.

f) Proteins

Any type of protein can be used in the compositions and methods described herein. For example, the protein can include peptides or fragments of proteins or peptides. The protein can be of any length, and can include one or more amino acids or variants thereof. The protein(s) can be fragmented, such as by protease digestion, prior to analysis.

Proteins useful in the methods described herein include, but are not limited to, an extracellular matrix protein, a chemically-modified extracellular matrix protein, or a partially hydrolyzed derivative of an extracellular matrix protein. The proteins may be naturally occurring or recombinant polypeptides possessing a cell interactive domain. The protein can also be mixtures of proteins, where one or more of the proteins are modified. Specific examples of proteins include, but are not limited to, collagen, elastin, decorin, laminin, or fibronectin.

(1) Protein Variants

As discussed herein there are numerous variants of proteins and that are known and herein contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
| --- | --- |
| alanine | Ala (A) |
| alloisoleucine | AIle |
| arginine | Arg (R) |
| asparagine | Asn (N) |
| aspartic acid | Asp (D) |
| cysteine | Cys (C) |
| glutamic acid | Glu (E) |
| glutamine | Gln (Q) |
| glycine | Gly (G) |
| histidine | His (H) |
| isolelucine | Ile (I) |
| leucine | Leu (L) |
| lysine | Lys (K) |
| phenylalanine | Phe (F) |
| proline | Pro (P) |
| pyroglutamic acid | Glu |
| serine | Ser (S) |
| threonine | Thr (T) |
| tyrosine | Tyr (Y) |
| tryptophan | Trp (W) |
| valine | Val (V) |

TABLE 2

Amino Acid Substitutions
Original Residue Exemplary Conservative
Substitutions, others are known in the art.

Ala ↔ ser
Arg ↔ lys or gln
Asn ↔ gln or his
Asp ↔ glu
Cys ↔ ser
Gln ↔ asn or lys
Glu ↔ asp
Gly ↔ pro
His ↔ asn or gln
Ile ↔ leu or val
Leu ↔ ile or val
Lys ↔ arg or gln;
Met ↔ Leu or ile
Phemet ↔ leu or tyr
Ser ↔ thr
Thr ↔ ser
Trp ↔ tyr
Tyr ↔ trp or phe
Val ↔ ile or leu Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W.H. Freeman & Co., San Francisco pp 79-86 (1983)), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH—(cis and trans), —$COCH_2$—, —CH(OH)$CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—CH(OH)$CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

2. Modification of Macromolecules

Described below are modifications of macromolecules using the methods and compositions described herein. The modifications generally involve the alkoxyamination of a macromolecule to produce an aminooxy-modified macromolecule, the hydrazide-modification of a macromolecule to produce a hydrazide-modified macromolecule, or a combination thereof. Any of the macromolecules described above, including the modified glycosaminoglycans, can be modified using the methods and compositions described below.

a) Alkoxyamination

Alkoxyamination involves reacting any of the macromolecules described above with a compound having at least one aminooxy group. A general reaction scheme that shows the reaction between a carboxylic acid group of macromolecule X, which is an aminooxy-reactive group, and an aminooxy ether compound is depicted in Scheme 1.

SCHEME 1

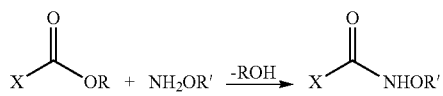

Figure 3:
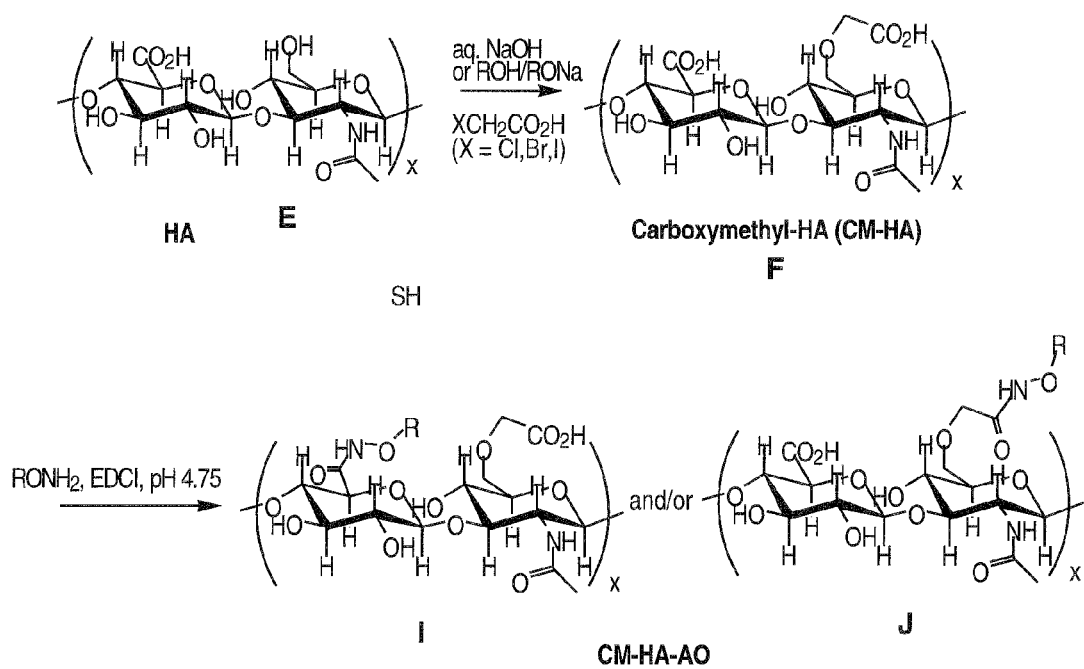
FIG. 3 shows a reaction scheme for producing aminooxy-modified hyaluronan.

The aminooxy group can react with any aminooxy-reactive group present on the macromolecule. Thus, in one aspect, the aminooxy group can react with a naturally-occurring aminooxy-reactive group present on the macromolecule. For example, hyaluronan has a plurality of COOH groups that can behave as aminooxy-reactive groups. In another aspect, when the macromolecule is any of the modified-glycosaminoglycans described above, the aminooxy group can react with the naturally-occurring aminooxy-reactive group present on the modified-glycosaminoglycan and/or the new aminooxy-reactive group that was chemically incorporated into the glycosaminoglycan. For example, in FIG. 3, compound F can be reacted with RONH$_2$ to produce compound I, where the aminooxy ether compound reacted with naturally-occurring COOH group of the glucuronic acid unit, and compound J, where the aminooxy ether compound reacted with the C-6 carboxymethyl group of the N-acetyl-glucosamine unit.

In one aspect, the aminooxy ether compound has the formula XXV

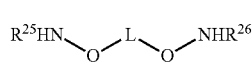

XXV where L can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof, and $R^{25}$ and $R^{26}$ can be, independently, hydrogen, alkyl, or aryl.

In one aspect, L can be a polyalkylene having a disulfide linkage (—S—S—). In another aspect, the aminooxy ether compound has the formula XXVI

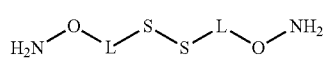

XXVI where each L can be, independently, a polyalkylene group or an aryl group. Reaction schemes for making an aminooxy ether compound useful in the methods and compositions described herein are depicted in FIGS. 1 and 2.

In one aspect, described herein are polymers comprising at least one —ONHR group covalently attached to the polymer, wherein R can be hydrogen, an alkyl group, or an aryl group as defined above. In one aspect, the polymer has one —ONHR group attached to the polymer. In another aspect, the polymer has two —ONHR groups attached to the polymer. In one aspect, the polymer has one —ONH$_2$ group attached to the polymer. In another aspect, the polymer has two —ONH$_2$ groups attached to the polymer. The polymer can be any compound having at least one hydroxyl group that can be converted to the corresponding —ONHR group. Examples of such polymers include, but are not limited to, polyethylene glycol (e.g., straight, branched, or a dendrimer), polypropylene oxide, or polyvinyl alcohol. Other molecules possessing at least one hydroxyl group can be derivatized with an aminooxy group. Examples of such molecules include, but are not limited to, a sugar, a saccharide (e.g., monosaccharide, oligosaccharide, or polysaccharide), a fatty alcohol, or a sterol.

In one aspect, the polymer is a triblock polymer of poly(ethylene oxide)-polypropylene oxide)-poly(ethylene oxide). These polymers are referred to as Pluronics®. Pluronics® are commercially available from BASF and have been used in numerous applications as emulsifiers and surfactants in foods, as well as gels and blockers of protein adsorption to hydrophobic surfaces in medical devices. These materials have low acute oral and dermal toxicity, and do not cause irritation to eyes or inflammation of internal tissues in man. The hydrophobic PPO block adsorbs to hydrophobic (e.g., polystyrene) surfaces, while the PEO blocks provide a hydrophilic coating that is protein-repellent. Pluronics® have low toxicity and are approved by the FDA for direct use in medical applications and as food additives. Surface treatments with Pluronics® can also reduce platelet adhesion, protein adsorption, and bacterial adhesion.

In one aspect, the polymer is a triblock polymer of poly(ethylene oxide)-polypropylene oxide)-poly(ethylene oxide), wherein the polymer has a molecular weight of from 1,000 Da to 100,000 Da. In another aspect, the polymer is a triblock polymer of poly(ethylene oxide)-poly(propylene oxide)-poly(ethylene oxide), wherein the polymer has a molecular weight of from having a lower endpoint of 1,000 Da, 2,000 Da, 3,000 Da, 5,000 Da, 10,000 Da, 15,000 Da, 20,000 Da, 30,000 and an upper endpoint of 5,000 Da, 10,000 Da, 15,000 Da, 20,000 Da, 25,000 Da, 30,000 Da, 40,000 Da, 50,000 Da, 60,000 Da, 70,000 Da, 80,000 Da, 90,000 Da, or 100,000 Da, wherein any lower endpoint can be matched with any upper endpoint, wherein the lower endpoint is less than the upper endpoint. In another aspect, the polymer is a triblock polymer of poly(ethylene oxide)-polypropylene oxide)-poly(ethylene oxide), wherein the polymer has a molecular weight of from 5,000 Da to 15,000 Da. In one aspect, the triblock polymer of poly(ethylene oxide)-poly(propylene oxide)-poly(ethylene oxide) is $PEO_{103}$-$PPO_{39}$-$PEO_{103}$, $PEO_{132}$-$PPO_{50}$-$PEO_{132}$, or $PEO_{100}$-$PPO_{65}$-$PEO_{100}$. In a further aspect, the polymer is $PEO_{103}$-$PPO_{39}$-$PEO_{103}$, $PEO_{132}$-$PPO_{50}$-$PEO_{132}$, or $PEO_{100}$-$PPO_{65}$-$PEO_{100}$, wherein the polymer has one or two —ONH$_2$ groups covalently bonded to it.

In the case when the polymer is a triblock polymer of poly(ethylene oxide)-polypropylene oxide)-poly(ethylene oxide), one or both of the terminal hydroxy groups can be converted to an aminooxy group. For example, the synthetic scheme depicted in FIG. 32 shows the synthesis of mono- and bis(aminooxy)poly(ethylene oxide)-polypropylene oxide)-poly(ethylene oxide) polymers. The reaction generally involves protecting one or both of the hydroxy groups (e.g., with N-hydroxyphthalimide) followed by deprotection (e.g., with hydrazine). In the case of the mono(aminooxy) polymer, the other hydroxyl group can be converted to a variety of groups (e.g., alkoxy) using techniques known in the art.

In one aspect, the reaction between the aminooxy ether compound and the macromolecule is carried out under mild conditions at a pH of about 0 to about 8, about 1 to about 7, or about 2 to about 6, or about 3 to about 5. In one aspect, the macromolecule is dissolved in water, which may also contain water-miscible solvents including, but not limited to, dimethylformamide, dimethylsulfoxide, and hydrocarbyl alcohols, diols, or glycerols.

The number of aminooxy groups present on the aminooxy-modified macromolecule will vary depending upon the amounts of aminooxy ether compound and macromolecule used. In one aspect, 1% to 99%, 10% to 90%, 20% to 80%, 30% to 70%, or 40% to 50% of the aminooxy-reactive groups present on the macromolecule are converted to the aminooxy group. In one aspect, at least one molar equivalent of aminooxy ether compound per molar equivalent of macromolecule is added. In other aspects, for maximum percentage functionalization, a large molar excess of the aminooxy ether compound (e.g., 10-100 fold) dissolved in water or aqueous-organic mixture is added and the pH of the reaction mixture is adjusted by the addition of dilute acid, e.g., HCl. In one aspect, a condensing agent can be used to facilitate the reaction between the macromolecule and the aminooxy ether compound. Examples of condensing agents useful herein include, but are not limited to, a water soluble carbodiimide such as 1-ethyl-3-[3-(dimethylamino)propyl]carbodiimide (EDCI). In another aspect, the condensing agent can be a hydroxybenzotriazole. In another aspect, an active ester forming agent such as N-hydroxysulfosuccinimide (sulfo-NHS) or N-hydroysuccinimide (NHS) can be used in combination with the condensing agent. The active ester forming agents disclosed in U.S. Pat. No. 6,630,457, which is incorporated by reference in its entirety, can be used herein. A sufficient molar excess (e.g., 2 to 100 fold) of carbodiimide reagent dissolved in water, in any aqueous-organic mixture, or finely-divided in solid form is then added to the reaction mixture.

In one aspect, after the macromolecule has reacted with the aminooxy ether compound, the resultant modified macromolecule has at least one fragment having the formula XVI

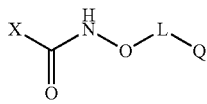

XVI wherein
X can be a residue of macromolecule;
Q can be a bioactive agent, an aminooxy group, a SH group, or a thiol-reactive electrophilic functional group; and
L can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof.

In formula XVI, X can be a residue of any of the macromolecules described herein. In one aspect, X is a residue of a modified-glycosaminoglycan described herein. In another aspect, L can be a polyalkylene group having the formula $(CH_2)_n$, wherein n is from 1 to 10, 1 to 8, 1 to 6, 1 to 4, 1 to 3, or 2.

In one aspect, Q in formula XVI can be a bioactive agent. The term "bioactive agent" as used herein is any therapeutic, prophylactic, pharmacological or physiological active substance, or mixture thereof, which is delivered to a subject to produce a desired, usually beneficial, effect. In one aspect, any active agent that is capable of producing a pharmacological response, localized or systemic, irrespective of whether therapeutic, diagnostic or prophylactic in nature, can be used as bioactive agents in any of the methods and compositions described herein. It should be noted that the bioactive agent can be used singularly or as a mixture of two or more agents.

Thus, it is possible to have two or more bioactive agents covalently attached to the macromolecule via the aminooxy ether compound. In one aspect, any of the macromolecules described above can be used as the bioactive agent. In another aspect, the bioactive agent can be a dye, a probe, a nucleic acid, an enzyme, an oligonucleotide, a label, a protein, a polypeptide, a lipid, a glycoprotein, a glycolipid, or a pharmaceutically-acceptable compound. In another aspect, any of the bioactive agents disclosed in U.S. Pat. No. 6,562,363 B1, which is incorporated by reference in its entirety, can be used herein.

In one aspect, the bioactive agent can be linked to the aminooxy ether compound via a linkage. Examples of linkages include, but are not limited to, ethers, imidates, thioimidates, esters, amides, thioethers, thioesters, thioamides, carbamates, ethers, disulfides, hydrazides, hydrazones, oxime ethers, oxime esters, and amines.

In another aspect, Q in formula XVI is a thiol-reactive electrophilic functional group. The term "thiol-reactive electrophilic group" as used herein is any group that is susceptible to nucleophilic attack by the lone-pair electrons on the sulfur atom of the thiol group or by the thiolate anion. Examples of thiol-reactive electrophilic groups include groups that have good leaving groups. For example, an alkyl group having a halide or alkoxy group attached to it or an α-halocarbonyl group are examples of thiol-reactive electrophilic groups.

In another aspect, the thiol-reactive electrophilic group is an electron-deficient vinyl group. The term "an electron-deficient vinyl group" as used herein is a group having a carbon-carbon double bond and an electron-withdrawing group attached to one of the carbon atoms. An electron-deficient vinyl group is depicted in the formula $C_\beta$=$C_\alpha X$, where X is the electron-withdrawing group. When the electron-withdrawing group is attached to $C\alpha$, the other carbon atom of the vinyl group ($C\beta$) is more susceptible to nucleophilic attack by the thiol group. This type of addition to an activated carbon-carbon double bond is referred to as a Michael addition. In another aspect, the thiol-reactive compound can be represented by the formula C=CW, where W is the thiol-reactive electrophilic functional group. In one aspect, W can be $OC(O)R^{20}$, wherein $R^{20}$ can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, or a combination thereof.

Examples of electron-withdrawing groups include, but are not limited to, a nitro group, a cyano group, an ester group, an aldehyde group, a keto group, a sulfone group, or an amide group. Examples of compounds possessing thiol-reactive electrophilic groups include, but are not limited to, maleimides, vinyl sulfones, acrylonitriles, α-methylene esters, quinone methides, acryloyl esters or amides, or α-halo esters or amides.

In another aspect, Q in formula XVI is an aminooxy group. In one aspect, a compound possessing two or more aminooxy groups, where one of the aminooxy groups does not react with an aminooxy-reactive group on the macromolecule, can result in a free aminooxy group Q. Depending upon the identity of L in formula XVI, it is possible to have two or more free or reacted aminooxy groups present in formula XVI. In one aspect, the modified macromolecule has at least one fragment having the formula II

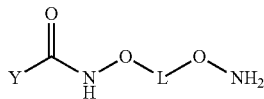

wherein Y is any modified glycosaminoglycan and linker, respectively, described herein.

In another aspect, Q in formula XVI can be SH. FIG. 2 depicts one aspect of the method described above for producing a compound having the formula XVI, where Q is SH. The first step involves reacting the macromolecule hyaluronan (A) having the formula HA-COOH with the aminooxy ether compound B to produce compound C. In one aspect, the reaction can be performed in the presence of a condensing agent. In one aspect, a condensing agent is any compound that facilitates the reaction between the aminooxy group of compound B and the COOH group on the macromolecule A. Any of the condensing agents described above can be used in this aspect. In one aspect, the condensing agent is a carbodiimide, including, but not limited to, 1-ethyl-3-[3-(dimethylamino)propyl]carbodiimide (EDCI). The disulfide bond in compound C can be cleaved with a reducing agent. In one aspect, the reducing agent is dithiothreitol. Cleavage of the disulfide bonds in compound C produces thiol compounds D, which fall under formula XVI. In one aspect, when Q is SH in formula XVI, L can be $CH_2$, $CH_2CH_2$, $CH_2CH_2CH_2$, or phenyl.

Figure 34:
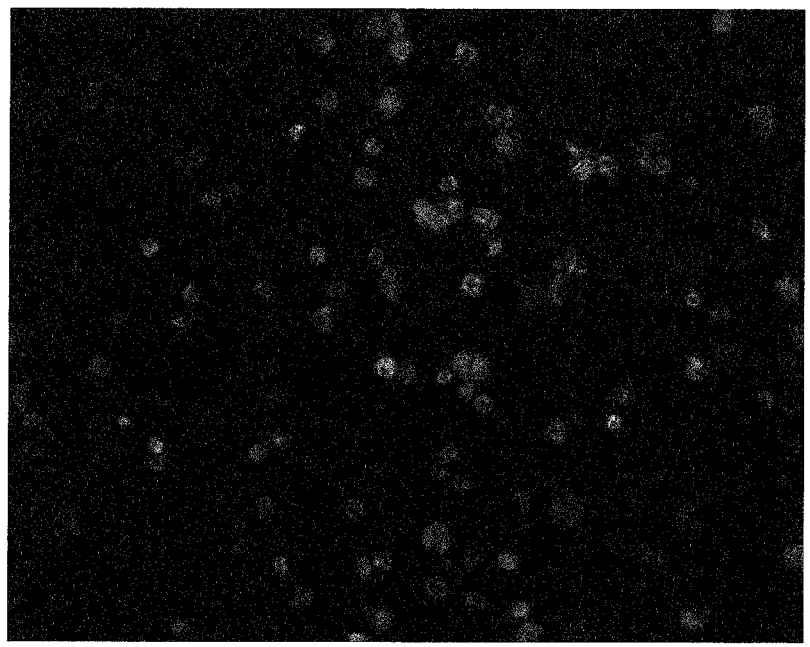
FIG. 34 shows a 3-D culture of hepatocytes in Carbylan™-GSX at day 3.
Figure 35:
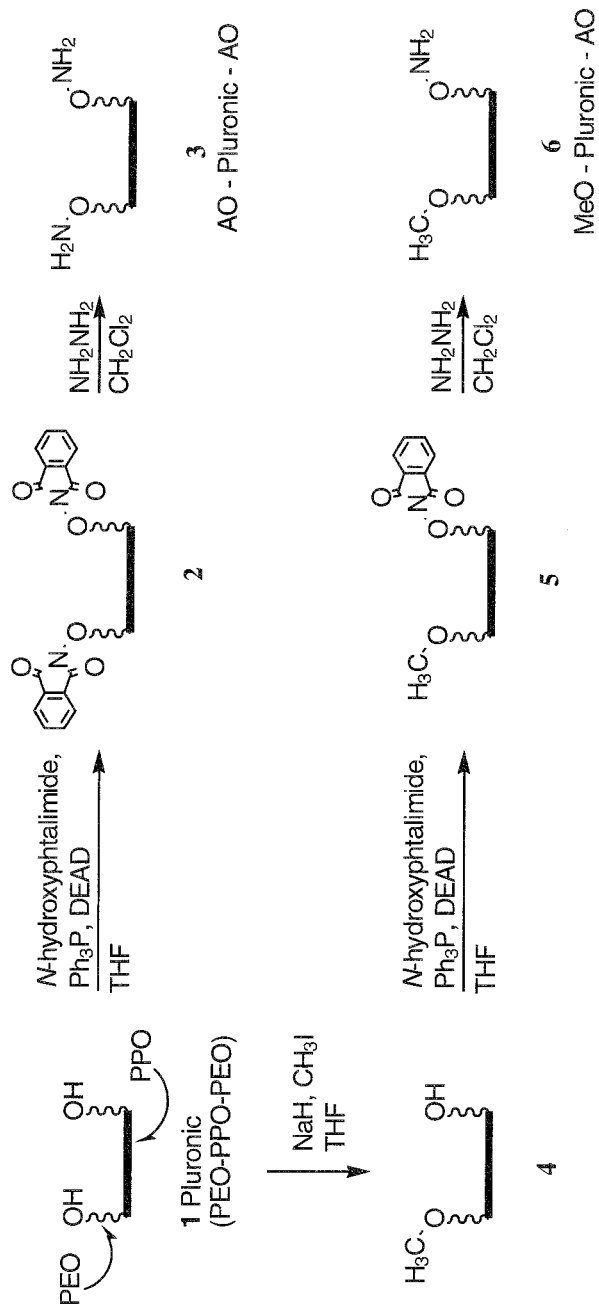
FIG. 35 shows reactions scheme for producing mono- and bisaminooxy pluronics.
Figure 37:
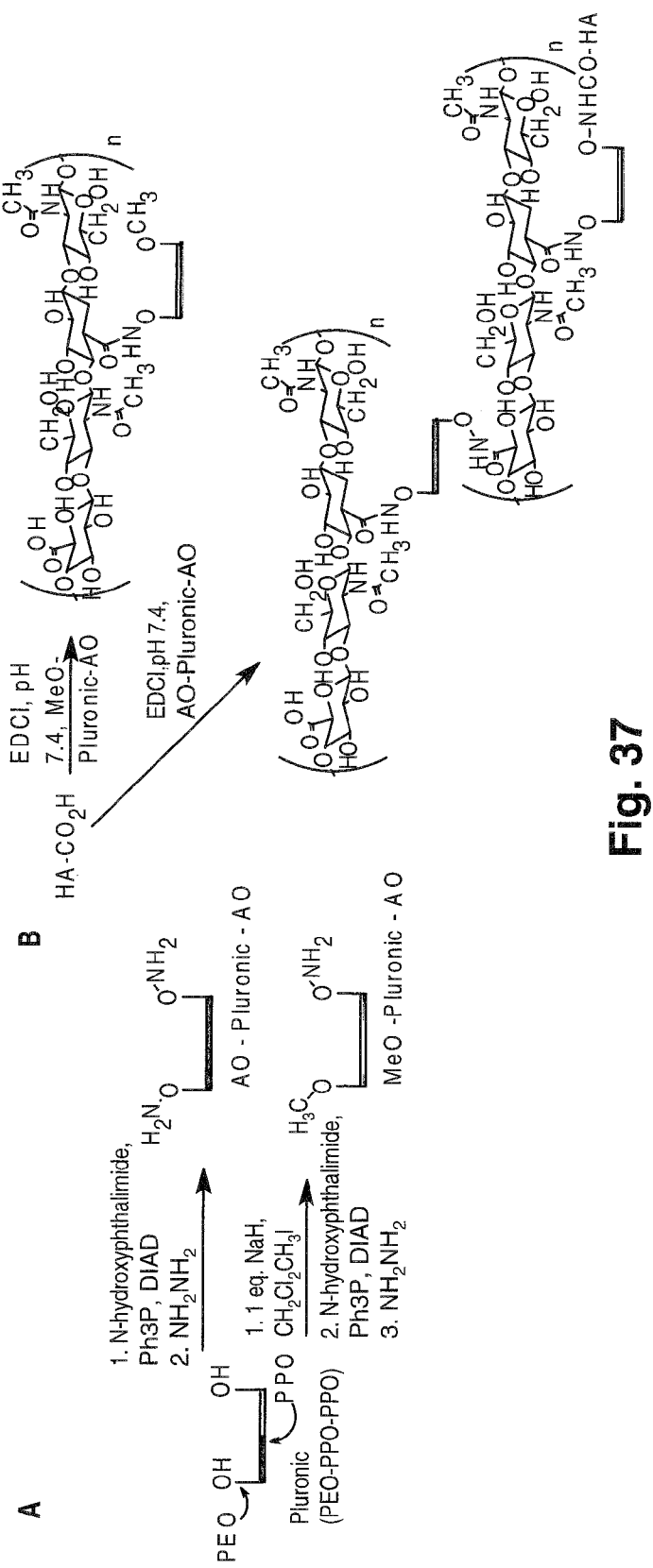
FIG. 37 shows a reaction scheme for coupling aminooxy polymers with hyaluronan.
Figure 38:
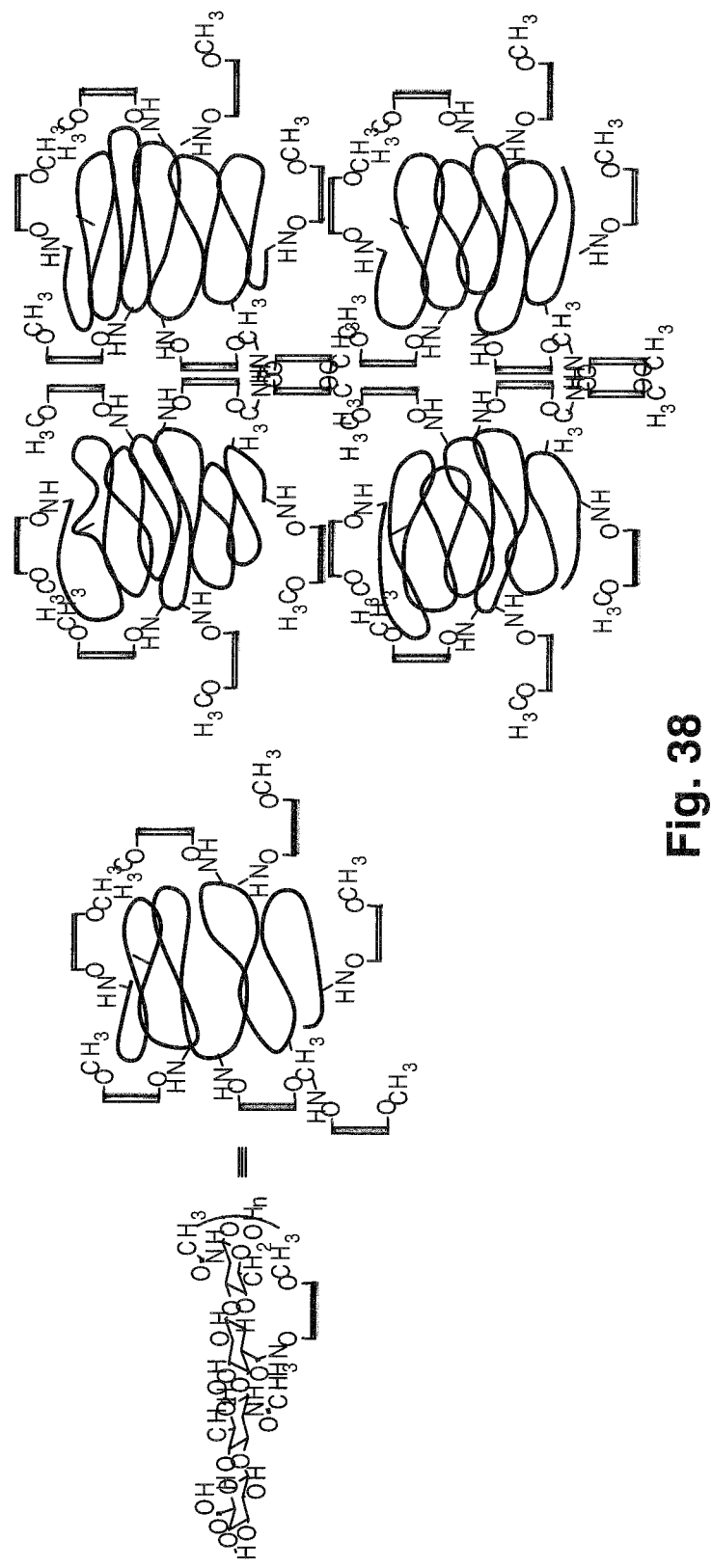
FIG. 38 shows a reaction scheme for the self-assembly of an aminooxy polymer/hyaluronan into a hydrogel.

In one aspect, it is contemplated the polymers comprising at least one aminooxy group can react with one or more macromolecules to produce a self-assembling extracellular matrix (ECM). Any of the macromolecules described herein can be used in this aspect. For example, the macromolecule can be chondroitin, chondroitin sulfate, dermatan, dermatan sulfate, heparin, heparan sulfate, alginic acid, pectin, or hyaluronan. In another aspect, the polymer is a triblock polymer of poly(ethylene oxide)-polypropylene oxide)-poly(ethylene oxide) comprising one or two —$ONH_2$ groups and the macromolecule is hyaluronan. FIGS. 34 and 35 depict one aspect of the self assembling ECM. In FIG. 37, mono- and bis(aminooxy) pluronics are coupled with hyaluronan to produce an aminooxy-modified biopolymer. In FIG. 35, the aminooxy-modified biopolymer can react with itself (i.e., self-assemble) or a different aminooxy-modified biopolymer to form a hydrogel. Not wishing to be bound by theory, it is believed that the hydrophobic PPO blocks of the pluronic can permit the organization and assembly of the aminooxy-modified biopolymer into hydrogels without the need for chemically-reactive crosslinkers.

b) Hydrazide-Modification

Hydrazide-modification of a macromolecule involves reacting any of the macromolecules described herein with a compound having at least one hydrazide group to produce a hydrazide-modified macromolecule. The mechanism is similar to that above in Scheme 1 for the reaction between the aminooxy ether compound and the macromolecule. Reaction scheme 2 that shows the reaction between a carboxylic acid of macromolecule X, which is a hydrazide-reactive group, and a hydrazide compound.

SCHEME 2

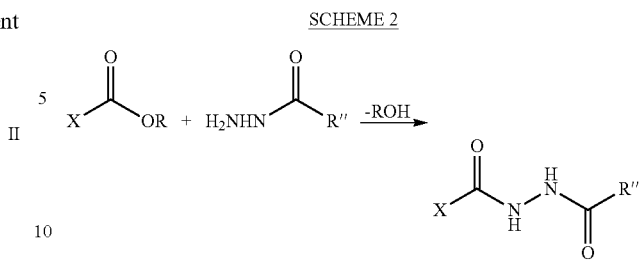

Similar to the aminooxy group, the hydrazide-group can react with any hydrazide-reactive group present on the macromolecule. Thus, in one aspect, the hydrazide group can react with a naturally-occurring hydrazide-reactive group present on the macromolecule. In another aspect, when the macromolecule is any of the modified-glycosaminoglycans described above, the hydrazide group can react with the naturally-occurring hydrazide-reactive group present on the modified-glycosaminoglycan and/or the new hydrazide-reactive group that was chemically incorporated into the glycosaminoglycan.

In one aspect, a hydrazide compound can be reacted with any of the modified-glycosaminoglycans described herein to produce a hydrazide-modified macromolecule. Any of the techniques and procedures disclosed in U.S. Pat. No. 5,874,417 for functionalizing hyaluronan with a hydrazide, which is incorporated by reference in its entirety, can be used to hydrazide-modify the any macromolecules described herein. For example, the modified-glycosaminoglycan can be reacted with a monohydrazide (i.e., a compound having only one hydrazide group) or a polyhydrazide (i.e., a compound having two or more hydrazide groups). Any of the hydrazide compounds disclosed in U.S. Pat. No. 5,874,417 can be used in this aspect.

In one aspect, dihydrazides can be used to modify any of the macromolecules herein. In one aspect, the dihydrazide has the formula 1:

$$H_2N-NH-CO-A-CO-NH-NH_2 \qquad (1)$$

wherein A is hydrocarbyl such as alkyl, aryl, alkylaryl or arylalkyl or A is heterohydrocarbyl, which also includes oxygen, sulfur, and/or nitrogen atoms in addition to carbon atoms. In this aspect, the alkyl group may be branched or unbranched and contain one to 20 carbons or other carbon-sized atoms, preferably 2 to 10, more preferably 4 to 8 carbons or carbon-sized heteroatoms, such as oxygen, sulfur or nitrogen. The alkyl group may be fully saturated or may contain one or more multiple bonds. The carbon atoms of the alkyl may be continuous or separated by one or more functional groups such as an oxygen atom, a keto group, an amino group, an oxycarbonyl group and the like. The alkyl group may be substituted with one or more aryl groups. The alkyl group may in whole or in part, be in form of rings such as cyclopentyl, cyclohexyl, and the like. Any of the alkyl groups described above may have double or triple bond(s).

Any of the hydrocarbyl groups can be used as a heterocarbyl group, wherein the alkyl or aryl group contains a heteroatom such as oxygen, sulfur, or nitrogen incorporated within the chain or ring. Moreover, any of the carbon atoms of the alkyl group may be separated from each other or from the dihydrazide moiety with one or more groups such as carbonyl, oxycarbonyl, amino, and also oxygen and sulfur atoms singly or in a configuration such as —S—S—, —O—$CH_2$—$CH_2$—O—, S—S—$CH_2$—$CH_2$— and NH($CH_2$)$_n$NH—, where n is from 1 to 20.

Aryl substituents are typically substituted or unsubstituted phenyl, but may also be any other aryl group such as pyrrolyl, furanyl, thiophenyl, pyridyl, thiazoyl, etc. An inorganic, alkyl or other aryl group including halo, hydroxy, amino, thioether, oxyether, nitro, carbonyl, etc may further substitute the aryl group.

The alkylaryl or arylalkyl groups may be a combination of alkyl and aryl groups as described above. These groups may be further substituted as described above.

In another aspect, the dihydrazide has the formula (2)

$$H_2N-NH-CO-NH-A-CO-NH-NH_2 \quad (2)$$

In this aspect, A in formula 2 can be hydrocarbyl, heterocarbyl, substituted hydrocarbyl substituted heterocarbyl and the like. In another aspect, A can be any of the linkers denoted and referred to as L throughout the application.

Generally, to obtain dihydrazides, two hydroxy groups of a dicarboxylic acid are substituted with $NH_2NH_2$ yielding the dihydrazide. Examples of dicarboxylic acids include, but are not limited to, maleic acid, fumaric acid, and aromatic dicarboxylic acids, such as terephthalic acid and isophthalic acid.

In one embodiment, aliphatic dihydrazides, where A is an alkyl group, may have the formula 3:

$$NH_2NHCO(CH_2)_n CONHNH_2 \quad (3)$$

wherein n' can be any length but is preferably from 1 to 20. Aliphatic dihydrazides useful in the invention include, but are not limited to, succinic (butandioic) (n'=2), adipic (hexanedioic) (n'=4), suberic (octanedioic) (n'=6), oxalic (ethanedioic) (n'=0), malonic (propanedioic) (n'=1), glutaric (pentanedioic) (n'=3), pimelic (heptanedioic) (n'=5), azelaic (nonanedioic) (n'=7), sebacic (decanedioic) (n'=8), dodecanedioic, (n'=10), brassylic (tridecanedioic), (n'=11), (etc. up to n'=20).

In one aspect, adipic dihydrazide, suberic dihydrazide, and butandioic dihydrazide are used to prepare the modified polysaccharide. Adipic dihydrazide can be purchased from Aldrich Chemical Co. (Milwaukee, Wis.). In another aspect, phthalic dihydrazide and dihydrazides with A containing oxa, thio, amino, disulfide ($-CH_2-S-S-CH_2-$), $-S(CH_2)_2S-$, $-O(CH_2)_nO-$ or $-NH(CH_2)_nNH-$ (n=2 to 4) groups.

In one aspect, the dihydrazides are at least partially soluble in water. The dihydrazides are also weak bases or weak acids having a $pK_a$ for the protonated form, less than about 8, preferably in the range of 1 to 7 and most preferably 2 to 6. It will be understood that the term $pK_a$ is used to express the extent of dissociation or the strength of weak acids, so that, for example, the $pK_a$ of the protonated amino group of amino acids is in the range of about 12-13 in contrast to the $pK_a$ of the protonated amino groups of the dihydrazides useful herein which is less than about 7.

As described above, the hydrazide compound reacts with a hydrazide-reactive group present on the macromolecule. In one aspect, the reaction is carried out under mild conditions at a pH of about 0 to about 8, about 1 to about 7, or about 2 to about 6, or about 3 to about 5. In one aspect, the macromolecule is dissolved in water, which may also contain water-miscible solvents including, but not limited to, dimethylformamide, dimethylsulfoxide, and hydrocarbyl alcohols, diols, or glycerols.

Similar to above for the aminooxy ether compounds, the number of hydrazide groups present on the modified macromolecule will vary depending upon the amounts of hydrazide compound and macromolecule used. In one aspect, 1% to 99%, 10% to 90%, 20% to 80%, 30% to 70%, or 40% to 50% of the hydrazide-reactive groups present on the macromolecule are converted to the hydrazide group. In one aspect, at least one molar equivalent of hydrazide compound per molar equivalent of macromolecule is added. In other aspects, for maximum percentage functionalization, a large molar excess of the hydrazide compound (e.g., 10-100 fold) dissolved in water or aqueous-organic mixture is added and the pH of the reaction mixture is adjusted by the addition of dilute acid, e.g., HCl. A sufficient molar excess (e.g., 2 to 100 fold) of carbodiimide reagent dissolved in water, in any aqueous-organic mixture, or finely-divided in solid form is then added to the reaction mixture.

In one aspect, the hydrazide-modified macromolecule has at least one fragment having the formula I

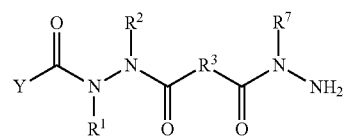

wherein Y can be a residue of any modified-glycosaminoglycan described herein and $R^1$, $R^2$, $R^3$, and $R^7$ can be, independently, hydrogen, a substituted or unsubstituted hydrocarbyl group, a substituted or unsubstituted heterohydrocarbyl group, or a polyether group, wherein $R^3$ is not hydrogen. In one aspect, $R^1$, $R^2$, and W are hydrogen. In another aspect, can be $R^3$ can be alkyl group such as $(CH_2)_n$, wherein n is from 1 to 20, 1 to 15, 1 to 10, 1 to 8, 1 to 6, or 2 to 4.

In one aspect, the hydrazide-modified macromolecule has at least one fragment having the formula III

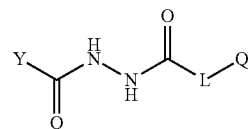

wherein Y can be a residue of any of the modified-glycosaminoglycan described herein; Q can be a residue of a bioactive agent, SH group or a thiol-reactive electrophilic functional group; and L can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof. Any of the bioactive agents and thiol-reactive electrophilic functional groups described above can be used in this aspect.

Figure 4:
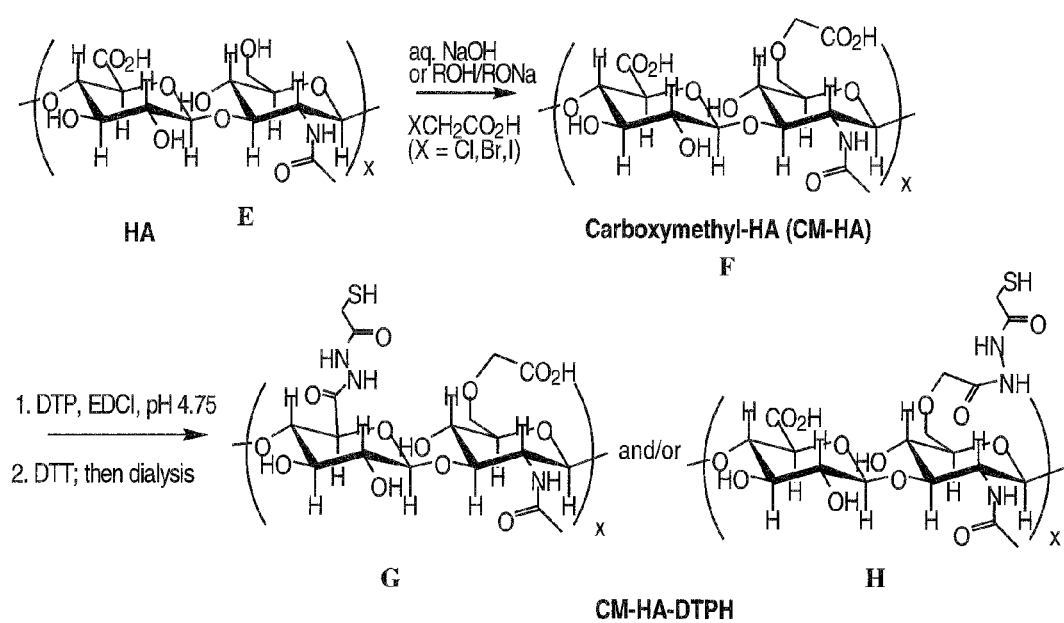
FIG. 4 shows a reaction scheme for producing thiolated hydrazide-modified carboxymethylhyaluronan.

In one aspect, Q in formula III is SH. FIG. 4 depicts one aspect for making compounds having the formula III where Q is SH. The modified-hyaluronan compound F, where a primary hydroxyl group as defined above is converted to the carboxymethyl group, is reacted with 3,3'-dithiobis(propanoic dihydrazide) (DTP) in the presence of the condensing agent such as, for example, EDCI. The hydrazide compound can react with the carboxylic acid group on the glucuronic acid unit of hyaluronan and/or the C-6 carboxymethyl group of the N-acetyl-glucosamine unit of hyaluronan. This reaction produces dihydrazide/disulfide hyaluronan that can be isolated or further manipulated in situ. The disulfide bond of the dihydrazide/disulfide hyaluronan can be cleaved with a reducing agent such as, for example, dithiothreitol (DTT) to produce the hydrazide/thiol compound G and/or H. In one aspect, when Q in formula III is a SH group, L can be $CH_2$, $CH_2CH_2$, or $CH_2CH_2CH_2$.

In another aspect, the hydrazide-modified macromolecule comprises at least one unit comprising the formula L

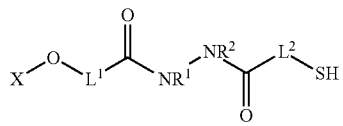

L wherein
X comprises a residue of a macromolecule; and
$R^1$ and $R^2$ comprise, independently, hydrogen, a substituted or unsubstituted hydrocarbyl group, a substituted or unsubstituted heterohydrocarbyl group, or a polyether group;
$L^1$ and $L^2$ comprise, independently, a substituted or unsubstituted hydrocarbyl group, a substituted or unsubstituted heterohydrocarbyl group, a branched- or straight-chain alkylene group, a polyether group, a polyamide group, a polyimino group, an aryl group, a polyester, a polythioether group, a polysaccharyl group, or a combination thereof.

In one aspect of formula L, $R^1$ and $R^2$ are hydrogen. In another aspect of formula L, $L^1$ and $L^2$ are an alkylene group. Examples of alkylene groups can be denoted by the formula $-(CH_2)_n-$, where n is an integer from 1 to 20, 1 to 15, 1 to 10, 1 to 8, 1 to 6 or 1 to 4. In another aspect, $L^1$ is $CH_2$ and $L^2$ is $CH_2CH_2$. In one aspect, X in formula L comprises chondroitin, chondroitin sulfate, dermatan, dermatan sulfate, heparin, heparan sulfate, alginic acid, pectin, or hyaluronan. In another aspect of formula L, X is hyaluronan, $R^1$ and $R^2$ are hydrogen, $L^1$ is $CH_2$, and $L^2$ is $CH_2CH_2$. This compound is referred to herein as Carbylan™-S.

In another aspect, a compound having at least one unit of formula L can be produced by the process comprising (1) reacting a compound comprising the formula LX

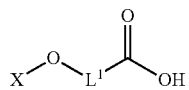

LX wherein
X comprises a residue of a macromolecule; and
$L^1$ comprises a substituted or unsubstituted hydrocarbyl group, a substituted or unsubstituted heterohydrocarbyl group, a branched- or straight-chain alkylene group, a polyether group, a polyamide group, a polyimino group, an aryl group, a polyester, a polythioether group, a polysaccharyl group, or a combination thereof,
with a compound comprising the formula LXV

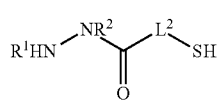

LXV wherein
$R^1$ and $R^2$ comprise, independently, hydrogen, a substituted or unsubstituted hydrocarbyl group, a substituted or unsubstituted heterohydrocarbyl group, or a polyether group, and
$L^2$ comprises a substituted or unsubstituted hydrocarbyl group, a substituted or unsubstituted heterohydrocarbyl group, a branched- or straight-chain alkylene group, a polyether group, a polyamide group, a polyimino group, an aryl group, a polyester, a polythioether group, a polysaccharyl group, or a combination thereof.

The methods described throughout the application can be used in the process above. In one aspect of formula LX, $R^1$ and $R^2$ are hydrogen. In another aspect of formula LX and LXV, $L^1$ and $L^2$ are an alkylene group. Examples of alkylene groups can be denoted by the formula $-(CH_2)_n-$, where n is an integer from 1 to 20, 1 to 15, 1 to 10, 1 to 8, 1 to 6 or 1 to 4. In another aspect, $L^1$ is $CH_2$ and $L^2$ is $CH_2CH_2$. In one aspect, X in formula LX comprises chondroitin, chondroitin sulfate, dermatan, dermatan sulfate, heparin, heparan sulfate, alginic acid, pectin, or hyaluronan. In another aspect of formula LX and LXV, X is hyaluronan, $R^1$ and $R^2$ are hydrogen, $L^1$ is $CH_2$, and $L^2$ is $CH_2CH_2$. This compound is referred to herein as Carbylan™-S.

3. Crosslinked Macromolecules

Described below are methods and compositions for crosslinking any of the modified macromolecules described herein to produce a physiologically compatible macromolecular scaffold useful as a therapeutic aid. "Crosslinking" is defined herein as the ability of two or more macromolecules to produce a pore-containing matrix, where the macromolecules can be the same or different. One or more of macromolecules can be modified using any of the methods and compositions described herein. The use of additional compounds that will facilitate crosslinking are also contemplated.

a) Oxidative Coupling

In general, oxidative coupling involves reacting two or more compounds that each have a SH group in the presence of an oxidant. It is also contemplated that the thiolated compound can couple with itself as well as the other thiolated compound. The reaction between the two SH groups produces a new disulfide bond (—S—S—). In one aspect, the oxidative coupling of a first thiolated compound Y—SH and a second thiolated compound G-SH produces a compound having the fragment VII

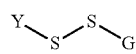

VII wherein Y can be a residue of any macromolecule described herein such as a modified-glycosaminoglycan and G is a residue of the thiolated compound. Depending upon the selection of the macromolecule, the macromolecule can be chemically modified so that the macromolecule has at least on SH group. For example, any naturally-occurring COOH groups or COOH groups added to the macromolecule can be converted to a thiol group using the techniques described herein including, but not limited to, the hydrazide and aminooxy methods described herein.

The second thiolated compound G-SH is any compound having at least one thiol group. The first and second thiolated compounds can be the same or different compounds. In one aspect, the second thiolated compound can be any macromolecule described above. In one aspect, the second thiolated compound is a polysaccharide having at least one SH group.

Any of the polysaccharides described above can be used as the second thiolated compound. In another aspect, the second thiolated compound can be a sulfated-glycosaminoglycan. In a further aspect, the second thiolated compound includes chondroitin, chondroitin sulfate, dermatan, dermatan sulfate, heparin, heparan sulfate, alginic acid, pectin, or carboxymethylcellulose, or hyaluronan, wherein each of these compounds has at least one SH group.

The reaction between the first and second thiolated compounds is performed in the presence of an oxidant. In one aspect, the reaction between the first and second thiolated compounds can be conducted in the presence of any gas that contains oxygen. In one aspect, the oxidant is air. This aspect also contemplates the addition of a second oxidant to expedite the reaction. In another aspect, the reaction can be performed under an inert atmosphere (i.e., oxygen free), and an oxidant is added to the reaction. Examples of oxidants useful in this method include, but are not limited to, molecular iodine, hydrogen peroxide, alkyl hydroperoxides, peroxy acids, dialkyl sulfoxides, high valent metals such as $Co^{+3}$ and $Ce^{+4}$, metal oxides of manganese, lead, and chromium, and halogen transfer agents. The oxidants disclosed in Capozzi, G.; Modena, G. In *The Chemistry of the Thiol Group Part II*; Patai, S., Ed.; Wiley: New York, 1974; pp 785-839, which is incorporated by reference in its entirety, are useful in the methods described herein.

The reaction between the first and second thiolated compounds can be conducted in a buffer solution that is slightly basic. The amount of the first thiolated compound relative the amount of the second thiolated compound can vary. In one aspect, the volume ratio of the first thiolated compound to the second thiolated compound is from 99:1, 90:10, 80:20, 70:30, 60:40, 50:50, 40:60, 30:70, 20:80, 10:90, or 1:99. In one aspect, the first and second thiolated compound react in air and are allowed to dry at room temperature. In this aspect, the dried material can be exposed to a second oxidant, such as hydrogen peroxide. The resultant compound can then be rinsed with water to remove any unreacted first and/or second thiolated compound and any unused oxidant. One advantage of preparing coupled compound via the oxidative coupling methodology described herein is that crosslinking can occur in an aqueous media under physiologically benign conditions without the necessity of additional crosslinking reagents.

In one aspect, described herein is a method for coupling two or more thiolated compounds by reacting a first thiolated compound having the formula X

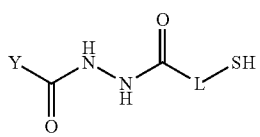

wherein Y can be a residue of any modified-glycosaminoglycan described herein, and L can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof,
with a second thiolated compound having at least one SH group in the presence of an oxidant, wherein the first thiolated compound and second thiolated compound are the same or different compounds. In one aspect, the second thiolated compound has the formula X. In a further aspect, the first and second thiolated compounds are the same compound.

The reaction between the thiolated compound having the formula X and the second thiolated compound produces a crosslinked compound having the fragment VIII

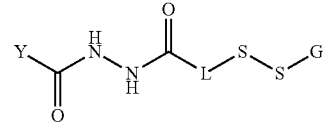

where Y and L are as defined above. In one aspect, L in formula VIII can be $CH_2$, $CH_2CH_2$, or $CH_2CH_2CH_2$. In another aspect, G can be a polysaccharide residue such as, for example, a sulfated-glycosaminoglycan residue. In another aspect, G can be a residue of chondroitin, chondroitin sulfate, dermatan, dermatan sulfate, heparin, heparan sulfate, alginic acid, pectin, or carboxymethylcellulose, or hyaluronan.

In another aspect, described herein is a method for coupling two or more thiolated compounds by reacting a first thiolated compound having the formula XVII

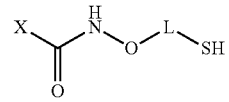

wherein X can be a residue of any macromolecule described herein and L can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof,
with a second thiolated compound having at least one SH group in the presence of an oxidant, wherein the first thiolated compound and second thiolated compound are the same or different compounds.

In one aspect, X is a residue of any modified-glycosaminoglycan described herein. In another aspect, X can be a residue of hyaluronan. In one aspect, the second thiolated compound has the formula XVII. In a further aspect, the first and second thiolated compounds are the same compound.

The reaction between the thiolated compound having the formula XVII and the second thiolated compound produces a crosslinked compound having the fragment XVIII

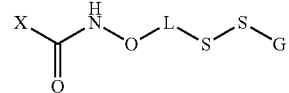

where X and L can be any macromolecule and linker, respectively, described herein. In one aspect, X is a modified-glycosaminoglycan described herein. In another aspect, X and G are a residue of hyaluronan.

b) Coupling Compounds Via the Reaction Between a Thiol Compound and a Thiol-Reactive Compound In another aspect, described herein is a method for coupling two or more compounds by reacting a first thiolated compound having at least one SH group with at least one compound having at least one thiol-reactive electrophilic functional group. In one aspect, the compound has at least two-thiol reactive functional groups.

Any of the thiolated macromolecules described above or macromolecules that can be thiolated can be used in this aspect as the first thiolated compound. Two or more different macromolecules can be used in this method. For example, a second thiolated compound can be used in combination with the first thiolated compound. In this aspect, the first and second thiolated compound can be the same or different compounds.

In one aspect, the first and second thiolated compound can be a polysaccharide. In this aspect, the polysaccharide is a sulfated-glycosaminoglycan including, but not limited to, chondroitin, chondroitin sulfate, dermatan, dermatan sulfate, heparin, heparan sulfate, alginic acid, pectin, or carboxymethylcellulose.

In another aspect, the first thiolated compound is hyaluronan. In another aspect, the first thiolated compound has the formula XVII described above. In this aspect, X is a residue of hyaluronan and L is $CH_2$, $CH_2CH_2$ or $CH_2CH_2CH_2$. In another aspect, X is a residue of a modified-glycosaminoglycan.

In another aspect, the first thiolated compound has the formula X described above. In one aspect, Y in formula X is a modified-glycosaminoglycan.

In one aspect, the thiol-reactive compound contains one or more thiol-reactive electrophilic functional groups as defined above. In one aspect, the thiol-reactive compound has two electron-deficient vinyl groups, wherein the two electron-deficient vinyl groups are the same. In another aspect, the thiol-reactive compound is a diacrylate, a dimethacrylate, a diacrylamide, a dimethacrylamide, or a combination thereof. In another aspect, the thiol-reactive compound can be a dendrimer having a plurality of thiol-reactive groups. In one aspect, the thiol-reactive compound can have from 2 to 100, 2 to 90, 2 to 80, 2 to 70, 2 to 60, 2 to 50, 2 to 40, 2 to 30, 2 to 20 or 2 to 10 thiol-reactive groups.

In another aspect, the thiol-reactive compound has the formula XX

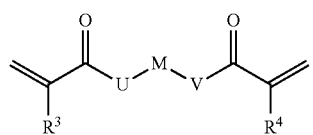

XX wherein $R^3$ and $R^4$ are, independently, hydrogen or lower alkyl;

U and V are, independently, O or $NR^5$, wherein $R^5$ is, independently, hydrogen or lower alkyl; and M is a polyalkylene group, a polyether group, a polyamide group, a polyimino group, a polyester, an aryl group, or a polythioether group.

In one aspect, $R^3$ and $R^4$ are hydrogen, U and V are oxygen, and M is a polyether group. This compound is referred to herein as polyetheylene glycol diacrylate or PEGDA. In another aspect, $R^3$ and $R^4$ are hydrogen, U and V are NH, and M is a polyether group. In a further aspect, $R^3$ and $R^4$ are methyl, U and V are oxygen, and M is a polyether group. In another aspect, $R^3$ and $R^4$ are methyl, U and V are NH, and M is a polyether group.

In another aspect, the thiol-reactive compound is any bioactive agent described above containing at least one thiol-reactive electrophilic group. For example, Mitomycin C (MMC) can be converted to the corresponding acrylate (MMC-acrylate). MMC-acrylate can then be coupled with any of the thiolated macromolecules described herein.

In another aspect, the first thiolated compound has the formula X or XVII described above, wherein L is $CH_2CH_2$ or $CH_2CH_2CH_2$, and the thiol-reactive compound has the formula XX described above, wherein $R^3$ and $R^4$ are, independently, hydrogen or lower alkyl; U and V are, independently, O or $NR^5$, wherein $R^5$ is, independently, hydrogen or lower alkyl; and M is a polyether group.

In another aspect, described herein is a method for coupling a compound by reacting a first thiolated compound having at least one thiol-reactive electrophilic functional group with at least one compound having at least two thiol groups. Any of the thiolated macromolecules and thiol-reactive electrophilic functional groups described above can be used in this aspect. In one aspect, a thiol-reactive compound having at least one fragment having the formula XVI

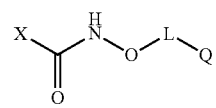

XVI wherein

X can be a residue of any macromolecule described herein;

Q is the thiol-reactive electrophilic functional group; and

L can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof, is reacted with at least one compound having at least two thiol groups.

In one aspect, when Q of formula XVI is thiol-reactive electrophilic functional group, X is a polysaccharide such as hyaluronan and L is $CH_2CH_2$ or $CH_2CH_2CH_2$. In another aspect, Q is an acrylate, a methacrylate, an acrylamide, or a methacrylamide.

In one aspect, examples of compounds having at least two thiol groups include, but are not limited to, propane-1,3-dithiol, polyethylene glycol-α,Ω-dithiol, para, ortho, or meta-bisbenzyl thiol, dithiothreitol, a peptide containing two or more cysteine residues, or dendrimeric thiols.

The compounds produced by coupling a thiolated compound with a compound having at least one thiol-reactive electrophilic functional group possess at least one fragment of the formula XXVII

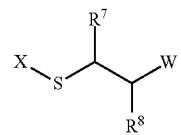

XXVII wherein $R^7$ and $R^8$ are, independently, hydrogen or lower alkyl;

W is an electron-withdrawing group described above; and

X can be a residue of any macromolecule described herein.

In one aspect, X can be a residue of a polysaccharide such as hyaluronan or a sulfated-glycosaminoglycan. In another aspect, X can be a residue of a modified-glycosaminoglycan. In another aspect, $R^7$ is hydrogen and $R^8$ is hydrogen or methyl. In another aspect, X is a residue of a modified-glycosaminoglycan; $R^7$ is hydrogen; $R^8$ is hydrogen or methyl; and W is an ester group or an amide group.

In one aspect, the reaction product between the thiolated compound and thiol-reactive compound has at least one fragment having the formula XII

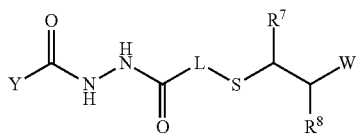

XII wherein
$R^7$ and $R^8$ can be, independently, hydrogen or lower alkyl;
W can be any electron-withdrawing group described herein;
Y can be a residue of any modified-glycosaminoglycan described herein; and
L comprises a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof.

In another aspect, the reaction product between the thiolated compound and thiol-reactive compound has at least one fragment having the formula XIII

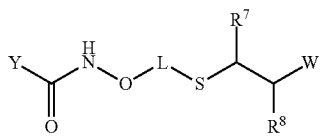

XIII wherein
$R^7$ and $R^8$ can be, independently, hydrogen or lower alkyl;
W can be any electron-withdrawing group described herein;
Y can be a residue of any modified-glycosaminoglycan described herein; and
L comprises a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof.

In another aspect, the reaction product between the thiolated compound and thiol-reactive compound has at least one fragment having the formula XIV

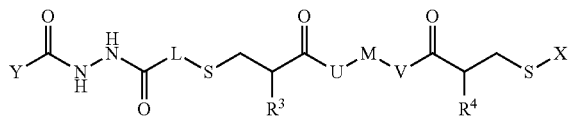

XIV wherein
$R^3$ and $R^4$ can be, independently, hydrogen or lower alkyl;
U and V can be, independently, O or $NR^5$, wherein $R^5$ is, independently, hydrogen or lower alkyl;
Y can be a residue of any modified-glycosaminoglycan described herein;
X can be a residue of any macromolecule described herein; and
L and M can be, independently, a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof.

In one aspect, Y in formula XIV is $X'OCH_2$—, wherein X' comprises a residue of a macromolecule. Examples of the macromolecule X' include, but are not limited to, chondroitin, chondroitin sulfate, dermatan, dermatan sulfate, heparin, heparan sulfate, alginic acid, or pectin. In another aspect, X' is hyaluronan. In another aspect of formula XIV, $R^3$ and $R^4$ are hydrogen, U and V are oxygen, and M is a polyether group. In a further aspect, L in formula XIV is a $CH_2CH_2$ group. In another aspect of formula XIV, Y is $X'OCH_2$—, wherein X' is hyaluronan, $R^3$ and $R^4$ are hydrogen, U and V are oxygen, M is a polyether group, L is a $CH_2CH_2$ group, and X is $CH_2CH_2C(O)NHNHC(O)X''$, where X'' is a residue of hyaluronan. This compound is also referred to herein as Carbylan™-SX. In yet another aspect of formula XIV, Y is $X'OCH_2$—, wherein X' is hyaluronan, $R^3$ and $R^4$ are hydrogen, U and V are oxygen, M is a polyether group, L is a $CH_2CH_2$ group, and X is $CH_2CH_2C(O)NHNHC(O)X''$, where X'' is a residue of gelatin. This compound is also referred to herein as Carbylan™-GSX.

In another aspect, the reaction product between the thiolated compound and thiol-reactive compound has at least one fragment having the formula XV

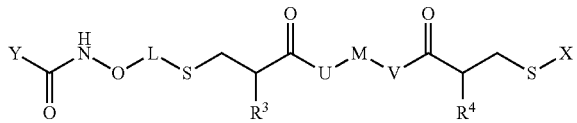

XV wherein
$R^3$ and $R^4$ can be, independently, hydrogen or lower alkyl;
U and V can be, independently, O or $NR^5$, wherein $R^5$ is, independently, hydrogen or lower alkyl;
Y can be a residue of any modified-glycosaminoglycan described herein;
X can be a residue of any macromolecule described herein; and
L and M can be, independently, a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof.

In another aspect, the reaction product between the thiolated compound and thiol-reactive compound has at least one fragment having the formula XXI

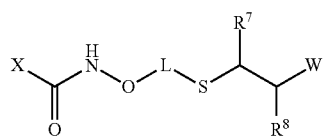

XXI wherein
$R^7$ and $R^8$ can be, independently, hydrogen or lower alkyl;

W can be any electron-withdrawing group described herein;

X can be a residue of any macromolecule described herein; and

L can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof.

In another aspect, the reaction product between the thiolated compound and thiol-reactive compound has at least one fragment having the formula XXII

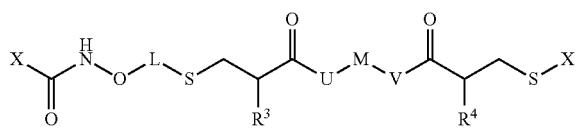

XXII wherein
$R^3$ and $R^4$ can be, independently, hydrogen or lower alkyl;
U and V can be, independently, O or $NR^5$, wherein $R^5$ is, independently, hydrogen or lower alkyl;
Y can be a residue of any modified-glycosaminoglycan described herein;
X can be a residue of any macromolecule described herein; and
L and M can be, independently, a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof.

In another aspect, a compound produced by the process comprising reacting any of the thiolated compounds having the formula L with a compound comprising the formula XX

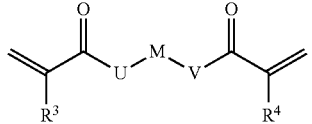

XX wherein
$R^3$ and $R^4$ comprise, independently, hydrogen or lower alkyl;
U and V comprise, independently, O or $NR^5$, wherein $R^5$ is, independently, hydrogen or lower alkyl; and
M comprises a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof.

In one aspect, $R^3$ and $R^4$ in formula XX are hydrogen, U and V are oxygen, and M is a polyether group. In another aspect, $R^3$ and $R^4$ are hydrogen, U and V are NH, and M is a polyether group. In a further aspect, $R^3$ and $R^4$ are methyl, U and V are oxygen, and M is a polyether group. In another aspect, $R^3$ and $R^4$ are methyl, U and V are NH, and M is a polyether group.

Figure 8:
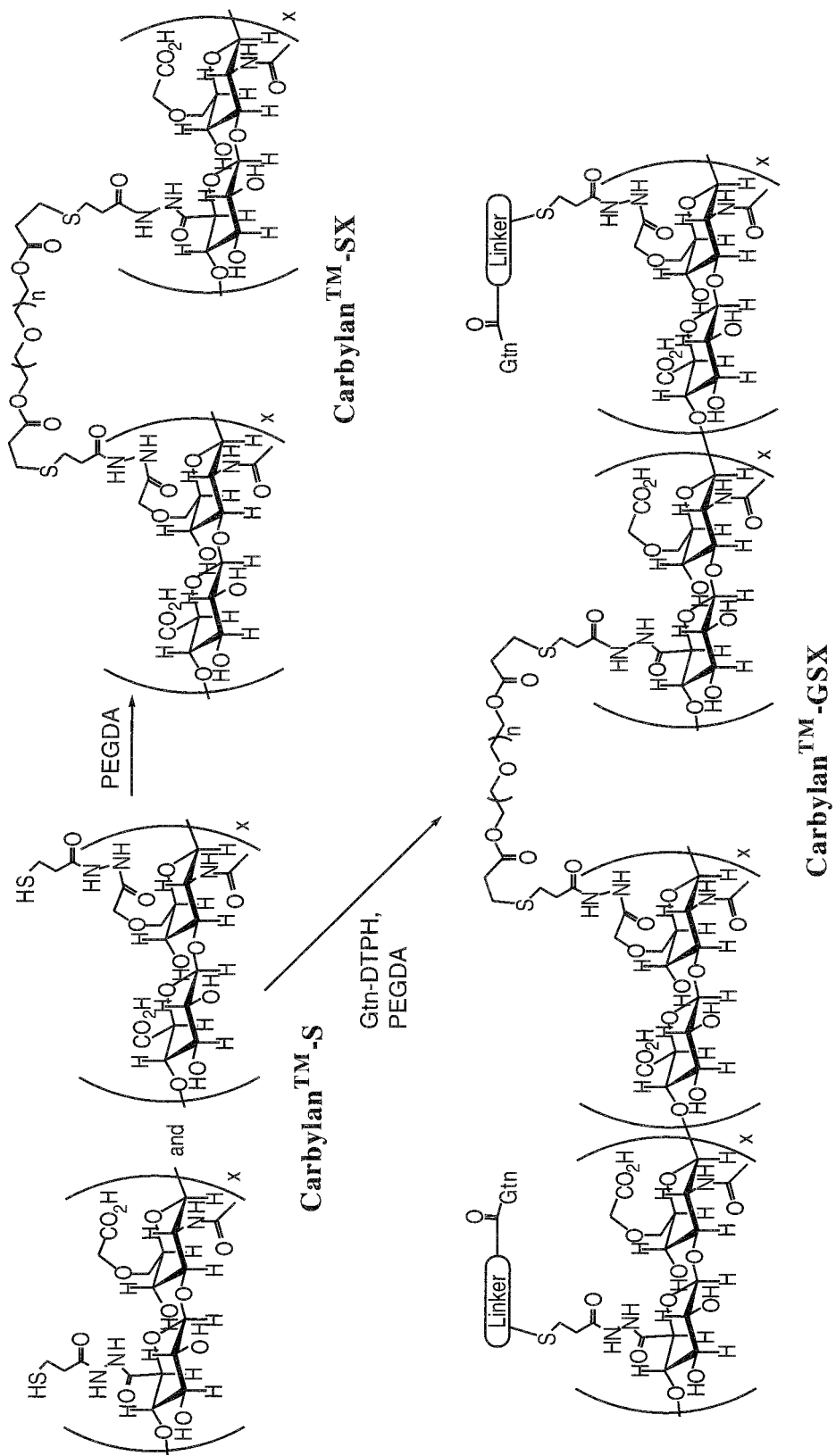
FIG. 8 shows a reaction scheme for producing Carbylan™-SX and Carbylan™-GSX.

In one aspect, the thiolated compound has the formula L, wherein X is hyaluronan, $R^1$ and $R^2$ are hydrogen, $L^1$ is $CH_2$, and $L^2$ is $CH_2CH_2$. In another aspect, the thiolated compound has the formula L, wherein X is hyaluronan, $R^1$ and $R^2$ are hydrogen, $L^1$ is $CH_2$, and $L^2$ and the compound having the formula XX is poly(ethylene glycol)diacrylate. This reaction is depicted in FIG. 8. The reaction product is also referred to herein as Carbylan™-SX.

It is also contemplated that the thiolated molecule can be two or more different thiolated molecules. In one aspect, the thiolated molecule comprises two thiolated molecules, wherein the first thiolated molecule is a compound having the formula L, wherein X is hyaluronan, $R^1$ and $R^2$ are hydrogen, $L^1$ is $CH_2$, and $L^2$ is $CH_2CH_2$, the second thiolated molecule is a thiolated macromolecule, and the compound having the formula XX is poly(ethylene glycol)diacrylate. Examples of thiolated macromolecules include, but are not limited to, chondroitin sulfate, thiolated dermatan, thiolated heparan, thiolated heparin, thiolated dermatan sulfate, thiolated heparan sulfate, thiolated alginic acid, or thiolated pectin. In one aspect, the thiolated macromolecule can be modified with a hydrazide group having a thiol group using the techniques described herein. In one aspect, the second thiolated molecule is thiolated gelatin, wherein the gelatin is modified with a hydrazide group having a thiol group.

In one aspect, the thiolated molecule comprises two thiolated molecules, wherein the first thiolated molecule is a compound having the formula L, wherein X is hyaluronan, $R^1$ and $R^2$ are hydrogen, $L^1$ is $CH_2$, and $L^2$ is $CH_2CH_2$, the second thiolated molecule is thiolated gelatin, and the compound having the formula XX is poly(ethylene glycol)diacrylate. This reaction is depicted in FIG. 8, and the reaction product is referred to herein as Carbylan™-GSX.

In one aspect, the reaction between the thiol reactive compound and thiol compound is generally conducted at a pH of from 7 to 12, 7.5 to 11, 7.5 to 10, or 7.5 to 9.5, or a pH of 8. In one aspect, the solvent used can be water (alone) or an aqueous containing organic solvent. In one aspect, when the mixed solvent system is used, a base such as a primary, secondary, or tertiary amine can used. In one aspect, an excess of thiol compound is used relative to the thiol-reactive compound in order to ensure that all of the thiol-reactive compound is consumed during the reaction. Depending upon the selection of the thiol reactive compound, the thiol compound, the pH of the reaction, and the solvent selected, coupling can occur from within minutes to several days. If the reaction is performed in the presence of an oxidant, such as air, the thiol compound can react with itself or another thiol compound via oxidative addition to form a disulfide linkage in addition to reacting with the thiol-reactive compound.

c) Crosslinking Via Polycarbonyl Crosslinkers

In one aspect, a polycarbonyl crosslinker can react with any of the modified macromolecules described herein. The term "polycarbonyl crosslinker" is defined herein as a compound that possesses two or more groups represented by the formula C(O)R, where R is hydrogen, lower alkyl, or OR', where R' is a group that results in the formation of an activated ester. In one aspect, any of the hydrazide-modified macromolecules and aminooxy-modified macromolecules can be crosslinked with a polyaldehyde. A polyaldehyde is a compound that has two or more aldehyde groups [C(O)H]. In one aspect, the polyaldehyde is a dialdehyde compound.

In one aspect, any compound possessing two or more aldehyde groups can be used as the polyaldehyde crosslinker. In one aspect, the polyaldehyde can be substituted or unsubstituted hydrocarbyl or substituted or unsubstituted heterohydrocarbyl. In another embodiment, the polyadlehyde can contain a polysaccharyl group or a polyether group. In a further aspect, the polyaldehyde can be a dendrimer or peptide. In one aspect, a polyether dialdehyde such as poly(ethylene glycol)propiondialdehyde (PEG) is useful in the compositions and methods described herein. PEG can be purchased from many commercial sources, such as Shearwater Polymers, Inc. (Huntsville, Ala.). In another aspect, the polyaldehyde is glutaraldehyde.

In another aspect, when the polycarbonyl compound is a polyaldehyde, the polyaldehyde can be prepared by the oxidation of terminal polyols or polyepoxides possessing two or more hydroxy or epoxy groups, respectively, using techniques known in the art.

The method of crosslinking generally involves reacting the modified macromolecule with the polycarbonyl crosslinker in the presence of a solvent. In one aspect, the carbonyl group of the polycarbonyl reacts with the hydrazide group or the amino group of the aminooxy group of the modified macromolecule to produce a new carbon-nitrogen double bond.

Scheme 3 depicts one aspect of using a dicarbonyl compound A, where $R^{29}$ and $R^{30}$ can be, independently, hydrogen, lower alkyl, or OR' as defined above, as a crosslinker. The carbonyl group of compound B, which is the result of one condensation reaction between a first hydrazide-modified macromolecule and the dicarbonyl, can react with the hydrazide group of a second hydrazide-modified polysaccharide C to produce another carbon-nitrogen double bond, which results in the formation of a unit depicted in Formula V.

In view of Scheme 3, it is possible to crosslink two or more modified macromolecules to produce a matrix. Although the polycarbonyl crosslinker is intended to react with hydrazide groups or aminooxy groups on different modified macromolecules, it is also possible that the polycarbonyl crosslinker can react with two or more hydrazide groups or aminooxy groups present on the same modified macromolecule.

It also evident in Scheme 3 that the modified macromolecules can be different or the same. Thus, in one aspect, X and Y in formula V can be the same macromolecule residue. In another aspect, X and Y can be different macromolecule residues. In one aspect, X and Y are, independently, a residue of chondroitin, chondroitin sulfate, dermatan, dermatan sulfate, heparin, heparan sulfate, alginic acid, pectin, or carboxymethylcellulose. In another aspect, X and Y are a residue of hyaluronan. In another aspect, X and/or Y are a residue of a modified-glycosaminoglycan.

In one aspect, when Y in formula V is a modified-glycosaminoglycan, Z can be a polyether. In another aspect, when Y in formula V is a modified-glycosaminoglycan, $R^1$, $R^2$, $R^5$, $R^6$, $R^7$, and $R^8$ are hydrogen. In another aspect, when Y in formula V is a modified-glycosaminoglycan, $R^3$ and $R^4$ can be an alkyl group such as, for example, $(CH_2)_n$, wherein n is from 1 to 20, 1 to 18, 1 to 16, 1 to 14, 1 to 12, 1 to 10, 1 to 8, 2 to 6, or 2 to 4. In another aspect, crosslinked macromolecules can be produced by reacting (1) a modified macromolecule comprising the reaction product between adipic dihydrazide and a modified-glycosaminoglycan and (2) a

SCHEME 3

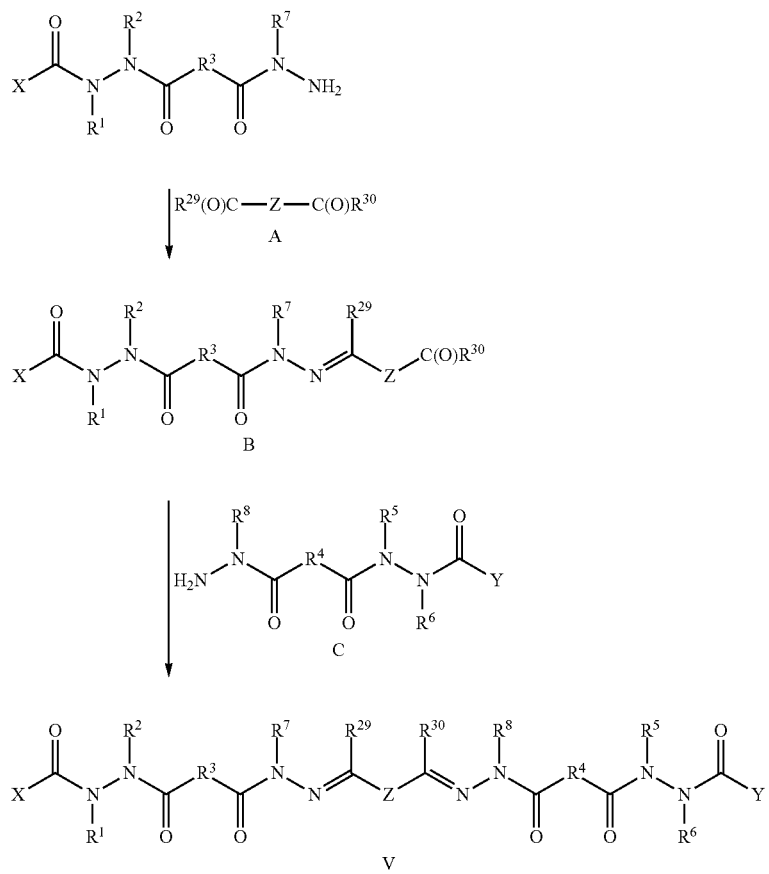

poly(ethylene glycol) propiondialdehyde. In another aspect, crosslinked macromolecules can be produced by reacting (1) a modified macromolecule comprising the reaction product between an aminooxy ether compound possessing two or more aminooxy groups and a macromolecule and (2) a poly(ethylene glycol) propiondialdehyde.

In another aspect, the reaction product between a polycarbonyl crosslinker and an aminooxy-modified macromolecule has at least one fragment having the formula VI

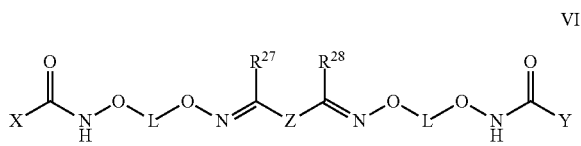

wherein
X and Y can be a residue of any macromolecule described herein;
$R^{27}$ and $R^{28}$ can be, independently, hydrogen or lower alkyl; and
L and Z can be, independently, a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof.

In one aspect, X and Y are a residue of a polysaccharide such as a sulfated-glycosaminoglycan or hylauronan. In another aspect, Y can be a modified-glycosaminoglycan.

In another aspect, one or more hydroxyl groups present on the macromolecule can be oxidized to the corresponding aldehyde, which then can undergo crosslinking with a hydrazide compound or an aminooxy ether compound. In one aspect, periodate can be used to oxidize the macromolecule.

The overall number of crosslinks and the number of different modified macromolecules that are cross linked together are dependent on the number of reactive carbonyl groups in the polycarbonyl crosslinker and dihydrazide groups or aminooxy groups present on the modified macromolecule. In one aspect, there is at a minimum at least one crosslink (i.e., unit) having the formula V or VI. In one aspect, 1% to 100%, 10% to 90%, 30% to 80%, or 40% to 70% of the dihydrazide groups or aminooxy groups are crosslinked with the polycarbonyl crosslinker. In another aspect, the compound has from 10 to 10,000 units, 10 to 9,000 units, 10 to 8,000 units, 10 to 7,000 units, 10 to 6,000 units, 10 to 5,000 units, 10 to 4,000 units, 10 to 3,000 units, 10 to 2,000 units, or 10 to 1,000 units having the formula V or VI.

In one aspect, adipic dihydrazide (ADH) will crosslink when it modifies the uronic acid in 1%-99% of the glycosaminoglycan or 1-50%. In one aspect, modification of the carboxylic acid containing polysaccharide such as glycosaminoglycan (for example HA) can contain 10-90% or 20-80% or 30-70% or 40-60% or about 50% derivatization and the derivatized polysaccharide can contain greater than 10% or 20% or 30% or 40% or 50% or 60% or 70% or 80% or 90% or 99% crosslinking. For example, a hyaluronan (HA) with 5,000 disaccharide units (normal high MW HA) has 5,000 carboxylic acid groups available. A 1% modification means that there are 50 ADHs per HA molecule, 10% would be 500 ADH/HA, etc. Thus, even at low modification levels, there are numerous sites per modified GAG molecule to form crosslinks.

Any of the techniques and procedures for crosslinking polyaldehydes with polysaccharides disclosed in International publication no. WO 02/06373, which is incorporated by reference in its entirety, can be used in the methods described herein. In one aspect, after the reaction between the polycarbonyl crosslinker and the modified macromolecule is complete, the solvent present in the crosslinked macromolecule can be evaporated by any method known in the art such as air-drying, rotary evaporation at low pressure and/or lyophilization. In one aspect, at least 80%, at least 85%, at least 90%, at least 95%, and at least 98% of the solvent contained within the crosslinked macromolecule should evaporate.

In one aspect, the reaction solvent is water. In addition, small amounts of water miscible organic solvents, such as an alcohol or DMF or DMSO, can be used as well. In one aspect, crosslinking can be performed at room temperature, for example, 25° C., but the cross-linking reaction can be performed within a range of temperatures from below 4° C. to above 90° C. but typically would be performed at between 4° C. and 60° C., more typically between 4° C. and 50° C., and more preferably at 4° C. or 30° C. or 37° C. The reaction will also work at a variety of pHs between, for example, pH from 3 to 10, or pH from 4 to 9, or pH from 5 to 8, or preferably at neutral pH.

4. Anti-Adhesion Composites

In one aspect, described herein are composites comprising (1) a first compound comprising a first anti-adhesion compound covalently bonded to a first anti-adhesion support and (2) a first prohealing compound.

The term "anti-adhesion compound" as referred to herein is defined as any compound that prevents cell attachment, cell spreading, cell growth, cell division, cell migration, or cell proliferation. In one aspect, compounds that induce apoptosis, arrest the cell cycle, inhibit cell division, and stop cell motility can be used as the anti-adhesion compound. Examples of anti-adhesion compounds include, but are not limited to anti-cancer drugs, anti-proliferative drugs, PKC inhibitors, ERK or MAPK inhibitors, cdc inhibitors, antimitotics such as colchicine or taxol, DNA intercalators such as adriamycin or camptothecin, or inhibitors of PI3 kinase such as wortmannin or LY294002. In one aspect, the anti-adhesion compound is a DNA-reactive compound such as mitomycin C. In another aspect, any of the oligonucleotides disclosed in U.S. Pat. No. 6,551,610, which is incorporated by reference in its entirety, can be used as the anti-adhesion compound. In another aspect, any of the anti-inflammatory drugs described below can be the anti-adhesion compound. Examples of anti-inflammatory compounds include, but are not limited to, methyl prednisone, low dose aspirin, medroxy progesterone acetate, and leuprolide acetate.

The term "anti-adhesion support" as referred to herein is defined as any compound that is capable of forming a covalent bond with the anti-adhesion compound that does not adhere to, spread, or proliferate cells. In one aspect, the anti-adhesion support is a hydrophilic, natural or synthetic polymer. Any of the polyanionic polysaccharides disclosed in U.S. Pat. No. 6,521,223, which is incorporated by reference in its entirety, can be used as the anti-adhesion support. Examples of polyanionic polysaccharides include, but are not limited to, hyaluronan, sodium hyaluronate, potassium hyaluronate, magnesium hyaluronate, calcium hyaluronate, carboxymethylcellulose, carboxymethyl amylose, or a mixture of hyaluronic acid and carboxymethylcellulose.

The formation of the first compound involves reacting the anti-adhesion compound with the anti-adhesion support to form a new covalent bond. In one aspect, the anti-adhesion compound possesses a group that is capable of reacting with the anti-adhesion support. The group present on the anti-adhesion compound that can react with the anti-adhesion support can be naturally-occurring or the anti-adhesion compound can be chemically modified to add such a group. In another aspect, the anti-adhesion support can be chemically modified so that it is more reactive with the anti-adhesion compound.

In one aspect, the first compound can be formed by crosslinking the anti-adhesion compound with the anti-adhesion support. In one aspect, the anti-adhesion compound and the anti-adhesion support each possess at least one hydrazide group or aminooxy group, which then can react with a crosslinker such as, for example, a polycarbonyl crosslinker having at least two hydrazide-reactive groups or at least two aminooxy-reactive groups. Any of the hydrazide-reactive groups, aminooxy-reactive groups, and polycarbonyl crosslinkers described above can be used in this aspect. In one aspect, the crosslinker is a polyethylene glycol dialdehyde. Additionally, any of the hydrazide-modified macromolecules and aminooxy-modified macromolecules described above can be used as the first anti-adhesion support.

In another aspect, the first compound can be formed by the oxidative coupling of the anti-adhesion compound with the anti-adhesion support. In one aspect, when the anti-adhesion compound and the anti-adhesion support each possess a thiol group, the anti-adhesion compound and the anti-adhesion support can react with one another in the presence of an oxidant to form a new disulfide bond. Any of the oxidants described above can be used in this aspect. Additionally, any of the thiolated hydrazide-modified macromolecules and thiolated aminooxy-modified macromolecules described above can be used as first anti-adhesion support. For example, compounds having at least one fragment X or XVII can be used as the first anti-adhesion support.

The reaction between the anti-adhesion compound and the anti-adhesion support can be conducted in a buffer solution that is slightly basic. The amount of the anti-adhesion compound relative the amount of the anti-adhesion support can vary. In one aspect, the volume ratio of the anti-adhesion compound to the anti-adhesion support is from 99:1, 90:10, 80:20, 70:30, 60:40, 50:50, 40:60, 30:70, 20:80, 10:90, or 1:99. In one aspect, the anti-adhesion compound and the anti-adhesion support react in air and are allowed to dry at room temperature. In this aspect, the dried material can be exposed to a second oxidant, such as hydrogen peroxide. The resultant compound can then be rinsed with water to remove any unreacted anti-adhesion compound, anti-adhesion support, and any unused oxidant. One advantage of preparing the first compound via the oxidative coupling methodology described herein is that coupling can occur in an aqueous media under physiologically benign conditions without the necessity of additional crosslinking reagents.

In another aspect, the first compound is produced by reacting the anti-adhesion support having at least one SH group with at least one anti-adhesion compound having at least one thiol-reactive electrophilic functional group. In one aspect, the anti-adhesion compound is mitomycin C having an acrylate group.

In another aspect, the first compound is produced by reacting the anti-adhesion support having at least one thiol-reactive electrophilic functional group with at least one anti-adhesion compound having at least two thiol groups. Any of the compounds described above that possess a thiol-reactive electrophilic functional group can be used in this aspect. For example, compounds having at least one fragment having the formula III or XVI can be used as the first adhesion support.

In one aspect, the reaction between the thiol reactive compound (anti-adhesion compound or the anti-adhesion support) and the thiol compound (anti-adhesion compound or the anti-adhesion support) is generally conducted at a pH of from 7 to 12, 7.5 to 11, 7.5 to 10, or 7.5 to 9.5, or a pH of 8. In one aspect, the solvent used can be water (alone) or an aqueous solution containing an organic solvent. In one aspect, when the mixed solvent system is used, a base such as a primary, secondary, or tertiary amine can be used. In one aspect, an excess of thiol compound is used relative to the thiol-reactive compound in order to ensure that all of the thiol-reactive compound is consumed during the reaction. Depending upon the selection of the thiol reactive compound, the thiol compound, the pH of the reaction, and the solvent selected, coupling can occur from within minutes to several days. If the reaction is performed in the presence of an oxidant, such as air, the thiol compound can react with itself or another thiol compound via oxidative addition to form a disulfide linkage in addition to reacting with the thiol-reactive compound.

The composite can optionally contain unreacted (i.e., free) anti-adhesion compound. The unreacted anti-adhesion compound can be the same or different anti-adhesion compound that is covalently bonded to the anti-adhesion support.

The composite is composed of a prohealing compound. The term "prohealing drug" as defined herein is any compound that promotes cell growth, cell proliferation, cell migration, cell motility, cell adhesion, or cell differentiation. In one aspect, the prohealing compound includes a protein or synthetic polymer. Proteins useful in the methods described herein include, but are not limited to, an extracellular matrix protein, a chemically-modified extracellular matrix protein, or a partially hydrolyzed derivative of an extracellular matrix protein. The proteins may be naturally occurring or recombinant polypeptides possessing a cell interactive domain. The protein can also be mixtures of proteins, where one or more of the proteins are modified. Specific examples of proteins include, but are not limited to, collagen, elastin, decorin, laminin, or fibronectin.

In one aspect, the synthetic polymer has at least one carboxylic acid group or the salt or ester thereof, which is capable of reacting with a hydrazide or an aminooxy ether compound. In one aspect, the synthetic polymer comprises glucuronic acid, polyacrylic acid, polyaspartic acid, polytartaric acid, polyglutamic acid, or polyfumaric acid.

In another aspect, the prohealing compound can be any of the supports disclosed in U.S. Pat. No. 6,548,081 B2, which is incorporated by reference in its entirety. In one aspect, the prohealing compound includes cross-linked alginates, gelatin, collagen, cross-linked collagen, collagen derivatives, such as, succinylated collagen or methylated collagen, cross-linked hyaluronan, chitosan, chitosan derivatives, such as, methylpyrrolidone-chitosan, cellulose and cellulose derivatives such as cellulose acetate or carboxymethyl cellulose, dextran derivatives such carboxymethyl dextran, starch and derivatives of starch such as hydroxyethyl starch, other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyoxanones and polyoxalates, copolymer of poly(bis(p-carboxyphenoxy)propane)anhydride (PCPP) and sebacic acid, poly(L-glutamic acid), poly(D-glutamic acid), polyacrylic acid, poly(DL-glutamic acid), poly(L-aspartic acid), poly(D-aspartic acid), poly(DL-aspartic acid), polyethylene glycol, copolymers of the above listed polyamino acids with polyethylene glycol, polypeptides, such as, collagen-like, silk-like, and silk-elastin-like proteins, polycaprolactone, poly(alkylene succinates), poly(hydroxy butyrate) (PHB), poly(butylene diglycolate), nylon-2/nylon-6-co-polyamides, polydihydropyrans, polyphosphazenes, poly(ortho ester), poly(cyano acrylates), polyvinylpyrrolidone, polyvinylalcohol, poly casein, keratin, myosin, and fibrin. In another aspect, highly cross-linked HA can be the prohealing compound.

In another aspect, the prohealing compound can be a polysaccharide. In one aspect, the polysaccharide has at least one group, such as a carboxylic acid group or the salt or ester thereof, that can react with a dihydrazide. In one aspect, the polysaccharide is a glycosaminoglycan (GAG). Any of the glycosaminoglycans described above can be used in this aspect. In another aspect, the prohealing compound is hyaluronan.

The composite can optionally contain a second prohealing compound. In one aspect, the second prohealing compound can be a growth factor. Any substance or metabolic precursor which is capable of promoting growth and survival of cells and tissues or augmenting the functioning of cells is useful as a growth factor. Examples of growth factors include, but are not limited to, a nerve growth promoting substance such as a ganglioside, a nerve growth factor, and the like; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF), interleukin-1 (IL-1), vascular endothelial growth factor (VEGF) and keratinocyte growth factor (KGF), dried bone material, and the like; and antineoplastic agents such as methotrexate, 5-fluorouracil, adriamycin, vinblastine, cisplatin, tumor-specific antibodies conjugated to toxins, tumor necrosis factor, and the like. The amount of growth factor incorporated into the composite will vary depending upon the growth factor and prohealing compound selected as well as the intended end-use of the composite.

Any of the growth factors disclosed in U.S. Pat. No. 6,534, 591 B2, which is incorporated by reference in its entirety, can be used in this aspect. In one aspect, the growth factor includes transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); inhibins (for example, Inhibin A, Inhibin B); growth differentiating factors (for example, GDF-1); and Activins (for example, Activin A, Activin B, Activin AB).

Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

In another aspect, the addition of a crosslinker can be used to couple the first compound with the prohealing compound. In one aspect, when the first compound and the prohealing compound possess free thiol groups, a crosslinker having at least two thiol-reactive electrophilic groups can be used to couple the two compounds. Additionally, the crosslinker can couple two first compounds or two prohealing compounds.

In one aspect, the crosslinker is a thiol-reactive compound having two electron-deficient vinyl groups, wherein the two electron-deficient vinyl groups are the same. In another aspect, the thiol-reactive compound is a diacrylate, a dimethacrylate, a diacrylamide, a dimethacrylamide, or a combination thereof. In another aspect, the thiol-reactive compound has the formula XX discussed above.

The composites described herein can assume numerous shapes and forms depending upon the intended end-use. In one aspect, the composite is a laminate, a gel, a bead, a sponge, a film, a mesh, or a matrix. The procedures disclosed in U.S. Pat. Nos. 6,534,591 B2 and 6,548,081 B2, which are incorporated by reference in their entireties, can be used for preparing composites having different forms.

In one aspect, the composite is a laminate. In one aspect, the laminate includes a first layer and a second layer, wherein (1) the first layer comprises a first compound comprising a first anti-adhesion compound covalently bonded to a first anti-adhesion support, wherein the first layer has a first surface and a second surface, and (2) the second layer comprises a first prohealing compound, wherein the second layer has a first surface and a second surface, wherein the first surface of the first layer is adjacent to the first surface of the second layer. In this aspect, the first layer is adjacent to the second layer. Depending upon the selection of the first compound and the prohealing compound, the first compound and the prohealing compound can either be covalently bonded to one another or merely in physical contact with one another without any chemical reaction occurring between the two compounds. In one aspect, the first compound and the prohealing compound possess free thiol groups, which can form new disulfide bonds in the presence of an oxidant.

In one aspect, a second layer of prohealing compound can be applied to a film of first layer. In one aspect, the width of the interface between the first and second layers can vary depending upon the casting time of the first layer. For example, if the casting time of the first layer is long, the width of the interface formed upon the application of the second layer will be decreased. Similarly, if the casting time of the first layer is short, a wider interface will be produced. By varying the width of the interface between the first and second layer, it is possible to create a gradient that will prevent cell growth either immediately (narrow interface) or gradually (wide interface). In another aspect, another layer of prohealing compound can be applied to the other surface of the first layer to produce a sandwich of first layer encased by prohealing compound. FIG. 4 depicts one aspect of this sandwich laminate.

In one aspect, the composite can be molded into any desired shape prior to delivery to a subject. In another aspect, the second layer (prohealing compound) can be applied to a subject followed by the application of the first compound to the exposed second layer. In a further aspect, another layer containing the prohealing compound can be applied to the exposed surface of the first layer. In this aspect, a sandwich laminate is formed in situ in the subject.

In one aspect, the first compound and prohealing compound can be used as a kit. For example, the first compound and prohealing compound are in separate syringes, with the contents being mixed using syringe-to-syringe techniques just prior to delivery to the subject. In this aspect, the first compound and prohealing compound can be extruded from the opening of the syringe by an extrusion device followed by spreading the mixture via spatula.

In another aspect, the first compound and the prohealing compound are in separate chambers of a spray can or bottle with a nozzle or other spraying device. In this aspect, the first compound and prohealing compound do not actually mix until they are expelled together from the nozzle of the spraying device.

5. Crosslinked Proteins

Described herein are methods for coupling a protein with another molecule using aminooxy ether compounds. In one aspect, a protein having at least one aminooxy-reactive group is reacted with a compound having at least one aminooxy group. In another aspect, a protein having at least one aminooxy group is reacted with a compound having at least one aminooxy-reactive group. In one aspect, the hydrazide-reactive group can be a —COOH group (or the salt or ester thereof), an aldehyde group, or a ketone group. The techniques disclosed in international publication nos. WO 02/06373 A1 and WO 02/090390 A1, which are incorporated by reference in their entireties, can be used in this aspect.

In one aspect, the coupled protein has at least one fragment having the formula XXIII

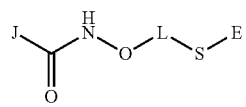

XXIII wherein
J can be any protein residue;
L can be a substituted or unsubstituted hydrocarbyl group, a substituted or unsubstituted heterohydrocarbyl group, a polyalkylene group, a polyether group, a polyamide group, a polyimino group, an aryl group, a polyester, a polythioether group, a polysaccharyl group, or a combination thereof; and
E can be a fluorescent tag, a radiolabel, a targeting moiety, a lipid, a peptide, a radionuclide chelator with a radionuclide, a spin-label, a PEG camouflage, a metal surface, a glass surface, a plastic surface, or a combination thereof.

The protein residue can be any protein that has at least one aminooxy-reactive group or at least one aminooxy group. Any of the protein known in the art capable of being modified with an aminooxy group can be used herein. In one aspect, the protein can be an extracellular matrix protein, a partially hydrolyzed extracellular matrix protein, or a chemically-modified extracellular matrix protein. In another aspect, the protein is collagen, elastin, decorin, laminin, or fibronectin.

In one aspect, E in formula XXIII is a reporter group. Examples of reporter groups include, but are not limited to, a chelated paramagnetic ion for MRI imaging, a $^{18}$F-labelled compound having a thiol-reactive group for positron emission tomography, a fluorescent tag, a radiolabel, a targeting moiety, a lipid, a peptide, a radionuclide chelator with a radionuclide, a spin-label, a PEG camouflage, a glass surface, a plastic surface, or a combination thereof. Examples of spin labels include, but are not limited to, proxyl or doxyl groups. Examples of glass surfaces include, but are not limited to, glass silanized with an epoxy or activated ester or a thiol-reactive electrophilic functional group, beads, or coverslips. Examples of plastics include, but are not limited to, plasma-etched polypropylene or any other plastic material.

In another aspect, described herein is a kit including (1) a compound having at least one aminooxy group; (2) a condensing agent; (3) a buffer reagent; and (4) a purification column. In one aspect, the compound can be any compound having at least one aminooxy group and at least one of the reporter groups described above. Use of the kit generally involves admixing components (1)-(3) together with a protein having at least one aminooxy-reactive group. Components (1)-(3) and the protein can be added in any order. After the protein and the compound having at least one aminooxy group have reacted with one another to produce the coupled protein, the coupled protein is then purified by passing the admixture containing the coupled protein through a purification column. Purification columns and techniques for using the same are known in the art.

B. Pharmaceutical Compositions

In one aspect, any of the compounds, composites, and compositions produced by the methods described above can include at least one bioactive agent defined above that is not covalently attached to the macromolecule. The resulting pharmaceutical composition can provide a system for sustained, continuous delivery of drugs and other biologically-active agents to tissues adjacent to or distant from the application site. The bioactive agent is capable of providing a local or systemic biological, physiological or therapeutic effect in the biological system to which it is applied. For example, the agent can act to control infection or inflammation, enhance cell growth and tissue regeneration, control tumor growth, act as an analgesic, promote anti-cell attachment, and enhance bone growth, among other functions. Additionally, any of the compounds, composites, and compositions described herein can contain combinations of two or more bioactive agents.

In one aspect, the bioactive agents can include substances capable of preventing an infection systemically in the biological system or locally at the defect site, as for example, anti-inflammatory agents such as, but not limited to, pilocarpine, hydrocortisone, prednisolone, cortisone, diclofenac sodium, indomethacin, 6∝-methyl-prednisolone, corticosterone, dexamethasone, prednisone, and the like; antibacterial agents including, but not limited to, penicillin, cephalosporins, bacitracin, tetracycline, doxycycline, gentamycin, chloroquine, vidarabine, and the like; analgesic agents including, but not limited to, salicylic acid, acetaminophen, ibuprofen, naproxen, piroxicam, flurbiprofen, morphine, and the like; local anesthetics including, but not limited to, cocaine, lidocaine, benzocaine, and the like; immunogens (vaccines) for stimulating antibodies against hepatitis, influenza, measles, rubella, tetanus, polio, rabies, and the like; peptides including, but not limited to, leuprolide acetate (an LH-RH agonist), nafarelin, and the like. All compounds are available from Sigma Chemical Co. (Milwaukee, Wis.).

Additionally, a substance or metabolic precursor which is capable of promoting growth and survival of cells and tissues or augmenting the functioning of cells is useful, as for example, a nerve growth promoting substance such as a ganglioside, a nerve growth factor, and the like; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF), interleukin-1 (IL-1), vascular endothelial growth factor (VEGF) and keratinocyte growth factor (KGF), dried bone material, and the like; and antineoplastic agents such as methotrexate, 5-fluorouracil, adriamycin, vinblastine, cisplatin, tumor-specific antibodies conjugated to toxins, tumor necrosis factor, and the like.

Other useful substances include hormones such as progesterone, testosterone, and follicle stimulating hormone (FSH) (birth control, fertility-enhancement), insulin, and the like; antihistamines such as diphenhydramine, and the like; cardiovascular agents such as papaverine, streptokinase and the like; anti-ulcer agents such as isopropamide iodide, and the like; bronchodilators such as metaproternal sulfate, aminophylline, and the like; vasodilators such as theophylline, niacin, minoxidil, and the like; central nervous system agents such as tranquilizer, B-adrenergic blocking agent, dopamine, and the like; antipsychotic agents such as risperidone, narcotic antagonists such as naltrexone, naloxone, buprenorphine; and other like substances. All compounds are available from Sigma Chemical Co. (Milwaukee, Wis.).

The pharmaceutical compositions can be prepared using techniques known in the art. In one aspect, the composition is prepared by admixing a modified or crosslinked macromolecule described herein with a bioactive agent. The term "admixing" is defined as mixing the two components together so that there is no chemical reaction or physical interaction. The term "admixing" also includes the chemical reaction or physical interaction between the compound and the pharmaceutically-acceptable compound. Covalent bonding to reactive therapeutic drugs, e.g., those having reactive carboxyl groups, can be undertaken on the compound. For example, first, carboxylate-containing chemicals such as anti-inflammatory drugs ibuprofen or hydrocortisone-hemisuccinate can be converted to the corresponding N-hydroxysuccinimide (NHS) active esters and can further react with the $NH_2$ group of the dihydrazide-modified polysaccharide. Second, noncovalent entrapment of a bioactive agent in any of the compounds, composites, and compositions described herein is also possible. Third, electrostatic or hydrophobic interactions can facilitate retention of a bioactive agent in the compound, composite, and composition described herein. For example, the hydrazido group can non-covalently interact, e.g., with carboxylic acid-containing steroids and their analogs, and anti-inflammatory drugs such as Ibuprofen (2-(4-iso-butylphenyl) propionic acid). The protonated hydrazido group can form salts with a wide variety of anionic materials such as proteins, heparin or dermatan sulfates, oligonucleotides, phosphate esters, and the like.

It will be appreciated that the actual preferred amounts of bioactive compound in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

Pharmaceutical compositions described herein can be formulated in any excipient the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally).

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates.

In one aspect, any of the compounds, composites, and compositions described herein can include living cells. Examples of living cells include, but are not limited to, fibroblasts, hepatocytes, chondrocytes, stem cells, bone marrow, muscle cells, cardiac myocytes, neuronal cells, or pancreatic islet cells.

C. Methods of Use

Any of the compounds, composites, compositions, and methods described herein can be used for a variety of uses related to drug delivery, small molecule delivery, wound healing, burn injury healing, and tissue regeneration. The disclosed compounds, composites, compositions, and methods are useful for situations which benefit from a hydrated, pericellular environment in which assembly of other matrix components, presentation of growth and differentiation factors, cell migration, or tissue regeneration are desirable.

The compounds, composites, and compositions described herein can be placed directly in or on any biological system without purification as it is composed of biocompatible materials. Examples of sites the compounds, composites, and compositions can be placed include, but not limited to, soft tissue such as muscle or fat; hard tissue such as bone or cartilage; areas of tissue regeneration; a void space such as periodontal pocket; surgical incision or other formed pocket or cavity; a natural cavity such as the oral, vaginal, rectal or nasal cavities, the cul-de-sac of the eye, and the like; the peritoneal cavity and organs contained within, and other sites into or onto which the compounds can be placed including a skin surface defect such as a cut, scrape or burn area. Alternatively, the compounds, composites, and compositions described herein can be used to extend the viability of damaged skin. The compounds, composites, and compositions described herein can be biodegradable and naturally occurring enzymes will act to degrade them over time. Components of the compounds, composites, and compositions can be "bioabsorbable" in that the components of the compounds, composites, and compositions will be broken down and absorbed within the biological system, for example, by a cell, tissue and the like. Additionally, the compounds, composites, and compositions, especially the compounds, composites, and compositions that have not been rehydrated, can be applied to a biological system to absorb fluid from an area of interest.

The compounds, composites, and compositions described herein can be used in a number of different surgical procedures. In one aspect, the compounds, composites, and compositions can be used in any of the surgical procedures disclosed in U.S. Pat. Nos. 6,534,591 B2 and 6,548,081 B2, which are incorporated by reference in their entireties. In one aspect, the compounds, composites, and compositions described herein can be used in cardiosurgery and articular surgery; abdominal surgery where it is important to prevent adhesions of the intestine or the mesentery; operations performed in the urogenital regions where it is important to ward off adverse effects on the ureter and bladder, and on the functioning of the oviduct and uterus; and nerve surgery operations where it is important to minimize the development of granulation tissue. In surgery involving tendons, there is generally a tendency towards adhesion between the tendon and the surrounding sheath or other surrounding tissue during the immobilization period following the operation. In another aspect, the compounds, composites, and compositions described herein can be used to prevent adhesions after laparascopic surgery, pelvic surgery, oncological surgery, sinus and craniofacial surgery, ENT surgery, or in procedures involving spinal dura repair.

In another aspect, the compounds, composites, and compositions can be used in ophthalmological surgery. In ophthalmological surgery, a biodegradable implant could be applied in the angle of the anterior chamber of the eye for the purpose of preventing the development of synechiae between the cornea and the iris; this applies especially in cases of reconstructions after severe damaging events. Moreover, degradable or permanent implants are often desirable for preventing adhesion after glaucoma surgery and strabismus surgery.

In another aspect, the compounds, composites, and compositions can be used in the repair of tympanic membrane perforations (TMP). The tympanic membrane (TM) is a three-layer structure that separates the middle and inner ear from the external environment. These layers include an outer ectodermal portion composed of keratinizing squamous epithelium, an intermediate mesodermal fibrous component and an inner endodermal mucosal layer. This membrane is only 130 μm thick but provides important protection to the middle and inner ear structures and auditory amplification.

TMP is a common occurrence usually attributed to trauma, chronic otitis media or from PE tube insertion. Blunt trauma resulting in a longitudinal temporal bone fracture is classically associated with TMP. More common causes include a slap to the ear and the ill-advised attempt to clean an ear with a cotton swab (Q-tip™) or sharp instrument.

Any of the compounds, composites, and compositions described herein can be administered through the tympanic membrane without a general anesthetic and still provide enhanced wound healing properties. In one aspect, the compounds, composites, and compositions can be injected through the tympanic membrane using a cannula connected to syringe.

In another aspect, the compounds, composites, and compositions described herein can be used as a postoperative wound barrier following endoscopic sinus surgery. Success in functional endoscopic sinus surgery (FESS) is frequently limited by scarring, which narrows or even closes the surgically widened openings. Spacers and tubular stents have been used to temporarily maintain the opening, but impaired wound healing leads to poor long-term outcomes. The use of any compounds, composites, and compositions described herein can significantly decrease scar contracture following maxillary sinus surgery.

In another aspect, the compounds, composites, and compositions described herein can be used for the augmentation of soft or hard tissue. In another aspect, the compounds, composites, and compositions described herein can be used to coat articles such as, for example, a surgical device, a prosthetic, or an implant (e.g., a stent). In another aspect, the compounds, composites, and compositions described herein can be used to treat aneurisms.

The compounds, composites, and compositions described herein can be used as a carrier and delivery device for a wide variety of releasable bioactive agents having curative or therapeutic value for human or non-human animals. Any of the bioactive agents described above can be used in this aspect. Many of these substances which can be carried by the compounds, composites, and compositions are discussed above.

Depending upon the selection of the bioactive agent, the bioactive agent can be present in the first compound or the prohealing compound. Included among pharmaceutically-acceptable compounds that are suitable for incorporation into the compounds, composites, and compositions described herein are therapeutic drugs, e.g., anti-inflammatory agents, anti-pyretic agents, steroidal and non-steroidal drugs for anti-inflammatory use, hormones, growth factors, contraceptive agents, antivirals, antibacterials, antifungals, analgesics, hypnotics, sedatives, tranquilizers, anti-convulsants, muscle relaxants, local anesthetics, antispasmodics, antiulcer drugs, peptidic agonists, sympathiomimetic agents, cardiovascular agents, antitumor agents, oligonucleotides and their analogues and so forth. The pharmaceutically-acceptable compound is added in pharmaceutically active amounts.

The rate of drug delivery depends on the hydrophobicity of the molecule being released. For example, hydrophobic molecules, such as dexamethazone and prednisone are released slowly from the compound as it swells in an aqueous environment, while hydrophilic molecules, such as pilocarpine, hydrocortisone, prednisolone, cortisone, diclofenac sodium, indomethacin, 6α-methyl-prednisolone and corticosterone, are released quickly. The ability of the compound to maintain a slow, sustained release of steroidal anti-inflammatories makes the compounds described herein extremely useful for wound healing after trauma or surgical intervention.

In certain methods the delivery of molecules or reagents related to angiogenesis and vascularization are achieved. Disclosed are methods for delivering agents, such as VEGF, that stimulate microvascularization. Also disclosed are methods for the delivery of agents that can inhibit angiogenesis and vascularization, such as those compounds and reagents useful for this purpose disclosed in but not limited to U.S. Pat. Nos. 6,174,861 for "Methods of inhibiting angiogenesis via increasing in vivo concentrations of endostatin protein;" 6,086,865 for "Methods of treating angiogenesis-induced diseases and pharmaceutical compositions thereof;" 6,024,688 for "Angiostatin fragments and method of use;" 6,017,954 for "Method of treating tumors using O-substituted fumagillol derivatives;" 5,945,403 for "Angiostatin fragments and method of use;" 5,892,069 "Estrogenic compounds as anti-mitotic agents;" for 5,885,795 for "Methods of expressing angiostatic protein;" 5,861,372 for "Aggregate angiostatin and method of use;" 5,854,221 for "Endothelial cell proliferation inhibitor and method of use;" 5,854,205 for "Therapeutic antiangiogenic compositions and methods;" 5,837,682 for "Angiostatin fragments and method of use;" 5,792,845 for "Nucleotides encoding angiostatin protein and method of use;" 5,733,876 for "Method of inhibiting angiogenesis;" 5,698,586 for "Angiogenesis inhibitory agent;" 5,661,143 for "Estrogenic compounds as anti-mitotic agents;" 5,639,725 for "Angiostatin protein;" 5,504,074 for "Estrogenic compounds as anti-angiogenic agents;" 5,290,807 for "Method for regressing angiogenesis using o-substituted fumagillol derivatives;" and 5,135,919 for "Method and a pharmaceutical composition for the inhibition of angiogenesis" which are herein incorporated by reference for the material related to molecules for angiogenesis inhibition.

In one aspect, the pharmaceutically-acceptable compound is pilocarpine, hydrocortisone, prednisolone, cortisone, diclofenac sodium, indomethacin, 6∝-methyl-prednisolone, corticosterone, dexamethasone and prednisone. However, methods are also provided wherein delivery of a pharmaceutically-acceptable compound is for a medical purpose selected from the group of delivery of contraceptive agents, treating postsurgical adhesions, promoting skin growth, preventing scarring, dressing wounds, conducting viscosurgery, conducting viscosupplementation, engineering tissue.

In one aspect, the compounds, composites, and compositions described herein can be used for the delivery of living cells to a subject. Any of the living cells described above can be used in the aspect. In one aspect, the living cells are part of the prohealing compound. For example, when the composite is a laminate, the living cells are present in the prohealing layer. In another aspect, the compounds, composites, and compositions described herein can be used to support the growth of a variety of cells including, but not limited to, tumor cells, fibroblasts, chondrocytes, stem cells (e.g., embryonic, preadipocytes, mesenchymal, cord blood derived, bone marrow), epithelial cells (e.g., breast epithelial cells, intestinal epithelial cells), cells from neural lineages (e.g., neurons, astrocytes, oligodendrocytes, and glia), cells derived from the liver (e.g., hepatocytes), endothelial cells (e.g., vascular endothelial), cardiac cells (e.g., cardiac myocytes), muscle cells (e.g., skeletal or vascular smooth muscle cells), or osteoblasts. Alternatively, cells may be derived from cell lines or a primary source (e.g., human or animal), a biopsy sample, or a cadaver.

In one aspect, the compounds, composites, and compositions can be used for the delivery of growth factors and molecules related to growth factors. Any of the growth factors described above are useful in this aspect. In one aspect, the growth factor is part of the prohealing compound.

In one aspect, described herein are methods for reducing or inhibiting adhesion of two tissues in a surgical wound in a subject by contacting the wound of the subject with any of the compounds, composites, and compositions described herein. Not wishing to be bound by theory, it is believed that the first compound will prevent tissue adhesion between two different tissues (e.g., organ and skin tissue). It is desirable in certain post-surgical wounds to prevent the adhesion of tissues in order to avoid future complications. The second layer and optional third layer will promote healing of the tissues.

In another aspect, when the composite is laminate, the laminate includes a first layer of anti-adhesion compound/support and a second layer composed of a prohealing compound, wherein the laminate is wrapped around a tissue. For example, the laminate can be wrapped around a tendon, where the first layer is in contact with the tendon, and the second layer is in contact with surrounding muscle tissue. In this aspect, the laminate contributes a cylindrical anti-adhesion layer around the tendon, while healing of the tendon is promoted by the inner layer of the cylindrical material.

The compounds, composites, and compositions described herein provide numerous advantages. For example, the composites provide a post-operative adhesion barrier that is at least substantially resorbable and, therefore, does not have to be removed surgically at a later date. Another advantage is that the compounds, composites, and compositions are also relatively easy to use, are capable of being sutured, and tend to stay in place after it is applied.

In another aspect, described herein are methods for improving wound healing in a subject in need of such improvement by contacting any of the compounds, composites, and compositions described herein with a wound of a subject in need of wound healing improvement. Also provided are methods to deliver at least one bioactive agent to a patient in need of such delivery by contacting any of the compounds, composites, and compositions described herein with at least one tissue capable of receiving said bioactive agent.

The disclosed compounds, composites, and compositions can be used for treating a wide variety of tissue defects in an animal, for example, a tissue with a void such as a periodontal pocket, a shallow or deep cutaneous wound, a surgical incision, a bone or cartilage defect, bone or cartilage repair, vocal fold repair, and the like. For example, the compounds, composites, and compositions described herein can be in the form of a hydrogel film. The hydrogel film can be applied to a defect in bone tissue such as a fracture in an arm or leg bone, a defect in a tooth, a cartilage defect in the joint, ear, nose, or throat, and the like. The hydrogel film composed of the compounds, composites, and compositions described herein can also function as a barrier system for guided tissue regeneration by providing a surface on or through which the cells can grow. To enhance regeneration of a hard tissue such as bone tissue, it is preferred that the hydrogel film provides support for new cell growth that will replace the matrix as it becomes gradually absorbed or eroded by body fluids.

The compounds, composites, and compositions described herein can be delivered onto cells, tissues, and/or organs, for example, by injection, spraying, squirting, brushing, painting, coating, and the like. Delivery can also be via a cannula, catheter, syringe with or without a needle, pressure applicator, pump, and the like. The compounds, composites, and compositions described herein can be applied onto a tissue in the form of a film, for example, to provide a film dressing on the surface of the tissue, and/or to adhere to a tissue to another tissue or hydrogel film, among other applications.

In one aspect, the compounds, composites, and compositions described herein are administered via injection. For many clinical uses, when the compounds and composites are in the form of a hydrogel film, injectable hydrogels are preferred for three main reasons. First, an injectable hydrogel could be formed into any desired shape at the site of injury. Because the initial hydrogels can be sols or moldable putties, the systems can be positioned in complex shapes and then subsequently crosslinked to conform to the required dimensions. Second, the hydrogel would adhere to the tissue during gel formation, and the resulting mechanical interlocking arising from surface microroughness would strengthen the tissue-hydrogel interface. Third, introduction of an in situ-crosslinkable hydrogel could be accomplished using needle or by laparoscopic methods, thereby minimizing the invasiveness of the surgical technique.

The compounds, composites, and compositions described herein can be used to treat periodontal disease, gingival tissue overlying the root of the tooth can be excised to form an envelope or pocket, and the composition delivered into the pocket and against the exposed root. The compounds, composites, and compositions can also be delivered to a tooth defect by making an incision through the gingival tissue to expose the root, and then applying the material through the incision onto the root surface by placing, brushing, squirting, or other means.

When used to treat a defect on skin or other tissue, the compounds, composites, and compositions described herein can be in the form of a hydrogel film that can be placed on top of the desired area. In this aspect, the hydrogel film is malleable and can be manipulated to conform to the contours of the tissue defect.

The compounds, composites, and compositions described herein can be applied to an implantable device such as a suture, claps, stents, prosthesis, catheter, metal screw, bone plate, pin, a bandage such as gauze, and the like, to enhance the compatibility and/or performance or function of an implantable device with a body tissue in an implant site. The compounds, composites, and compositions can be used to coat the implantable device. For example, the compounds, composites, and compositions could be used to coat the rough surface of an implantable device to enhance the compatibility of the device by providing a biocompatible smooth surface which reduces the occurrence of abrasions from the contact of rough edges with the adjacent tissue. The compounds, composites, and compositions can also be used to enhance the performance or function of an implantable device. For example, when the compounds, composites, and compositions are a hydrogel film, the hydrogel film can be applied to a gauze bandage to enhance its compatibility or adhesion with the tissue to which it is applied. The hydrogel film can also be applied around a device such as a catheter or colostomy that is inserted through an incision into the body to help secure the catheter/colostomy in place and/or to fill the void between the device and tissue and form a tight seal to reduce bacterial infection and loss of body fluid.

In one aspect, the aminooxy-derivatized polymers such as, for example, pluronics, can couple to GAGs such as, for example, hyaluronan or heparin, and self-assemble into hydrogels. Alternatively, solutions of aminooxy derivatized polymer-GAGs can be coated on a hydrophobic surface such as, for example, a medical device. For example, heparin can be coupled with an aminooxy-derivatized pluronic, wherein the resultant gel possesses desirable growth-binding factor capabilities but does not possess anti-coagulant properties associated with heparin. Not wishing to be bound by theory, the pluoronic portion of the hydrogel can prevent coagulation, which is undesirable side-effect of heparin. In one aspect, aminooxy derivatized polymer-hyaluronan can prevent biofilm formation on a surface because hyaluronan can block bacterial adhesion to the surface of a device.

It is understood that the disclosed compounds, composites, and compositions can be applied to a subject in need of tissue regeneration. For example, cells can be incorporated into the composites described herein for implantation. Examples of subjects that can be treated with the compounds, composites, and compositions described herein include mammals such as mice, rats, cows or cattle, horses, sheep, goats, cats, dogs, and primates, including apes, chimpanzees, orangutans, and humans. In another aspect, the compounds, composites, and compositions described herein can be applied to birds.

When being used in areas related to tissue regeneration such as wound or burn healing, it is not necessary that the disclosed compounds, composites, and compositions, and methods eliminate the need for one or more related accepted therapies. It is understood that any decrease in the length of time for recovery or increase in the quality of the recovery obtained by the recipient of the disclosed compounds, composites, and compositions, and methods has obtained some benefit. It is also understood that some of the disclosed compounds, composites, and compositions, and methods can be used to prevent or reduce fibrotic adhesions occurring as a result of wound closure as a result of trauma, such surgery. It is also understood that collateral affects provided by the disclosed compounds, composites, and compositions, and methods are desirable but not required, such as improved bacterial resistance or reduced pain etc.

In one aspect, the compounds or compositions described herein can be used to prevent airway stenosis. Subglottic stenosis (SGS) is a condition affecting millions of adults and children world-wide. Causes of acquired SGS range from mucosal injury of respiratory epithelia to prolonged intubation. Known risk factors of SGS in intubated patients include prolonged intubation, high-pressure balloon cuff, oversized endotracheal (ET) tube, multiple extubations or re-intubations, and gastro-esophageal reflux. There are also individuals in whom stenosis develops as a result of surgery, radiation, autoimmune disease, tumors, or other unexplained reasons.

While very diverse, the etiologies of SGS all have one aspect in common, narrowing of the airway resulting in obstruction. This narrowing most commonly occurs at the level of the cricoid cartilage due to its circumferential nature and rigidity. Such etiologies have been found in various SGS models: activation of chondrocytes and formation of fibrous scar, infiltration of polymorphonuclear leukocytes and chronic inflammatory cells with squamous metaplasia, and morphometric changes in airway lumen. Each presents a problem requiring immediate attention.

In another aspect, any of the compounds or compositions described herein can be used as a 3-D cell culture. In one aspect, the hydrogel can be lyophilized to create a porous sponge onto which cells may be seeded for attachment, proliferation, and growth. It is contemplated that miniarrays and microarrays of 3-D hydrogels or sponges can be created on surfaces such as, for example, glass, and the resulting gel or sponge can be derived from any of the compounds or compositions described herein. The culture can be used in numerous embodiments including, but not limited to, determining the efficacy or toxicity of experimental therapeutics.

It is understood that any given particular aspect of the disclosed compositions and methods can be easily compared to the specific examples and embodiments disclosed herein, including the non-polysaccharide based reagents discussed in the Examples. By performing such a comparison, the relative efficacy of each particular embodiment can be easily determined. Particularly preferred assays for the various uses are those assays which are disclosed in the Examples herein, and it is understood that these assays, while not necessarily limiting, can be performed with any of the compositions and methods disclosed herein.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

I. Synthesis of Carboxymethyl Derivatives of Hyaluronan
1. Materials

Fermentation-derived hyaluronan (HA, sodium salt, $M_w$ 1.5 MDa) was purchased from Clear Solutions Biotechnology, Inc. (Stony Brook, N.Y.). 1-Ethyl-3-[3-(dimethylamino) propyl]carbodiimide (EDCI), and chloroacetic acid were purchased from Aldrich Chemical Co. (Milwaukee, Wis.). Poly (ethylene glycol)diacrylate (Mw 3400 Da) was purchased from Nektar Therapeutics (formerly Shearwater) (Huntsville, Ala.). Dulbecco's phosphate buffered saline (DPBS), cysteine and bovine testicular hyaluronidase (HAse, 330 U/mg) was obtained from Sigma Chemical Co. (St. Louis, Mo.). Dithiothreitol (DTT) was purchased from Diagnostic Chemical Limited (Oxford, Conn.). 3,3'-Dithiobis(propanoic dihydrazide) (DTP) was synthesized as described before. (Vercruysse, K. P.; Marecak, D. M.; Marecek, J. F.; Prestwich, G. D. Synthesis and in vitro degradation of new polyvalent hydrazide cross-linked hydrogels of hyaluronic acid. *Bioconjugate Chem.* 1997, 8, 686-694; Shu, X. Z.; Liu, Y.; Luo, Y.; Roberts, M. C.; Prestwich, G. D. Disulfide crosslinked hyaluronan hydrogels. *Biomacromolecules* 2002, 3, 1304-β11).

2. Analytical Instrumentation

Proton NMR spectral data were obtained using a Varian NOVA 400 at 400 MHz. UV-vis spectral data were recorded using a Hewlett Packard 8453 UV-visible spectrophotometer (Palo Alto, Calif.). Gel permeation chromatography (GPC) analysis was performed using the following system: Waters 515 HPLC pump, Waters 410 differential refractometer, Waters™ 486 tunable absorbance detector, Ultrahydrogel 250 or 1000 columns (7.8 mm i.d.×130 cm) (Milford, Mass.). The eluent was 200 mM phosphate buffer (pH 6.5): MeOH=80:20 (v/v) and the flow rate was either 0.3 or 0.5 ml/min. The system was calibrated with standard HA samples provided by Dr. U. Wik (Pharmacia, Uppsala, Sweden). Fluorescence images of viable cells were recorded using confocal microscopy (LSM 510 Carl Zeiss Microimaging, Inc., Thornwood, N.Y.). Cell proliferation was determined by MTS assay at 550 nm, which was recorded on an OPTImax microplate reader (Molecular Devices, Sunnyvale, Calif.).

Figure 5:
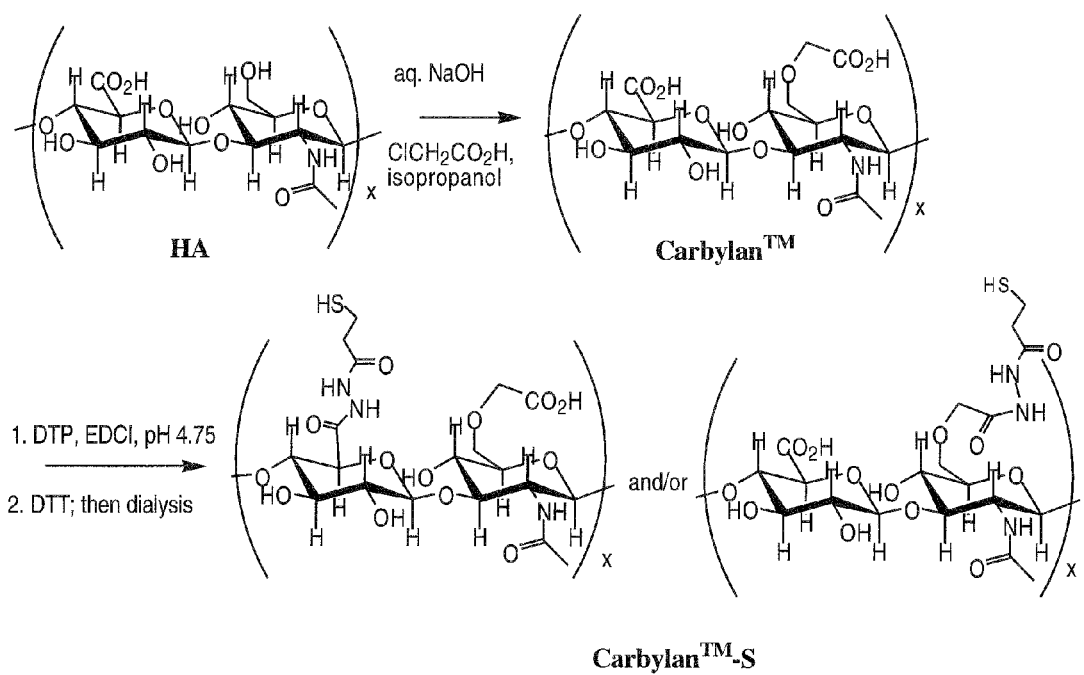
FIG. 5 shows a reaction scheme for producing carboxymethylhyaluronan (Carbylan™) and thiolated hydrazide-modified carboxymethylhyaluronan (Carbylan™-S).

3. Synthesis of Carboxymethyl-HA (CM-HA or Carbylan™) (FIG. 5)

HA powder (20 g) was added to a 500-ml beaker. Aqueous NaOH solution (200 ml, 45% w/v) was added to the beaker and stirred mechanically (with a spatula) at ambient temperature until a paste formed, which takes about 5 minutes or less for the paste to form. After standing for 2 hours, the HA paste was transferred into a 5,000-ml beaker with 1,500 ml isopropanol and a Teflon-coated magnetic stir bar, and then a solution of 20 g of chloroacetic acid in 500 ml isopropanol was added with magnetic stirring. After 1 hour stirring at ambient temperature, the product was collected by filtration using a paper filter in a porcelain filter. The beaker was washed with a small amount of isopropanol to recover the modified pasty product. The crude filtrate was then dissolved in 2,000 ml of distilled water. The solution pH was adjusted to ca. pH 7.0 by adding 6.0 N HCl. Next, the solution was purified by dialysis (dialysis tubing, Mw cutoff 3,500) extensively (currently 2 days, with 8 changes of outside water solution) and then lyophilized to give solid white Carbylan™ (ca. 15 g) as a white foam.

4. Synthesis of Carboxymethyl-HA (CM-HA-DTPH or Carbylan™-S) (FIG. 5)

HA powder (20 g) was added to a 500-ml beaker. Aqueous NaOH solution (200 ml, 45% w/v) was added to the beaker and stirred mechanically (with a spatula) at ambient temperature until a paste formed, which takes about 5 minutes or less for the paste to form. After standing for 2 hours, the HA paste was transferred into a 5,000-ml beaker with 1,500 ml isopropanol and a Teflon-coated magnetic stir bar, and then a solution of 20 g of chloroacetic acid in 500 ml isopropanol was added with magnetic stirring. After 1 hour stirring at ambient temperature, the product was collected by filtration using a paper filter in a porcelain filter. The beaker was washed with isopropanol to recover the product. The crude filtrate was then dissolved in 2,000 ml of distilled water. The solution pH was adjusted to ca. pH 7.0 by adding 6.0 N HCl. Next, the solution was purified by dialysis (dialysis tubing, Mw cutoff 3,500) for 24 h with 4 changes of water.

The dialyzed solution of Carbylan™ can be used directly in following step, or can be degraded to lower molecular weight as described below. (Optional—acid degradation to reduce molecular weight) The purified solution was transferred into a 5000-ml beaker, and then 80 ml of 6.0 N HCl was added and the solution was stirred magnetically at room temperature. Then, the mixture was transferred to an rotary incubator (37° C., 150 rpm) for defined time. Typically, 24 h of stirring under these conditions would afford Carbylan™ with approximately 100-150 kDa molecular weight.

DTP (16.7 g, 0.07 mol) was added to the Carbylan™ solution, and the solution pH was adjusted to 4.75 by adding either HCl or NaOH solution. Then, 6.72 g (0.035 mol) EDCI was added, and the solution pH was maintained at a pH of 4.75 by adding 1.0 N HCl with continuous magnetic stirring at room temperature. After 4 h, 50 g of DTT was added, and the solution pH was adjusted to 8.5 by adding conc. NaOH solution. Then after 12-24 h under magnetic stirring at room temperature, the pH of the reaction mixture was adjusted to pH 3.5 by the addition of 1.0 N HCl. The acidified solution was transferred to dialysis tubing ($M_w$ cut-off 3,500) and dialyzed exhaustively against dilute HCl (pH 3.5) containing 100 mM NaCl, followed by dialysis against dilute HCl, pH 3.5. The solution was then centrifuged, and the supernatant was lyophilized to give solid white Carbylan™-S (ca. 13 g).

Figure 6:
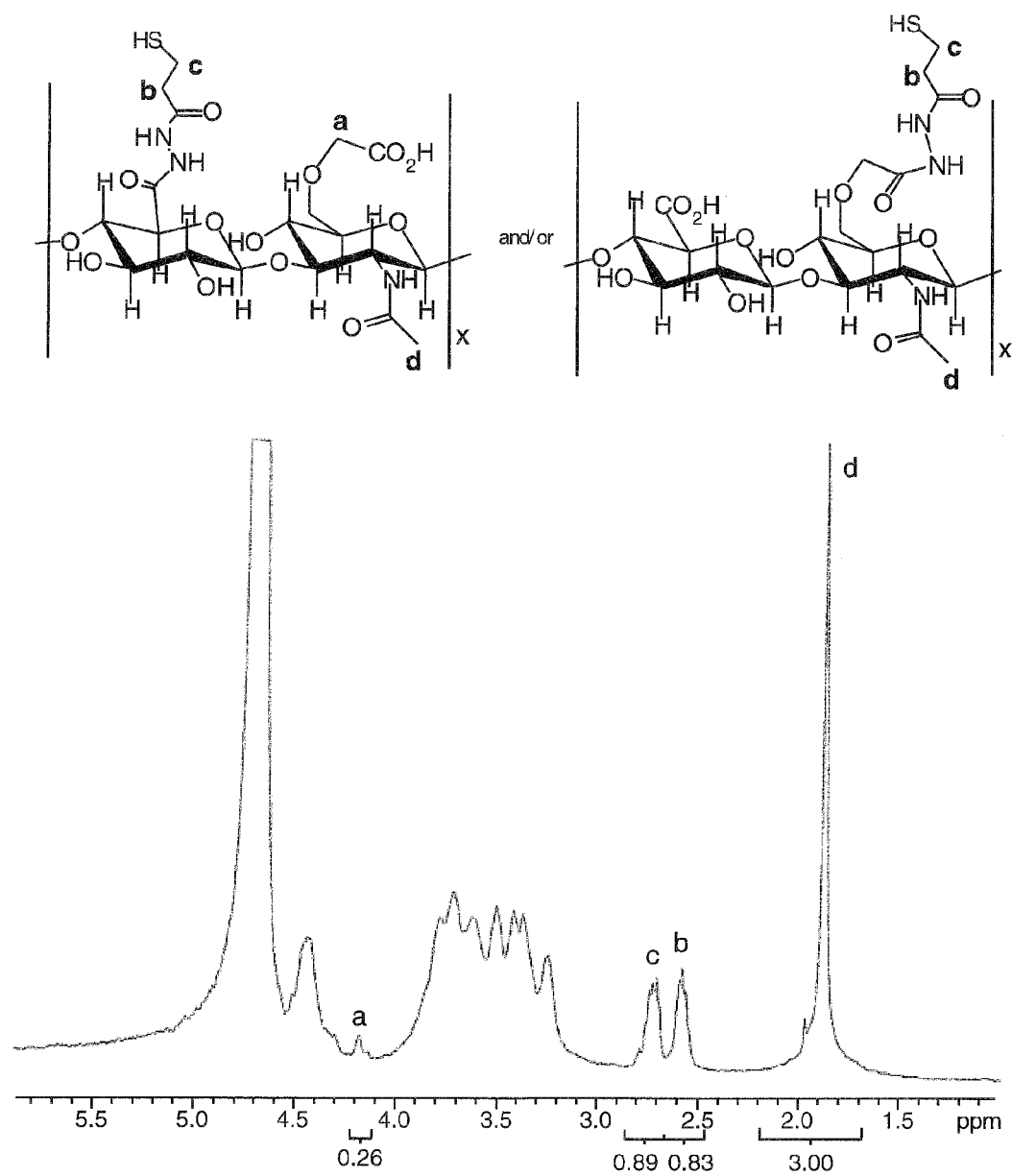
FIG. 6 shows the $^1$H NMR spectrum of Carbylan™-S.

5. Characterization of Carbylan™ and Carbylan™-S a. $^1$H NMR Spectra in $D_2O$ of Carbylan™ and Carbylan™-S Carbylan™ and Carbylan™-S were dissolved in $D_2O$, and $^1$H-NMR spectral data were obtained using a Varian INOVA 400 at 400 MHz. Compared to the spectrum of HA (the N-acetyl methyl protons of HA were at δ 1.95), new resonance for Carbylan™ appeared at δ 4.05-4.20, corresponding to the side chain methylene ($CH_2OCH_2COO^-Na^+$). Another two new resonances for Carbylan™-S appeared at δ 2.72 and δ 2.58, which correspond to the two side chain methylenes in the DTPH modification ($CH_2CH_2SH$) (FIG. 6).

b. Determination of In Vitro Cytotoxicity of Carbylan™ and Carbylan™-S

Figure 7A:
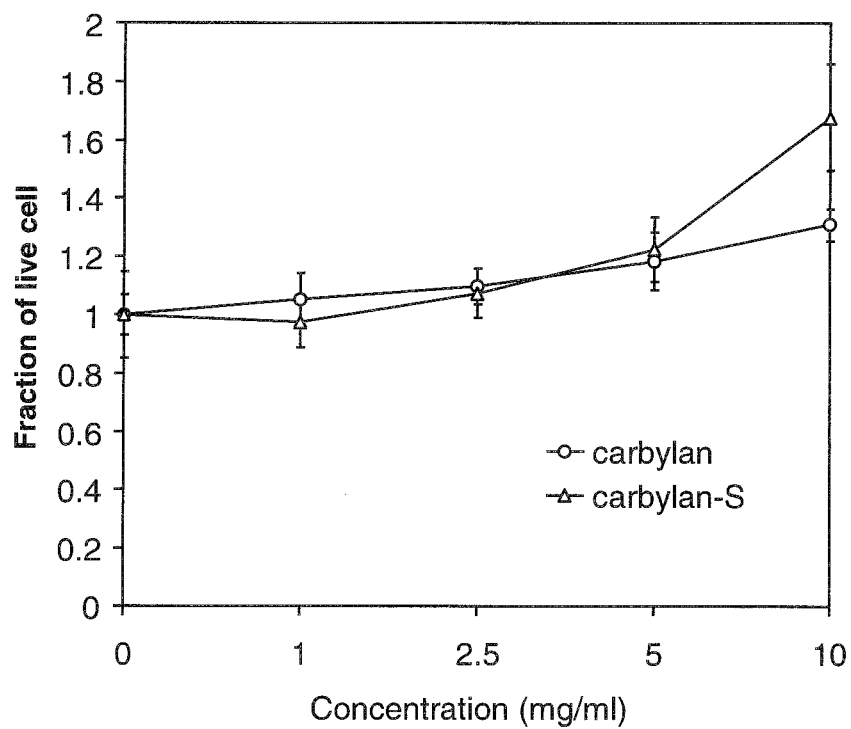
FIGS. 7A and 7B show the cytotoxicity of Carbylan™ (open circles) and Carbylan™-S (open triangles) using an MTS assay (n=6), where FIG. 7A corresponds to after 2 hours of culturing and FIG. 7B corresponds to after 24 hours of culturing.
Figure 7B:
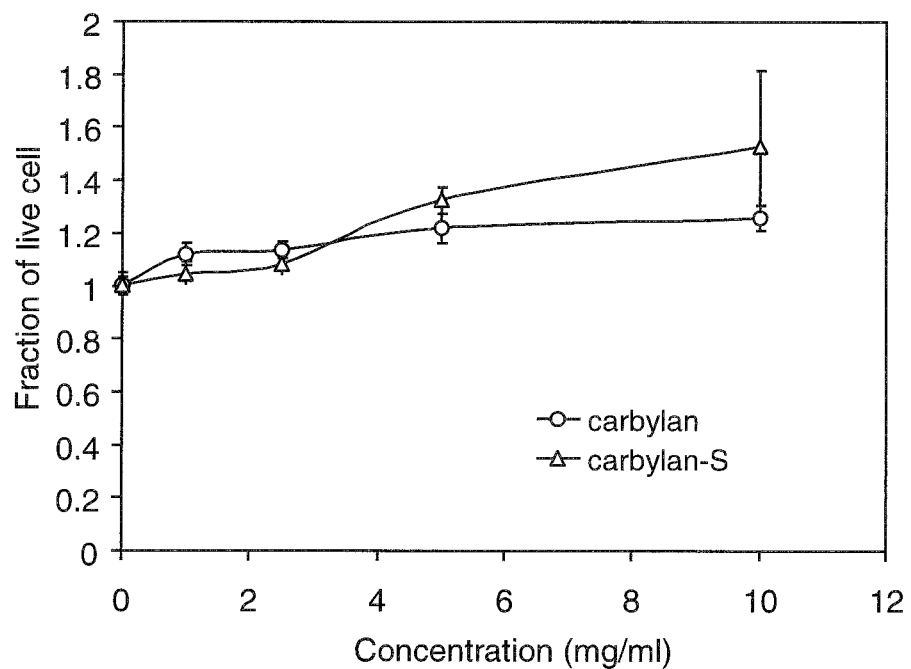

Carbylan™ and Carbylan™-S were dissolved in complete DMEM/F-12 medium supplemented with 10% new-born calf serum, 2 mM L-glutamine and 100 units/ml antibotic-antimycotic (GIBCO BRL, Life Technologies, Grand Island, N.Y.), to give 1, 2.5, 5 and 10 mg/ml solutions. NIH 3T3 fibroblast was cultured in 96-well plate for 24 h (5,000 cells/well), then 0.2 ml above solutions were added into each well. After culture in vitro for 2 and 24 h, the live cell count was determined using the CyQUANT™ cell proliferation assay and MTS assay (FIGS. 7A and 7B).

The CyQUANT™ cell proliferation assay is a cellular nucleic acid determination method, which is linear with the density of cells in culture. This assay revealed that that Carbylan™ and Carbylan™-S are fully cytocompatible. That is, the cell density after culturing fibroblasts in medium containing 1 mg/ml, 2.5 mg/ml, 5 mg/ml and 10 mg/ml of either Carbylan™ or Carbylan™-S is comparable to that for cells cultured in the control medium (results not shown). The MTS assay is a colorimetric method for determining the number of viable cells in culture. In this assay, a tetrazolium salt (MTS) becomes reduced by the mitochondria of living cells into a colored formazan product, the presence of which can be detected with a spectrophotometer. The results in FIG. 7 indicated that Carbylan™ and Carbylan™-S are fully cytocompatible; indeed, they may even enhance mitochondrial function.

c. Carbylan™-S Gelation in Air 2 mL each of high, medium and low molecular weight Carbylan-S at a concentration of 1.25% were used as starting materials. Through a series of dilutions, 300 µL of 4 different concentrations (1.25%, 0.625%, 0.3125% and 0.15625%) were tested for time to gelation in air (without a crosslinker). The fields marked with a time in Tables 3-5 are the time at which the material formed a gel. The fields with no time recorded are the materials that have not yet formed a gel. Carbylan-S at the 0.3125% and 0.15625% concentrations for all three molecular weights was tested for gelation at pH 5.5. None of these materials have formed a gel yet.

TABLE 3

(25° C.; pH 7.4)

| 1.25% hmw Carbylan-S | 0.625% hmw Carbylan-S | 0.3125% hmw Carbylan-S | 0.15625% hmw Carbylan-S |
|---|---|---|---|
| II. 8 Hours | III. 22 Hours | IV. 42 Hours | V. No Gel Formation |
| 1.25% mmw Carbylan-S | 0.625% mmw Carbylan-S | 0.3125% mmw Carbylan-S | 0.15625% mmw Carbylan-S |
| VI. 36 Hours | VII. 57 Hours | VIII. 153 Hours | No Gel Formation |
| 1.25% lmw Carbylan-S | 0.625% lmw Carbylan-S | 0.3125% lmw Carbylan-S | 0.15625% lmw Carbylan-S |
| IX. 63 Hours | X. 131 Hours | XI. 244 Hours | No Gel Formation |

TABLE 4

(37° C.; pH 6.5)

| 1.25% hmw Carbylan-S | 0.31% hmw Carbylan-S | 0.125% hmw Carbylan-S | 0.031% hmw Carbylan-S |
|---|---|---|---|
| XII. 77 Hours | XIII. 103 Hours | No Gel Formation | No Gel Formation |
| 1.25% mmw Carbylan-S | 0.31% mmw Carbylan-S | 0.125% mmw Carbylan-S | 0.031% mmw Carbylan-S |
| XIV. 128 Hours | 114 Hours | No Gel Formation | No Gel Formation |
| 1.25% lmw Carbylan-S | 0.31% lmw Carbylan-S | 0.125% lmw Carbylan-S | 0.031% lmw Carbylan-S |
| 222 Hours | 279 Hours | No Gel Formation | No Gel Formation |

TABLE 5

(37° C.; pH 5.5)

| 1.25% hmw Carbylan-S | 0.31% hmw Carbylan-S | 0.125% hmw Carbylan-S | 0.031% hmw Carbylan-S |
|---|---|---|---|
| XV. 279 Hours | XVI. 307 Hours | No Gel Formation | No Gel Formation |
| 1.25% mmw Carbylan-S | 0.31% mmw Carbylan-S | 0.125% mmw Carbylan-S | 0.031% mmw Carbylan-S |
| XVII. 291 Hours | 322 Hours | No Gel Formation | No Gel Formation |
| 1.25% lmw Carbylan-S | 0.31% lmw Carbylan-S | 0.125% lmw Carbylan-S | 0.031% lmw Carbylan-S |
| XVIII. >400 Hours | >400 Hours | No Gel Formation | No Gel Formation |

6. Crosslinking of Carbylan™-S and Gelatin-DTPH with Pegda to Give Carbylan™-SX and Carbylan™-GSX (FIG. 8)

Hydrogels (Carbylan™-SX) were formed by Michael-type conjugate addition of Carbylan™-S to poly(ethylene glycol) diacrylate PEGDA using techniques described in International Patent Application Publication No. WO 2004/037,164, which is incorporated by reference in its entirety. The gelation time depends primarily on the concentration of Carbylan™-S and PEGDA, the thiol:acrylate ratio, and the pH. By optimizing these parameters, Carbylan™-SX can be formulated as an in situ-crosslinking injectable product for a variety of medical applications. Carbylan™-GSX was produced by reacting Carbylan™-S, gelatin-DTPH, and PEGDA (FIG. 8). The linker as labeled in FIG. 8 is derived from PEGDA.

a. Dynamic Mechanical Properties of Carbylan™-SX

Gelation of hydrogels with varying linker lengths, crosslinking ratios and concentrations was quantitatively examined using dynamic rheology (Model AR550; TA Instruments; New Castle, Del.) according to ASTM D4473-01. The response of the hydrogel to the applied stress was measured and the storage modulus (G'), loss modulus (G") and dynamic viscosity (η*) were examined over time. Gel point was defined as the time at which the storage modulus (G') and loss modulus (G") curves cross and where there is a dramatic increase in complex viscosity, representing a change in hydrogel behavior from more viscous to more elastic (Peter, Kim et al. 1999; Nowak, Breedveld et al. 2002; Au, Ha et al. 2003). For this study, a parallel plate set up was used with 20 mm diameter plates and a 0.8 mm gap. The Carbylan™-S and PEDGA were vortex mixed and the suspension was immediately placed on the Teflon plate of the rheometer. The stainless steel parallel plate geometry was lowered approximately 0.2 mm into the sample, and time-dependent changes in G', G" and η* were recorded during an oscillatory controlled stress experiment with a time sweep. All tests were performed at room temperature under a controlled frequency of 1 Hz and 0.25% strain to avoid destroying sample structure.

The crossover of the G' and G" curves as well as the slope of the complex viscosity curve were analyzed using Rheology Advantage Data Analysis software (v4.1.2; TA Instruments).

Figure 9:
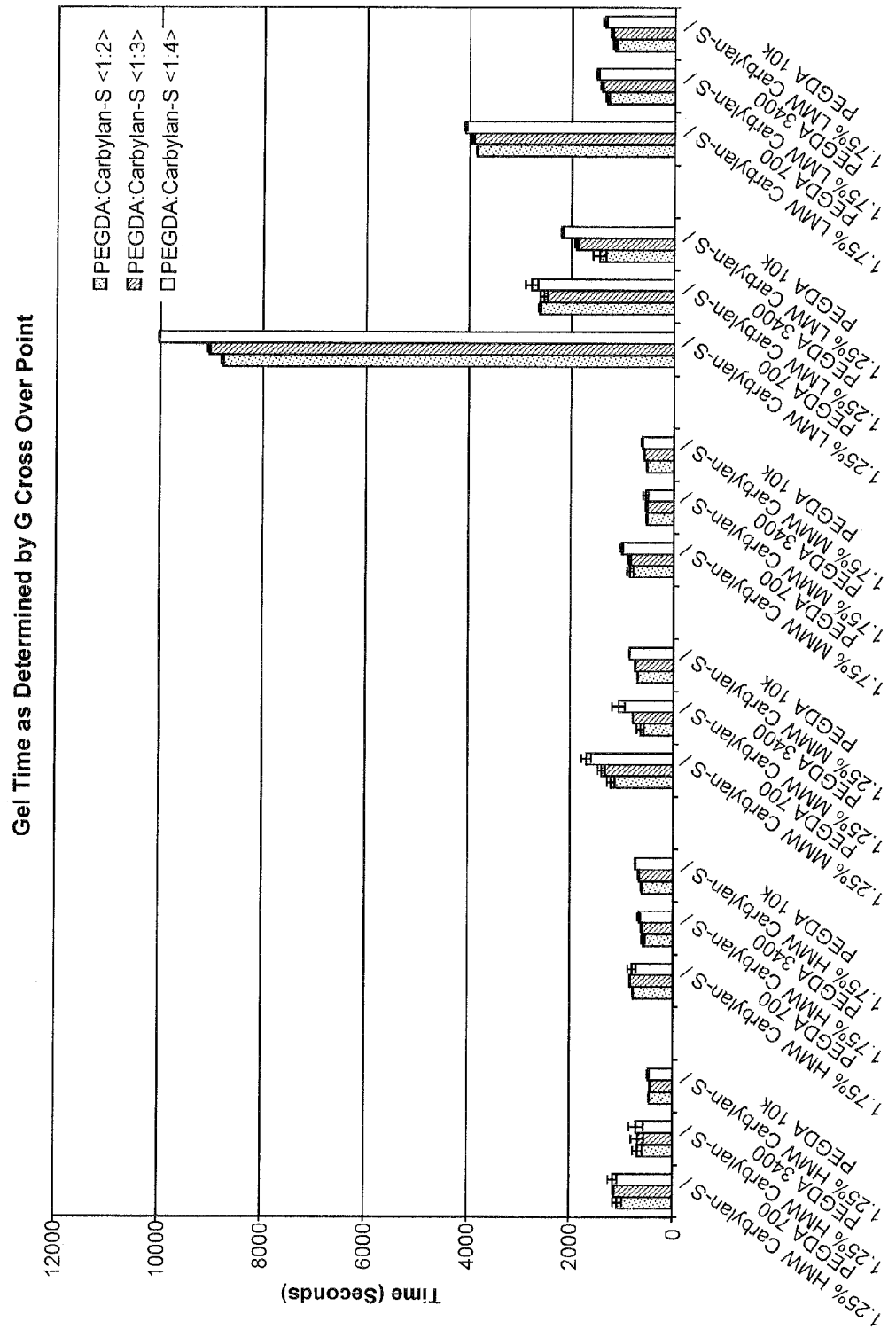
FIG. 9 shows the gelation time of Carbylan™-SX for different formulations.
Figure 10:
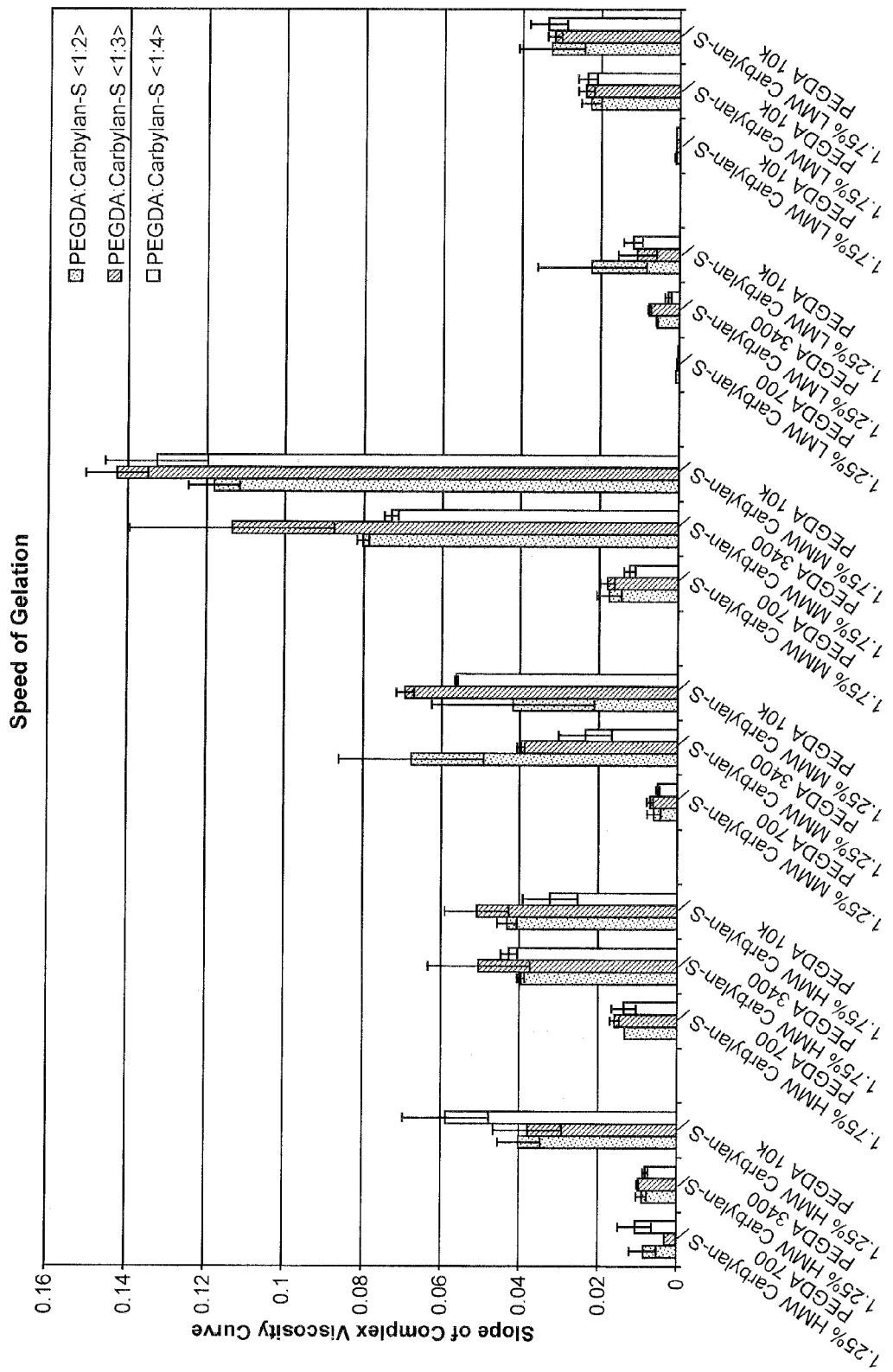
FIG. 10 shows the speed of gelation of Carbylan™-SX for different formulations.

In FIG. 9, the data show that the gel point ranges from approximately 10 minutes to almost 170 minutes. Higher molecular weights for both the starting material, Carbylan™-S, and crosslinker, PEGDA, generally result in materials with a faster gel time. In FIG. 10, the graph shows the slope of the complex viscosity, $\eta^*$, curve from the gel point to approximately 10 minutes following the onset of gelation. The slope of this curve describes the speed with which the material's viscosity increases. While two materials may have similar gel points, their viscosity may increase a different rates giving the materials different properties at different times following gelation.

b. Enzymatic Degradation In Vitro of Carbylan™-SX

Hydrogel preparation. A 1.25% (w/v) solution of Carbylan™-S was prepared in DPBS, and then the solution ph was adjusted to 7.4 by adding 0.1 N NaOH. Then Carbylan™-SX hydrogel was prepared in a petri dish (3.5 cm in diameter) by adding 1.2 ml 4.5% (w/v) PEGDA in DPBS into 4.8 ml of an aqueous Carbylan™-S solution. The hydrogel was allowed to react to completion for 4-12 hours.

A 3.0-mm diameter biopsy punch was then used to cut a cylindrical piece of hydrogel from the gel in a petri dish. This disc was placed into a small glass vial containing 2.0 ml of hyaluronidase (HAse) solutions (0, 0.5 U/ml, 2 U/ml and 20 U/ml) that were prepared in 30 mM citric acid, 150 mM $Na_2HPO_4$, 150 mM NaCl (pH 6.3). The vials were incubated at 37° C. with orbital agitation at 150 rpm. The weight of each sample was monitored using a digital scale and was measured every 24 hrs for 5 days. The samples were removed from the incubator and the enzyme solution was discarded. The hydrogel cylinders were then placed on filter paper and allowed to blot dry for several seconds. The samples were then weighed using a digital scale and returned to the glass vial with fresh HAse solution.

Figure 11:
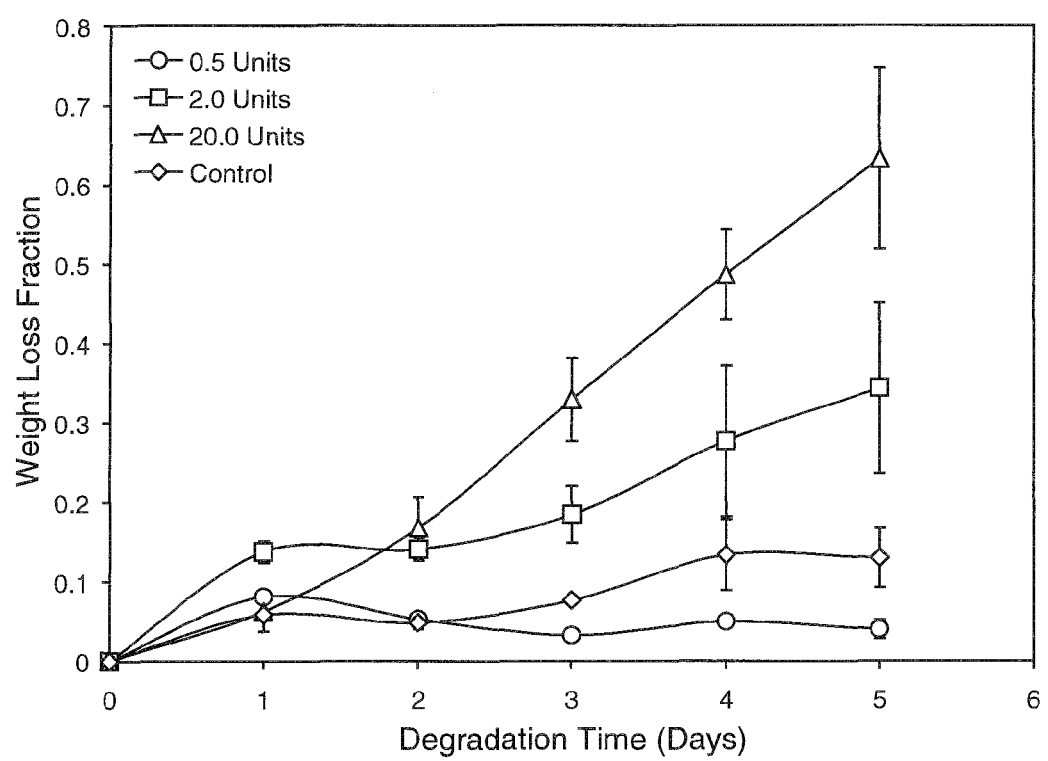
FIG. 11 shows the weight loss fraction vs. time for HAse degradation of Carbylan™-SX. Key: diamonds, no enzyme control; circles, 0.5 U/ml; squares, 2.0 U/ml; triangles, 20 U/ml.

The weight loss fraction was defined as $1-W_t/W_o$, where $W_t$ is the weight of the sample at time t and $W_o$ is the original weight of the sample. The values for the weight loss percent were plotted as a function of time shown in FIG. 11. The result indicated that the digestion was dependent on enzyme concentration. After 5 days at 37° C. with gentle agitation, ca. 63% of the hydrogel was digested at the highest HAse concentration (20 U/ml) employed. No significant degradation occurred in the absence of added HAse. This result revealed that Carbylan™-SX is slowly hydrolyzed in vivo and that this degradation rate is similar to that found previously for PEGDA-crosslinked HA-DTPH.

II. Applications of Carbylan™-SX and Carbylan™-GSX

1. Prophylaxis of Extracellular Matrix (ECM)-Based Dysphonias with Carbylan™-SX Hydrogels Utilization of injectable proprietary chemically-modified HA derivatives at the time of intentional resection may facilitate wound repair for prevention of ECM based dysphonias. Thirty-three rabbit vocal folds were biopsied bilaterally. Two groups of rabbits were unilaterally treated with two different HA-based hydrogels (Carbylan™-SX and HA-DTPH-PEGDA) at the time of resection. At first, a 1.5% (w/v) Carbylan™-S (medium molecular weight, 50% degree of substitution) solution and 1.5% (w/v) HA-DTPH (medium molecular weight, 50% degree of substitution) solution were prepared in DPBS. The solution pH was then adjusted 7.4 by adding 0.1 N NaOH. The solutions were then sterilized by filtering through 0.45 μm filter. Finally, hydrogels of Carbylan™-SX and HA-DTPH-PEGDA were prepared by adding 4.5% PEGDA (MW 3400) into the corresponding Carbylan™-S or HA-DTPH solution with volume ratio of 1 to 4. Just prior to gelation, i.e., within 5-10 min, the partially gelled hydrogels were injected into the one vocal fold of the rabbit while saline was injected into the contralateral fold. Animals were sacrificed three weeks after biopsy and injection. Levels of HA in the treated vocal folds were not significantly different than controls as measured by ELISA (result not shown).

Figure 12A:
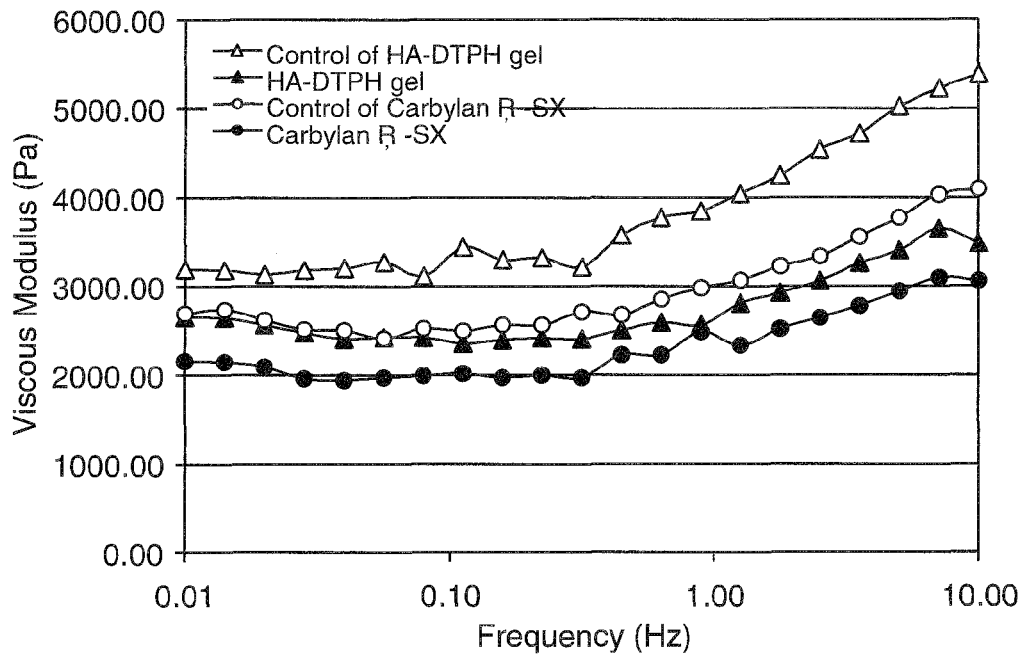
FIGS. 12A and 12B show the viscoelasticity of rabbit vocal folds injected with Carbylan™-SX and HA-DTPH-PEGDA hydrogels.
Figure 12B:
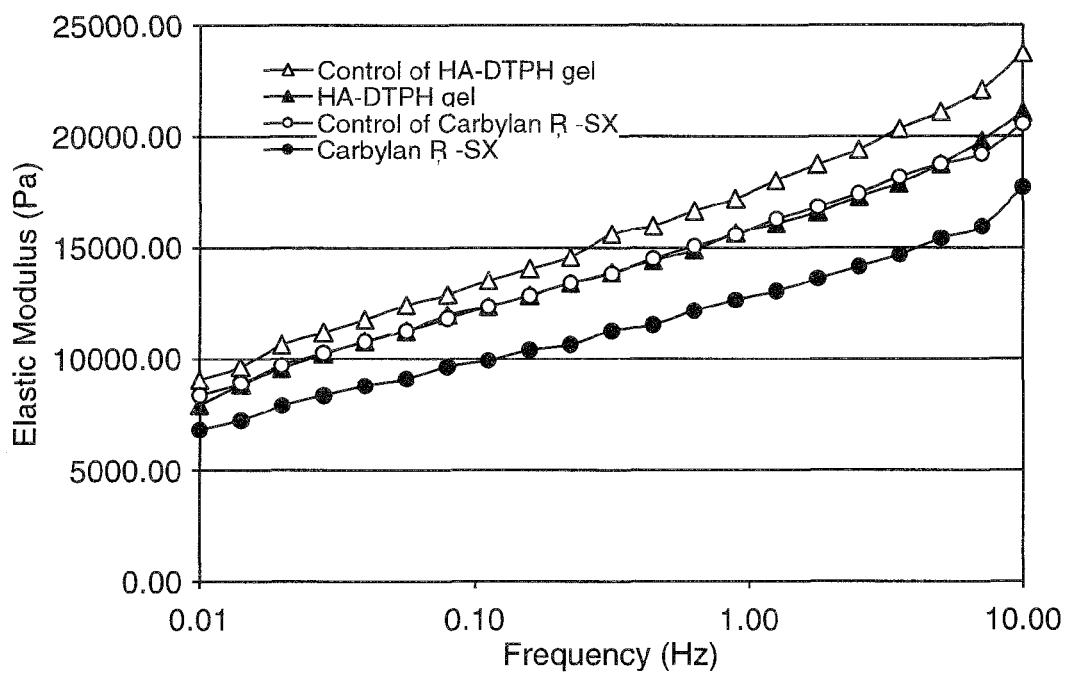

Vocal folds receiving the Carbylan™-SX injections had significantly improved biomechanical properties relative to controls. Both elasticity and viscoelasticty were improved and were very close to the properties of normal vocal folds, as measured with a Bohlin CVO Rheometer (FIG. 12). HA-DTPH-PEGDA injections yielded significantly improved viscosity but not improved elasticity. Prophylactic in vivo manipulation of the ECM with our injectable Carbylan™-SX hydrogel appears to induce tissue regeneration to yield optimal tissue composition and biomechanical properties.

2. Use of Carbylan™-SX in Preventing Airway Stenosis

Materials and Methods

Twenty-four white, female New Zealand rabbits were chosen as subjects. They ranged in weight from 3.0 to 4.5 kgs. Rabbits were randomly assigned to one of four different groups. Group 1, six rabbits underwent airway injury with no further interventions. Group 2, six rabbits underwent airway injury and were immediately stented with dry (uncoated) stents. Group 3, six rabbits underwent airway injury and were immediately stented with a HA-gel coated stents. Group 4, six rabbits underwent airway injury and were immediately stented with HA-film coated stents.

Stent Preparation

A 1.5% (w/v) Carbylan™-S (medium molecular weight, 50% degree of substitution) solution was prepared in DPBS. Then the solution pH was adjusted 7.4 by adding 0.1 N NaOH solution, and then the solutions were sterilized by filtering through 0.45 μm filter. After that a 4.5% PEGDA (MW 3400) solution in DPBS was added Carbylan™-S solution according to volume ratio of 1 to 4. Right before its gelation, the gelling hydrogels were coated on the outside of tracheal stents that were fashioned out of 1 cm segments of polyvinylchloride (PVC) endotracheal (ET) tubes. Stents were cut from 3.0 mm ID ET tubing for group 3 and 3.5 mm ID ET tubing for groups 2 & 4. The stents were 1 cm in length based on previous success in a rabbit model. Then the coated tube was dried in sterile culture hood. The Carbylan™-S gel-coated stents were prepared in the operating suite just prior to implantation.

Procedures

All animals were anesthetized intramuscularly prior to procedures. Tracheal injury and stent placement were performed by anterior. A mid-line incision was made from the inferior border of the cricothyroid space to the superior border of the third tracheal ring, completely bisecting the cricoid cartilage. After opening the airway, the tracheal mucosa was denuded ¾ of the complete circumference, at the level of the cricoid, using a j-curette. Epithelial scrapings were limited to 6 mm in longitudinal length.

Stents were then implanted in study groups 2-4 and anchored in place with one nylon suture tied external to the skin of the neck. The trachea and neck were then closed with Vicryl® sutures and the rabbits were allowed to recover three weeks.

After three weeks recovery the tracheal stents were removed using a trans-oral endoscopic technique. The animals were then given an additional three weeks recovery prior to euthanasia. They were then sacrificed and the airways were harvested for histological and morphometric measurements.

Results

Figure 13A:
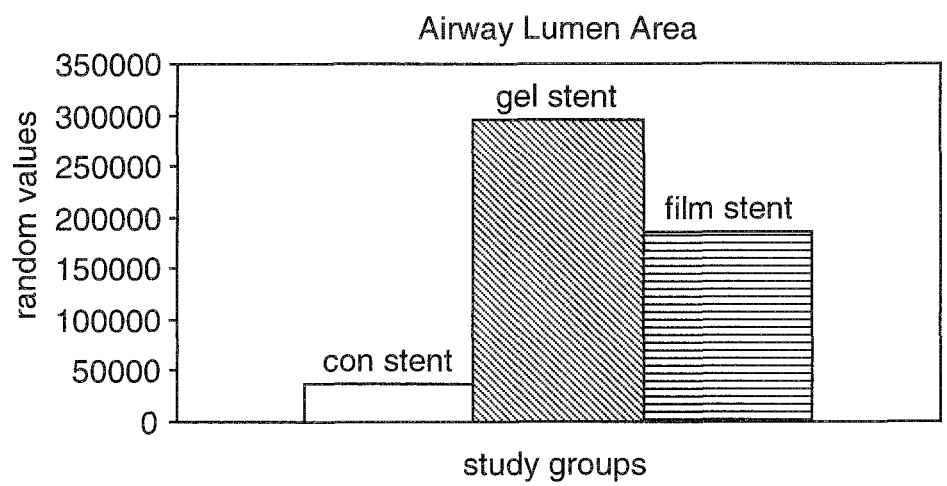
FIGS. 13A and 13B show the airway lumen area (FIG. 13A) and smallest airway diameter (FIG. 13B) of rabbit trachea after removal of different stents.

Preliminary results have shown that airway cross-sectional areas are significantly smaller in study groups 1 & 2. The average lumen area in group 2 was measured to be 37,904 while those of groups 3 & 4 were 296,024 and 186,444 (FIG. 13A). These numbers are unit-less as they were assigned by imaging software (imageProPlus).

Figure 13B:
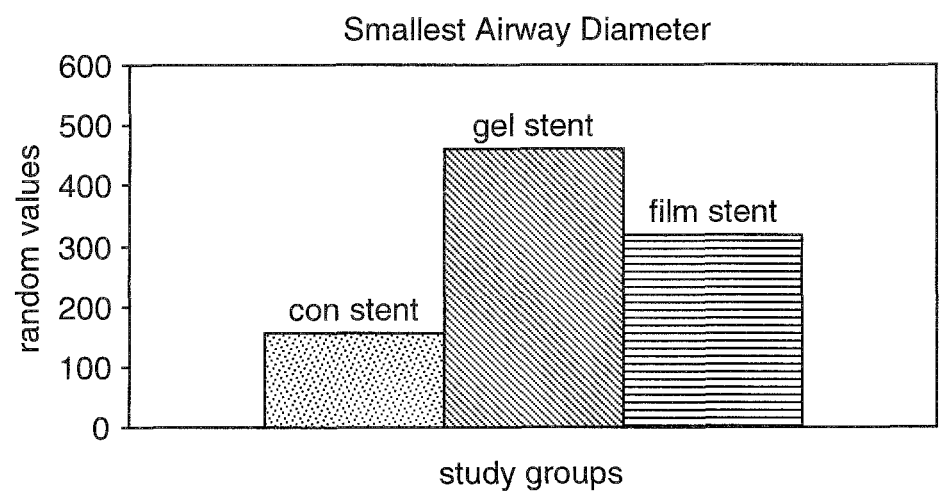

In addition to having larger cross-sectional areas, groups 3 & 4 also appear to have largest diameter measurements when comparing smallest diameters (~463 and ~315) (FIG. 13B). Likewise, these measurements were made by imaging software and are therefore unit-less.

3. Prevention of Ostia Scarring after Sinus Surgery

Materials

Carbylan™-S was prepared using the techniques described above at three different molecular weights (low (LMW), medium (MMW) and high (HMW)). Two different starting concentrations (1.25 and 1.75 mg/ml) were crosslinked to form Carbylan™-SX with three different sizes of PEGDA (1000, 3400 and 10,000 Da) at three different crosslinking ratios (PEGDA:thiol=1:2, 1:3 and 1:4).

Gels with favorable rheological properties were used to establish efficacy of nanostenting Carbylan™-SX gels in preventing sinus scarring in vivo in a rabbit sinus ostium model. Briefly, the animals were anesthetized and the soft tissue and periosteum overlying the maxillary sinuses was elevated. The anterior wall of the maxillary sinus was removed with a microsurgical drill and 4 mm. through-and-through wounds created within the medial walls of the sinuses. The gels were injected into one side (chosen randomly); the contralateral sinus wound was untreated. In this way, each animal had an experimental and control side. After 14 days, the animals were euthanized and the wounds examined. The diameter of each rabbit ostia was measured and the untreated and experimental groups were compared using a paired, two-tailed Student's t test with significance at $p<0.05$.

Results

For ease of application, the ideal material would exhibit a fast gelation time coupled with a rapid increase in viscosity with the intention that a physician could mix the Carbylan™-S with PEGDA and inject into a patient without much delay and have the material remain in the sinus cavity. From examination of the rheological data, six combinations of the starting material, linker length and crosslinking ratio best suited for nanostenting gels were chosen from the original fifty-four and are shown in Table 6.

TABLE 6

Six combinations of Carbylan ™-SX chosen for use in animal studies

| Starting Material | Crosslinker/Ratio |
|---|---|
| 1.75% HMW Carbylan ™-S | 3400 Da PEGDA, 1:4 |
| 1.75% HMW Carbylan ™-S | 10 kDa PEGDA, 1:4 |
| 1.25% MMW Carbylan ™-S | 3400 Da PEGDA, 1:2 |
| 1.25% MMW Carbylan ™-S | 3400 Da PEGDA, 1:4 |
| 1.75% MMW Carbylan ™-S | 10 kDa PEGDA, 1:4 |
| 1.75% MMW Carbylan ™-S | 3400 Da PEGDA, 1:4 |

Figure 14:
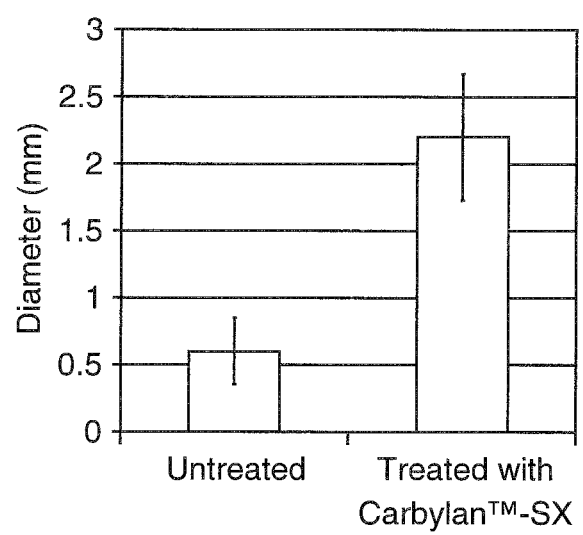
FIG. 14 shows ostial diameter as measured 14 days post sinus surgery in a rabbit model with and without the application of Carbylan™-SX.

These six materials will then be used for further animal studies. Preliminary results from animal studies performed with the MMW Carbylan™-S crosslinked with the 3400 Da PEGDA at a ratio of 1:4 are shown in FIG. 14. For the untreated side, the ostial diameter for 8 animals was 0.6 mm, this opening significantly increased to 2.2 mm following treatment with Carbylan™-SX. The data show that Carbylan™-SX application following sinus surgery significantly decreases scar contracture.

4. Co-Crosslinked Gelatin-DTPH with Carbylan™-SX as a Matrix for Cell Growth a. The Cytoskeletal Organization of NIH 3T3 on Hydrogel Surface Solution preparation. Carbylan™-S and gelatin-DTPH were dissolved in cell culture medium to give 1.5% (w/v) and 3.0% (w/v) solution respectively. The solution pH was adjusted to 7.4 with 0.1 N NaOH. PEGDA (MW 3400) was dissolved in DPBS to give a 4.5% (w/v) stock solution to produce Carbylan™-GSX (FIG. 8). Each of the three solutions was sterilized by filtering through 0.45 µm filters.

Blends. The Carbylan™-S solution and gelatin-DTPH solution were mixed according to volume ratio 100/0, 85.7/14.3, 66.3/33.3, 31.5/68.5 and 0/100, which is corresponds to a weight ratio of 100/0, 75/25, 50/50, 25/75 and 0/100.

Hydrogel preparation. Four volumes of the blended solutions were crosslinked by adding one volume of the PEGDA stock solution, mixing, and placing a 0.3-ml aliquot was injected into each well of 24 well plates for gelation to occur.

Cell culture. After 1 h, 30,000 NIH 3T3 fibroblasts were seeded onto the surface of each hydrogel. After 24 h culture in vitro, cells were fixed by formalin and stained with Oregon green.

Figure 15:
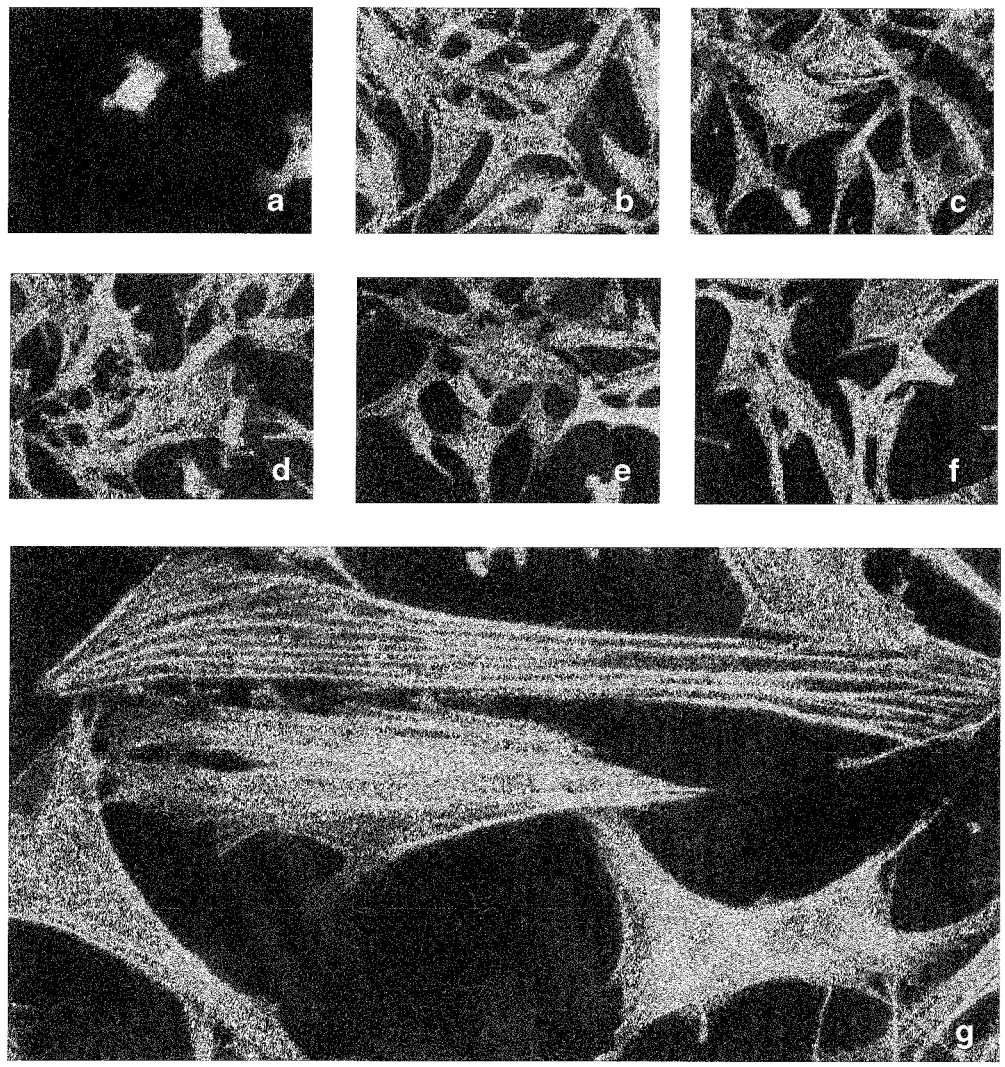
FIG. 15 shows the visualization of F-actin with FITC-phalloidin staining of NIH 3T3 fibroblasts cultured on Carbylan™-GSX hydrogel surfaces for 24 h. Ratio of Carbylan™-S/Gelatin-DTPH: (a) 100/0, (b) 75/25, (c) 50/50, (d) 25/75, (e) tissue culture plate (control) and (e) enlarged picture of panel (b).

The result in FIG. 15 indicated that Carbylan™-SX is a good candidate for anti-adhesion, since fibroblasts fail to attach (FIG. 15a). In contrast, the blended Carbylan™-SX/gelatin-DTPH (Carbylan™-GSX) was an excellent matrix for cell attachment and spreading, and promotes cell growth (FIGS. 15b, c, d) similar to the results obtain in disulfide crosslinked HA-gelatin gels and sponges. More actin filaments formed in the blended hydrogel (FIG. 15g) than gelatin-DTPH hydrogel alone and also control (tissue culture plate).

b. Cell Proliferation on Hydrogel Surfaces

Figure 16:
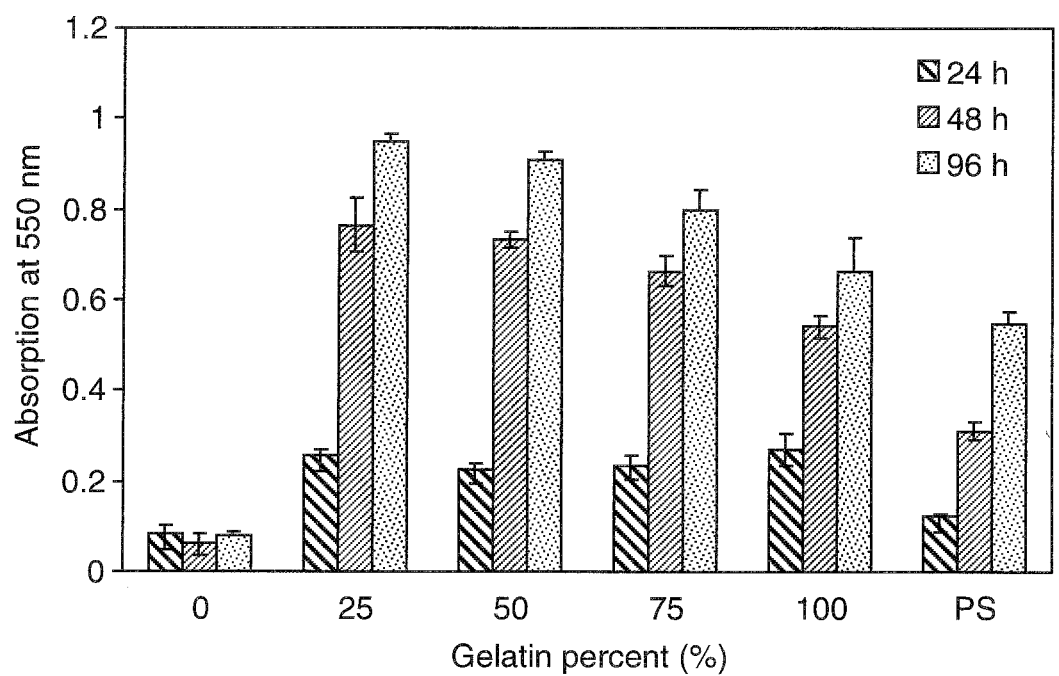
FIG. 16 shows NIH 3T3 fibroblast proliferation on Carbylan™-GSX hydrogel surfaces after 24, 48 and 96 h in vitro culture.

Blended hydrogels were prepared on the bottom of the 96 well plates as described in section i, and then 2,500 NIH 3T3 fibroblast was seeded on hydrogel surface of each well. After in vitro culture for 24, 48 and 96 h, the cell number was determined by MTS assay (FIG. 16). The results also indicated that Carbylan™-SX/gelatin-DTPH blended hydrogels (Carbylan™-GSX) are better matrices for supporting cell proliferation than gelatin-DTPH alone and control (tissue culture plate).

5. Tympanic Membrane Perforation Repair

Methods

The following materials were prepared for analysis of TMP repair: Carbylan™-S, Gelatin-DTPH, Carbylan™-S/Gelatin-DTPH (Carbylan™-GSX), Gelfoam™, and Epifilm™. Briefly, Carbylan™-S was dissolved in DBPS buffer to form a 1.5% (w/v) solution. The pH was adjusted to 7.4 using aliquots of NaOH. Gelatin-DTPH was dissolved in DPBS buffer to form a 3.0% (w/v) solution and the pH was adjusted to 7.4 using aliquots of NaOH. PEGDA (Nektar) was dissolved in DBPS buffer to form a 4.5% (w/v) solution. The solutions were then sterilized in a sterilization hood using a bottle top filter (Corning) with a 0.45 µm cellulose acetate membrane. After sterilization, the solutions were placed in 1.0 ml sterile centrifuge tubes containing 0.4 ml of Carbylan™-S, 0.4 ml of Carbylan™-S/Gelatin-DTPH (1:1 w/w), 0.4 ml of Gelatin-DTPH, and 0.1 ml of PEGDA for the proper mixture of 4:1 GAG to crosslinker ratio. The materials were then frozen at −80° C. for later use. Epifilm™ (Medtronic) and Gelfoam™ (Pfizer) were purchased already sterilized for the study. Hartley pigmented guinea pigs (Elm Hill) were obtained and anesthetized using isoflurane gas. Auditory brainstem response (ABR) tests were then performed using Intelligent Hearing System (SmartEP™) software. A myringotomy (perforation) was then performed on both ears just anterior to the umbo. One ear was left as a control while the contralateral ear was injected through the myringotomy site. Approximately 0.4 ml of Carbylan™ S, Carbylan™-S/Gelatin-DTPH, and Gelatin-DTPH were aspirated into a 1 ml syringe along with 0.1 ml of the crosslinker PEGDA. The materials were then mixed thoroughly and injected into the middle ear via the myringotomy site and allowed to gel for several minutes. The hydrogels formed in 7-14 min. The animals were examined daily until the TMP was fully closed.

Results

Figure 17:
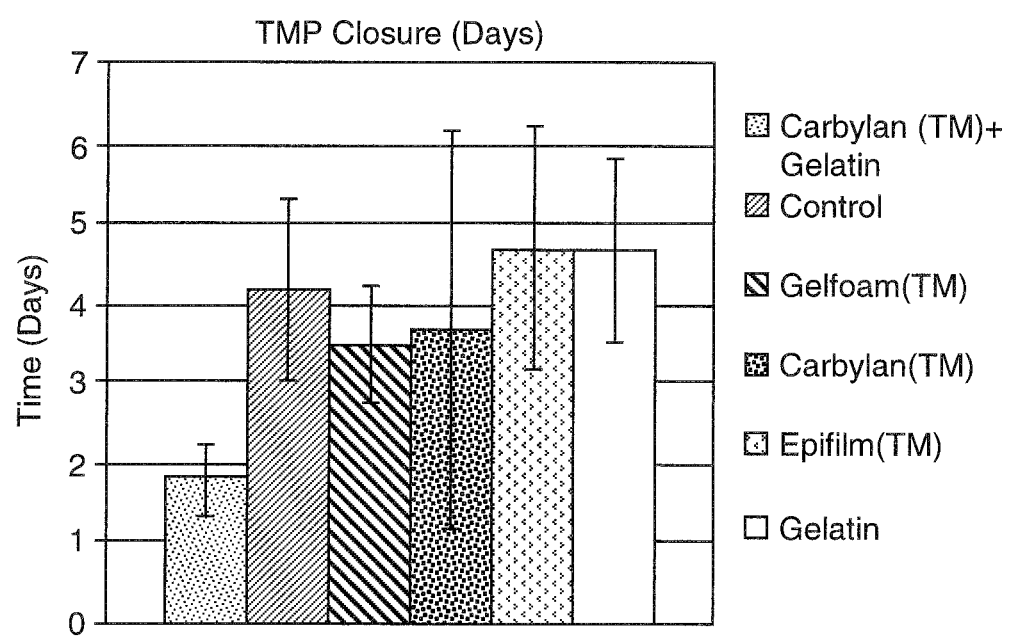
FIG. 17 shows tympanic membrane closure as a function of time in a guinea pig model, where Carbylan-SX/Gelatin had the fastest closure time.
Figure 18:
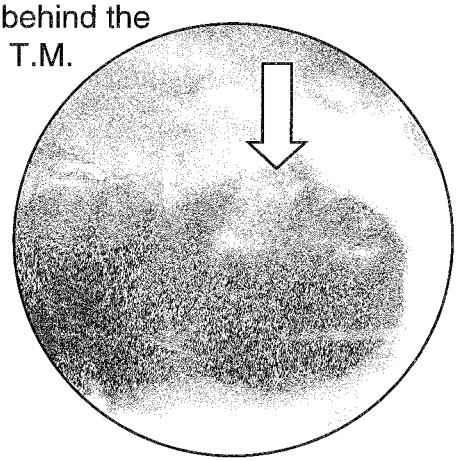
FIG. 18 shows two days post-operative healing following myringotomy and Carbylan™-GSX.

The results of the study are displayed in FIG. 17. Carbylan™-SX/Gelatin-DTPH-PEGDA (Carbylan™-GSX) had the quickest time of 1.8±0.45 days followed by Gelfoam™ at 3.5±0.71 days, Carbylan™-SX at 3.7±2.5 days and the control at 4.2±1.1 days. Epifilm™ and Gelatin-DTPH had values higher than the control at 4.7±1.5 and 4.7±1.2 respectively. There were no significant differences observed between the pre- and post-operative ABR data. This study demonstrates the validity of Carbylan™-SX/Gelatin-DTPH-PEGDA as a material to promote re-epithelialization and complete closure of TMP's within 2 days (FIG. 18). This will allow the procedure to be performed in-office and eliminate the morbidity associated with the anesthesia involved in the current treatment.

6. Prevention of Intraperitoneal Adhesions Using Carbylan-SX Films in Rat Uterine Horn Model (Pilot Study)

Grouping: four rats/per group. (1) No treatment; (2) Carbylan-S-PEGDA (Carbylan-SX) film; and (3) Carbylan-SX film with 0.5% MMC.

The rats were sacrificed two weeks after the surgery. The adhesions between the two injured uterine horns were assessed macrographically. Then the uterine horns with surrounding tissues were excised and processed for Masson's trichrome staining. Results are shown in FIGS. 19A-C and FIGS. 20A-C.

Figure 19A:
FIGS. 19A, 19B, and 19C show the macrographical observation of rat uterine horns after treatment with different films.
Figure 19B:
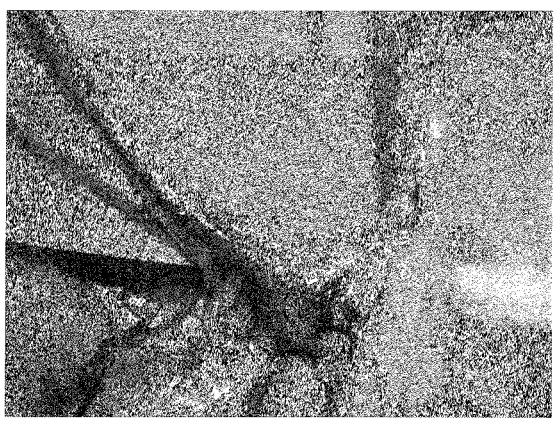
Figure 19C:

FIGS. 19A-C show the macrographical observation of uterine horns after different treatments. For FIG. 19A, which was without treatment, very firm adhesion formed between two uterine horns. Adhesions were also found between the uterine horn and surrounding intraperitoneal fat. For FIG. 19B, treated with Carbylan-S-PEGDA film, no adhesions formed between two uterine horns but there were some degree of adhesions formed between the uterine horn and surrounding intraperitoneal fat. For FIG. 19C, treated with Carbylan-S-MMC(0.5%)-PEGDA film, no adhesions formed between two uterine horns. No adhesions formed between the uterine horn and surrounding intraperitoneal fat.

Figure 20A:
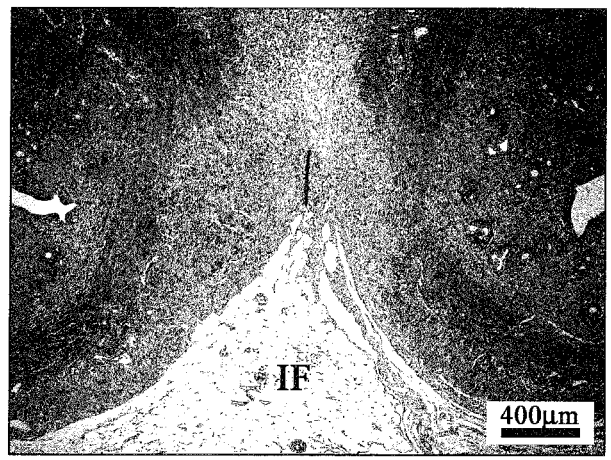
FIGS. 20A, 20B, and 20C show the histological observation of rat uterine horns after treatment with different films.
Figure 20B:
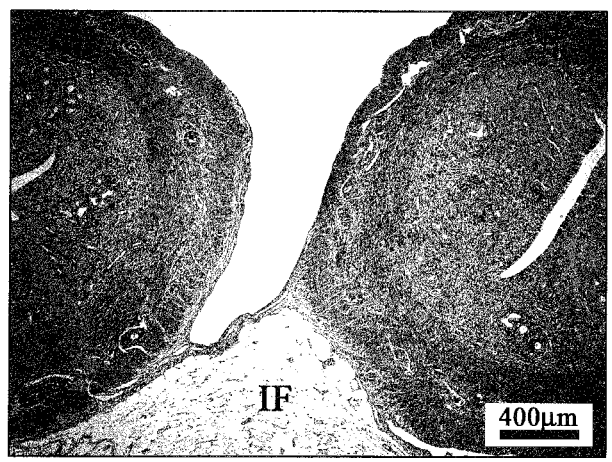
Figure 20C:
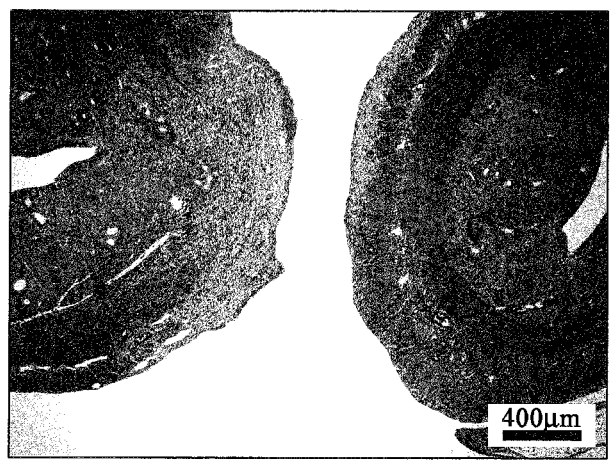

FIGS. 20A-20C show the histological observation of uterine horns after different treatments. For FIG. 20A, corresponding to no treatment; very firm adhesions formed between the two uterine horns. Adhesions were also found between the uterine horn and surrounding intraperitoneal fat. For FIG. 20B, treated with Carbylan™-SX film; no adhesions formed between two uterine horns but there was some degree of adhesions formed between the uterine horn and surrounding intraperitoneal fat. For FIG. 20C, treated with Carbylan-S-MMC(0.5%)-PEGDA film; no adhesions formed between two uterine horns. Moreover, no adhesions formed between the uterine horn and surrounding intraperitoneal fat. Masson's trichrome staining, scale bar: 400 µl.

The insertion of crosslinked Carbylan™-SX films without MMC prevented the adhesions formed between the two uterine horn but not between the uterine horn and surrounding intraperitoneal fat. The insertion of crosslinked Carbylan-SX films containing covalently-linked 0.5% MMC could prevent the adhesions formed between the two uterine horns and the uterine horns to surrounding intraperitoneal fat.

7. The Establishment of Breast, Colon, and Ovarian Cancer Animal Model in Nude Mouse Human breast cancer cell lines (MDA-MB-231, MDA-MB-468, SK-Br-3, and MCF-10A), colon cancer lines (Caco-2, HCT-116, and HCA-7), and one ovarian cancer cell line (SK-OV-3) were loaded in Carbylan™-GSX and HA-DTPH-gelatin-DTPH-PEGDA hydrogel at concentration of 50×10$^6$ cells/ml and injected subcutaneously into the backs of nude mice. In addition, the Caco-2 cells loaded into Carbylan™-GSX hydrogels were injected into the subserosal layer of the cecum in a nude mouse. The SK-OV-3 cells loaded in a Carbylan™-GSX hydrogels were injected into the capsule of the ovary in a nude mouse. As controls, cells suspended in DPBS at the same concentration were injected subcutaneously or intraperitoneally into nude mice. One month after the injection, the injected sites were examined macrographically and histologically. The results are shown in FIGS. 21-28.

Figure 21A:
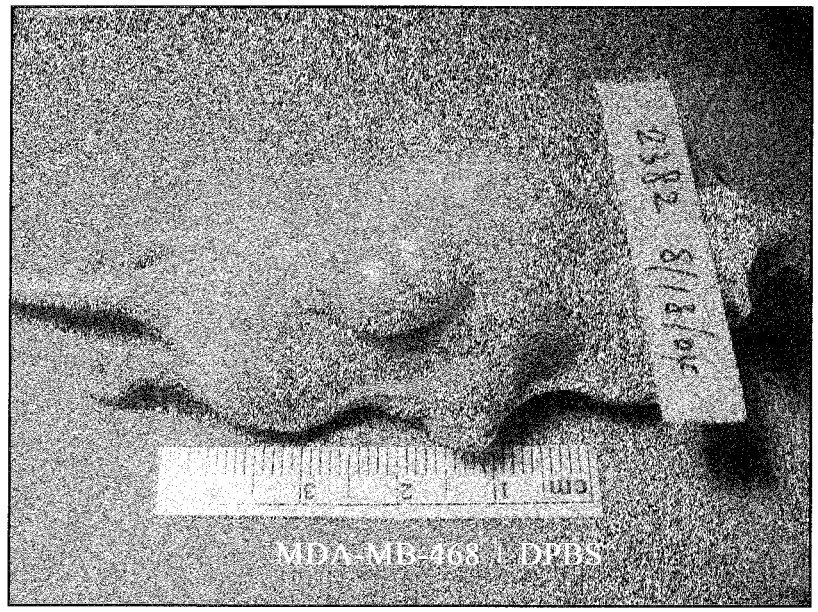
FIGS. 21A and 21B show the macrographical view of tumors after subcutaneous injection of (a) MDA-MB-468 cells loaded in DPBS buffer (FIG. 21A), and (b) MDA-MB-468 cells loaded in Carbylan™-GSX hydrogels (FIG. 21B).
Figure 21B:
Figure 21C:
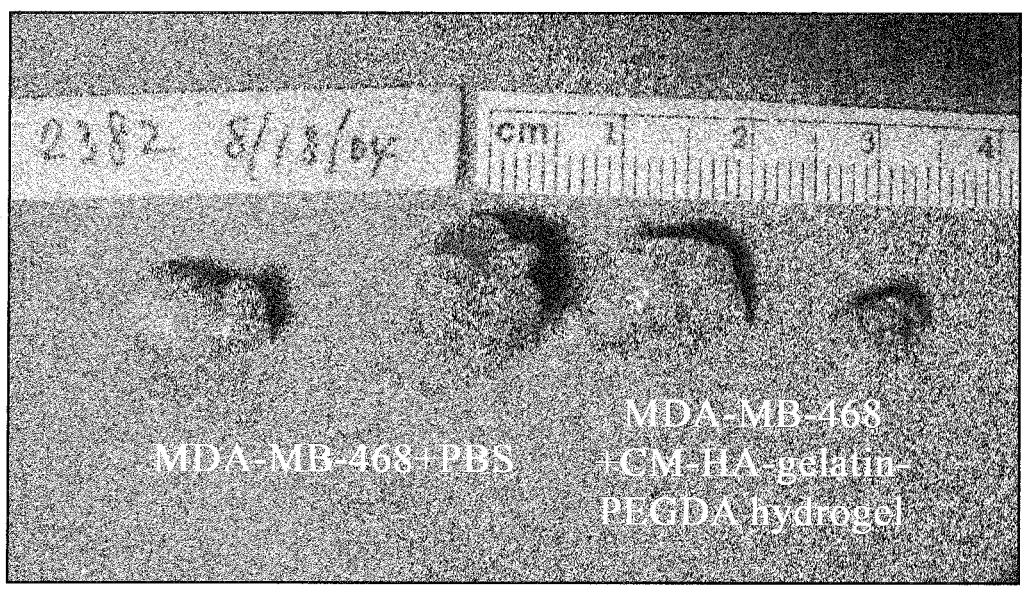
FIG. 21C shows the tumors after the skin was removed.
Figure 22A:
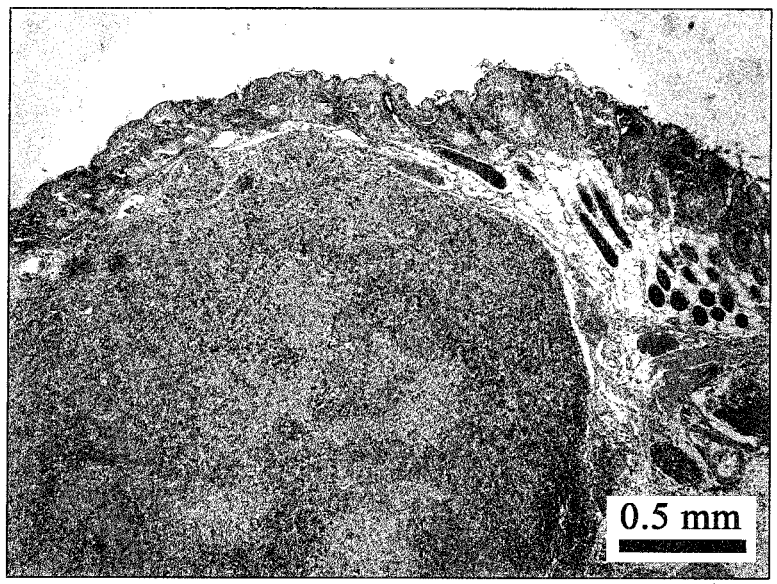
FIGS. 22A and 22B show the histological examination of newly formed tumors after subcutaneous injection of MDA- MB-468 cells loaded in (a) DPBS buffer and in (b) Carbylan™-GSX hydrogels. H&E staining, scale bar: 0.5 mm.
Figure 22B:
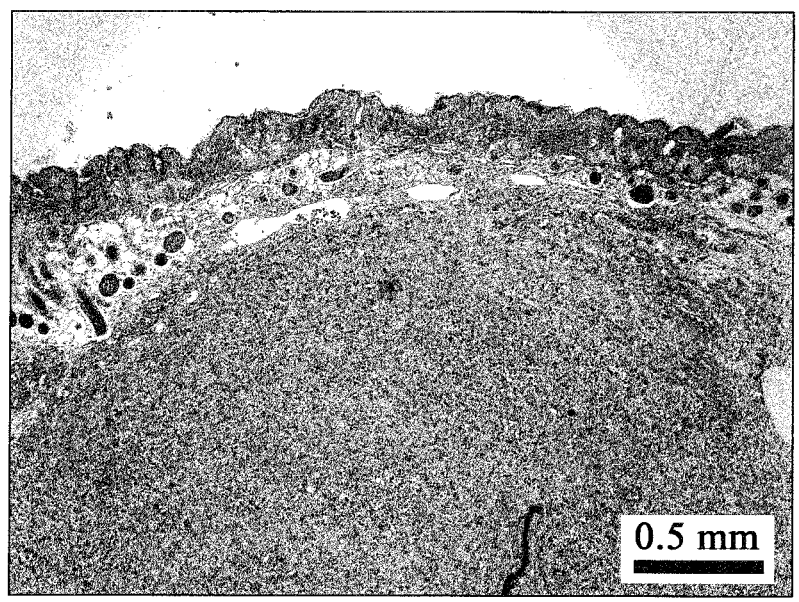
Figure 23A:
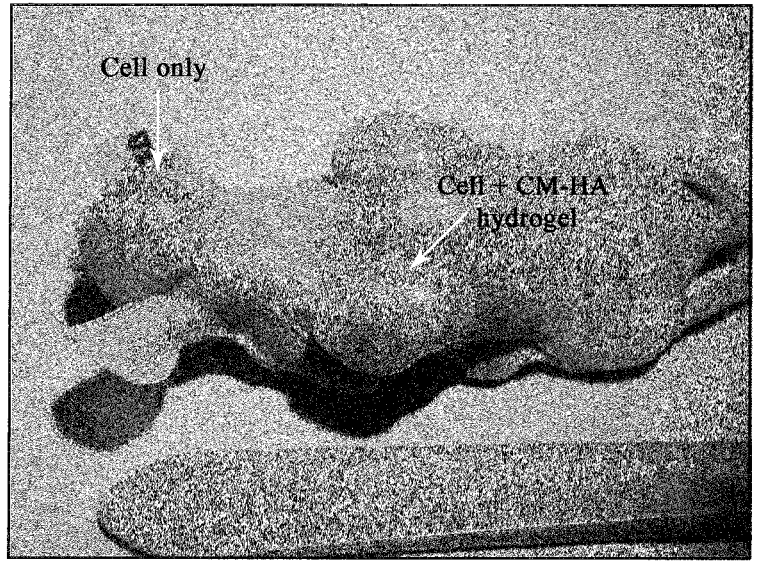
FIGS. 23A, 23B, and 23C show the macrographical view of tumors after subcutaneous injection of Caco-2 cells loaded in DPBS buffer (FIG. 23A), Carbylan™-GSX (FIG. 23B), and HA-DTPH-PEGDA/gelatin DTPH hydrogels (FIG. 23C).
Figure 23B:
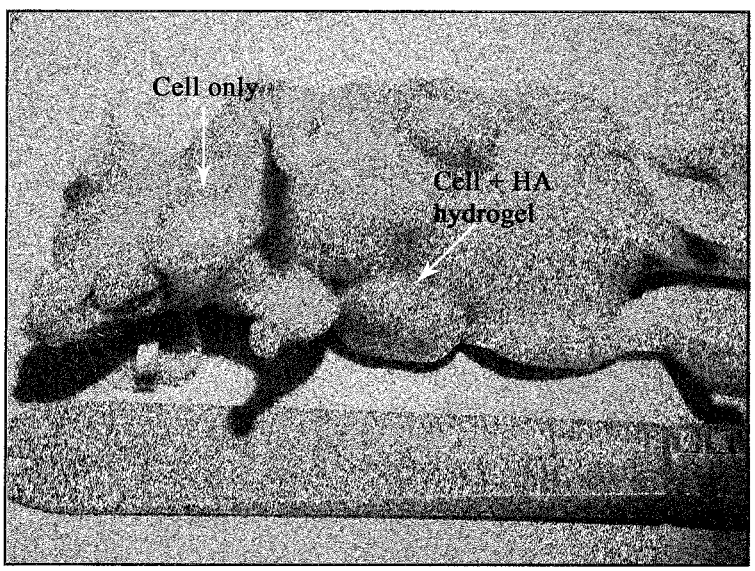
Figure 23C:
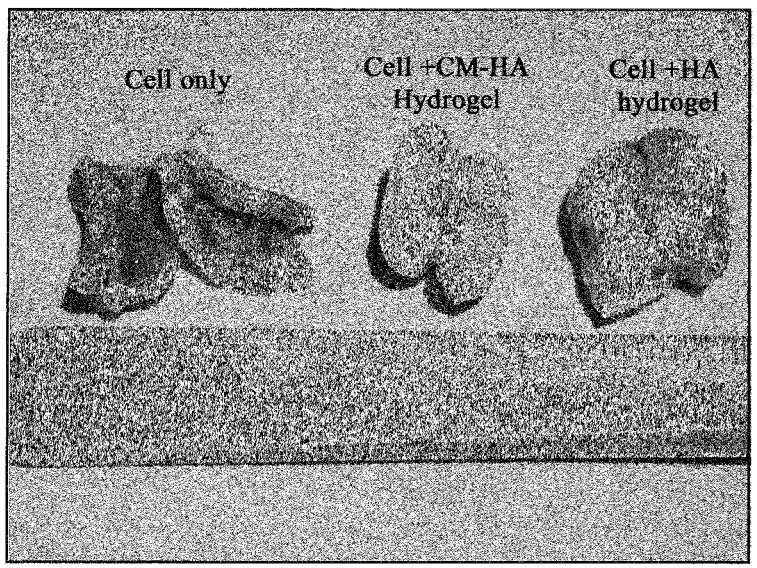

FIGS. 21A-C show the macrographical view of tumors after subcutaneous injection of (a) MDA-MB-468 cells loaded in DPBS buffer (FIG. 21A), and (b) MDA-MB-468 cells loaded in Carbylan™-GSX hydrogels (FIG. 21B). FIG. 21C shows the tumors after the skin was removed. FIGS. 22A and 22B show the histological examination of newly formed tumors after subcutaneous injection of MDA-MB-468 cells loaded in (a) DPBS buffer (FIG. 22A) and in (b) Carbylan™-GSX hydrogels (FIG. 22B). H&E staining, scale bar: 0.5 mm. FIGS. 23A and 23B show the macrographical view of tumors after subcutaneous injection of Caco-2 cells loaded in DPBS buffer (FIG. 23A), Carbylan™-S (FIG. 23B), and HA-DTPH-PEGDA hydrogels. FIG. 23C shows the cross section of tumors after the skin was removed. Note the abnormal necrotic core of the cell-only tumor, and the healthier more "normal" tumors grown in sECM hydrogels.

Figure 24A:
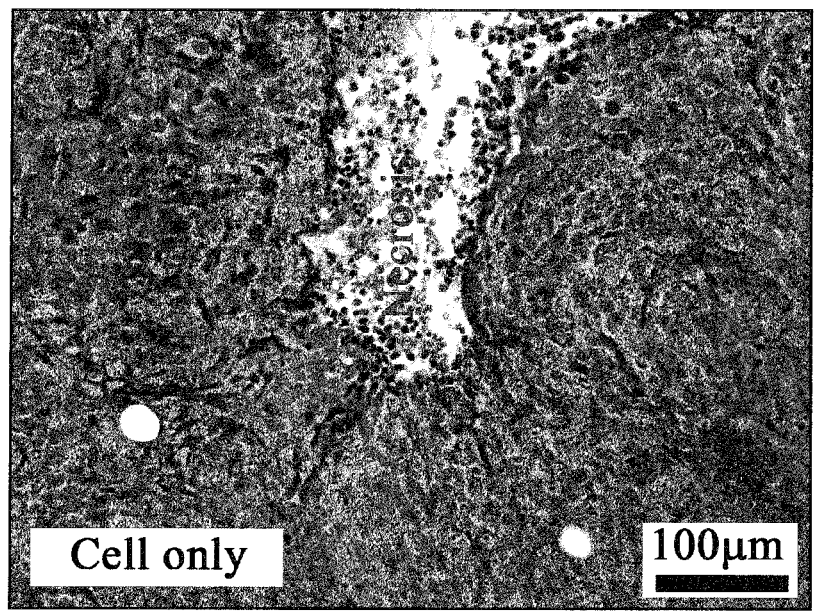
FIGS. 24A and 24B show the histological examination of newly formed tumors after subcutaneous injection of Caco-2 cells loaded in (a) DPBS buffer (FIG. 24A) and (b) Carbylan™-GSX hydrogel (FIG. 24B). H&E staining, scale bar: 0.5 mm.
Figure 24B:
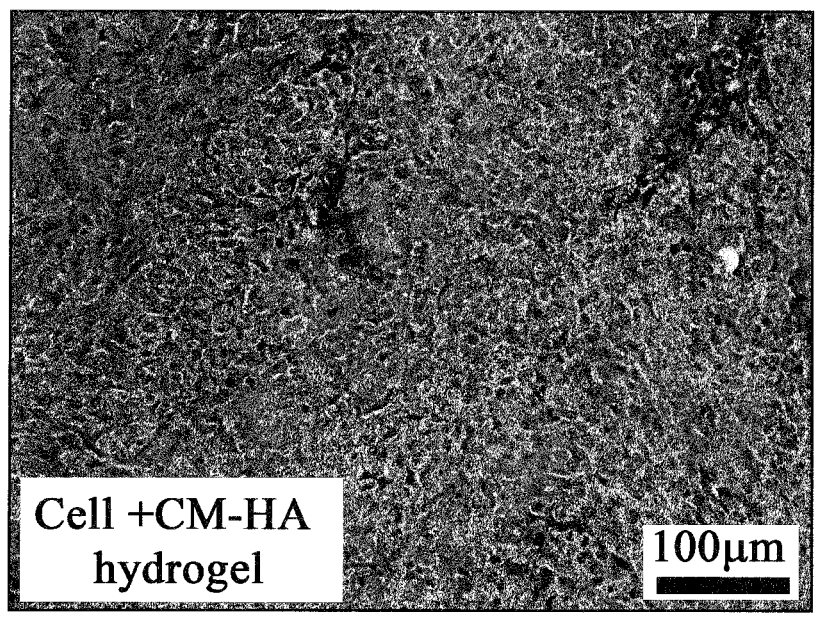
Figure 25A:
FIGS. 25A, 25B, and 25C show a mouse one month after the intraperitoneal injection of Caco-2 cells suspended in DPBS buffer.
Figure 25B:
Figure 25C:
Figure 26A:
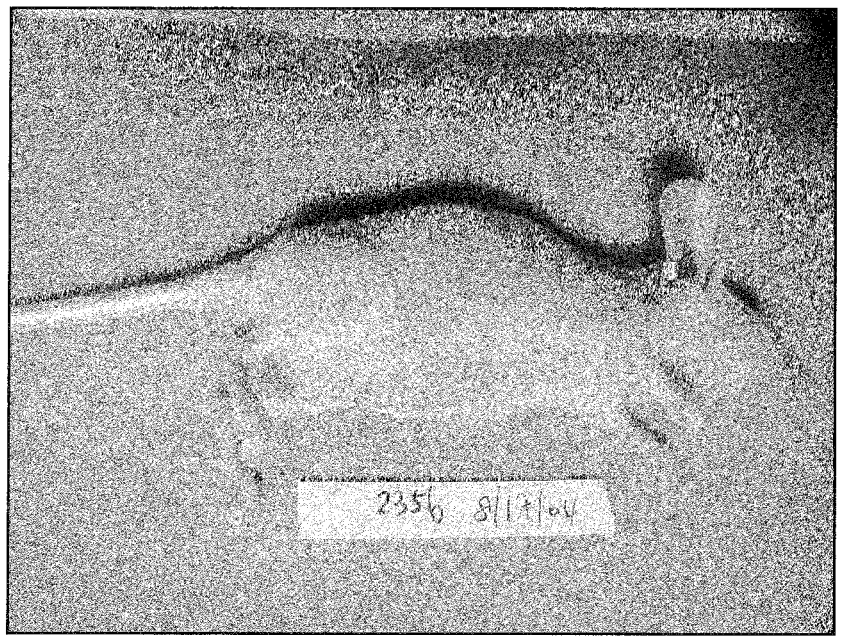
FIGS. 26A, 26B, and 26C show a mouse one month after the colon injection of Caco-2 cells encapsulated in Carbylan™-GSX hydrogels.
Figure 26B:
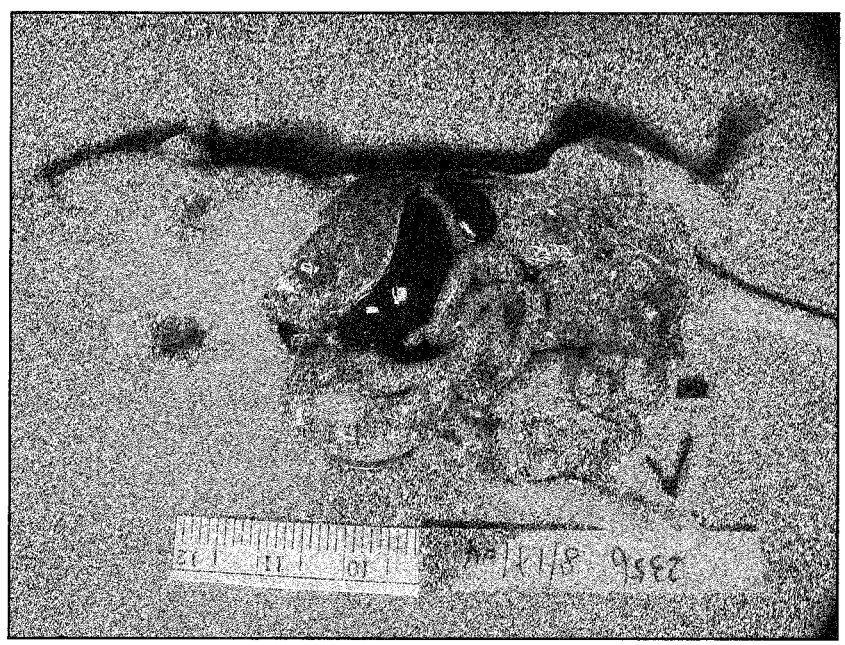
Figure 26C:
Figure 27A:
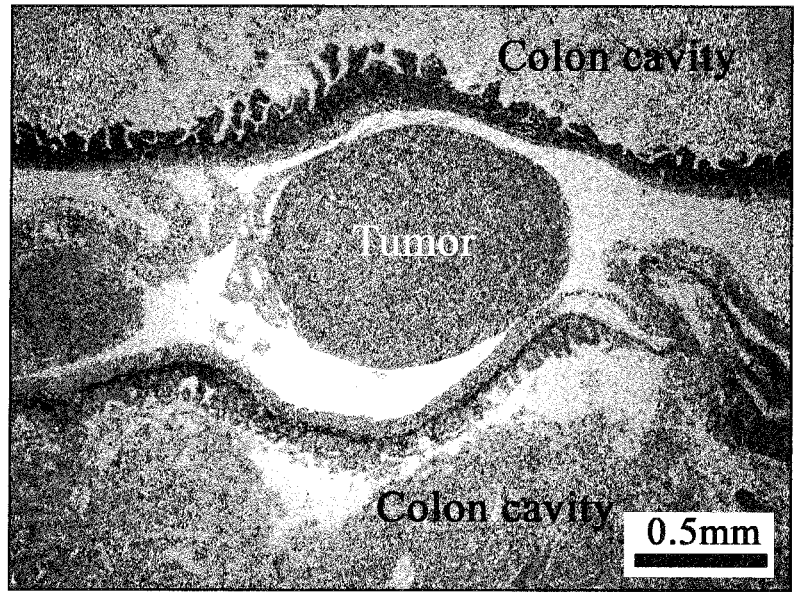
FIGS. 27A, 27B, and 27C show tumor cells one month after the intraperitoneal injection of Caco-2 cells suspended in DPBS buffer.
Figure 27B:
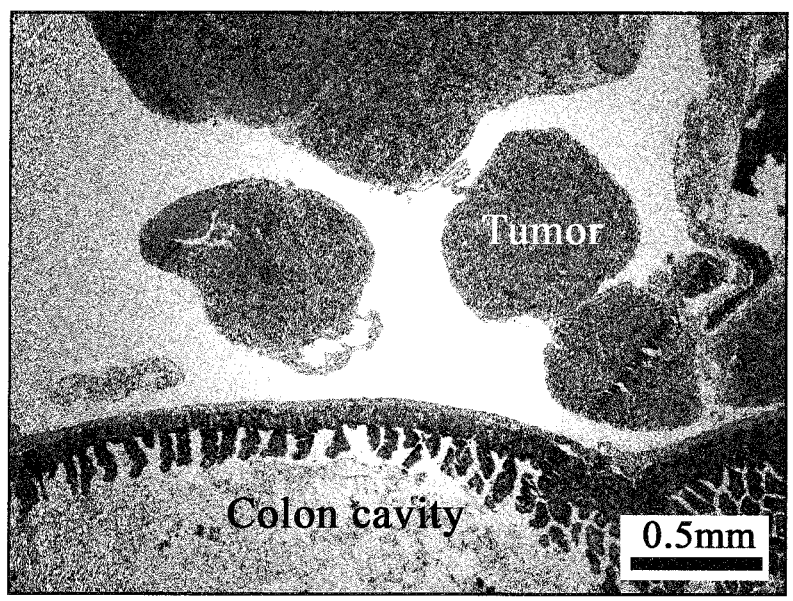
Figure 27C:
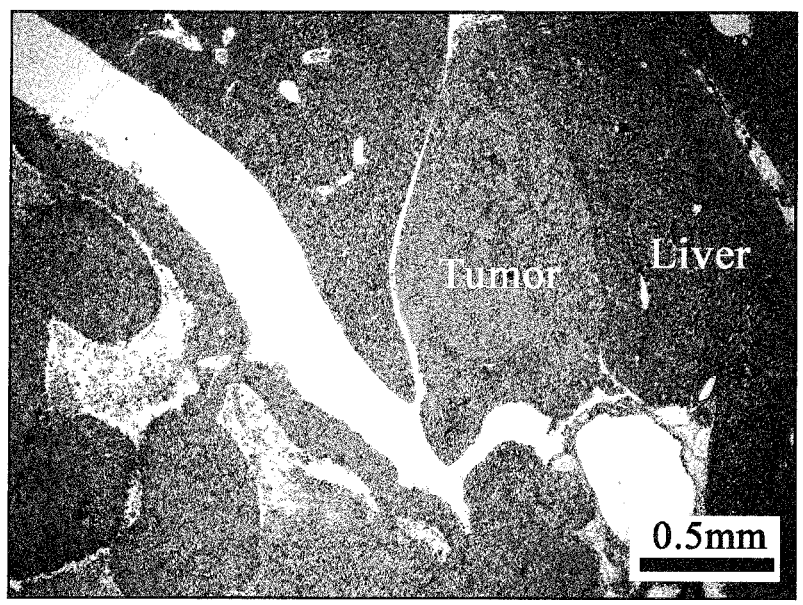
Figure 28A:
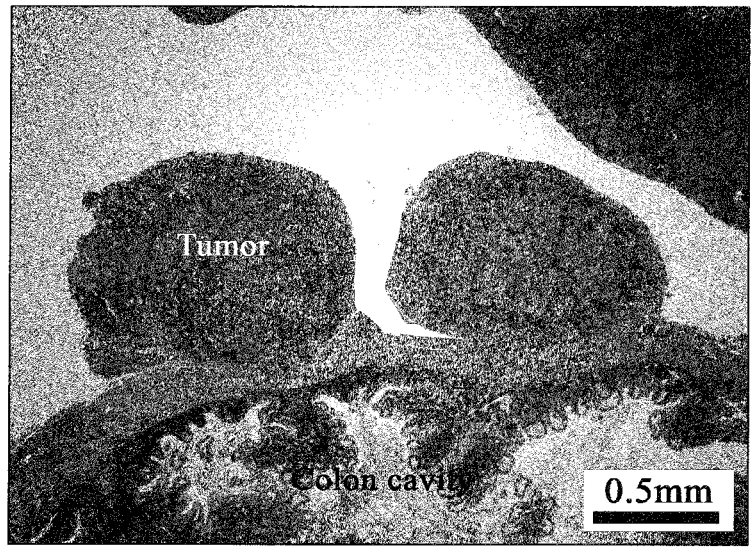
FIGS. 28A, 28B, and 28C show tumor cells one month after the colon injection of Caco-2 cells encapsulated in Carbylan™-GSX hydrogels.
Figure 28B:
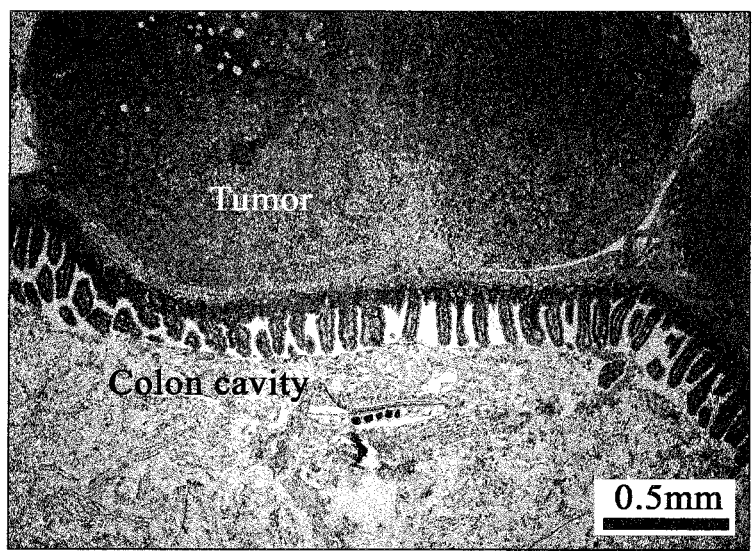
Figure 28C:
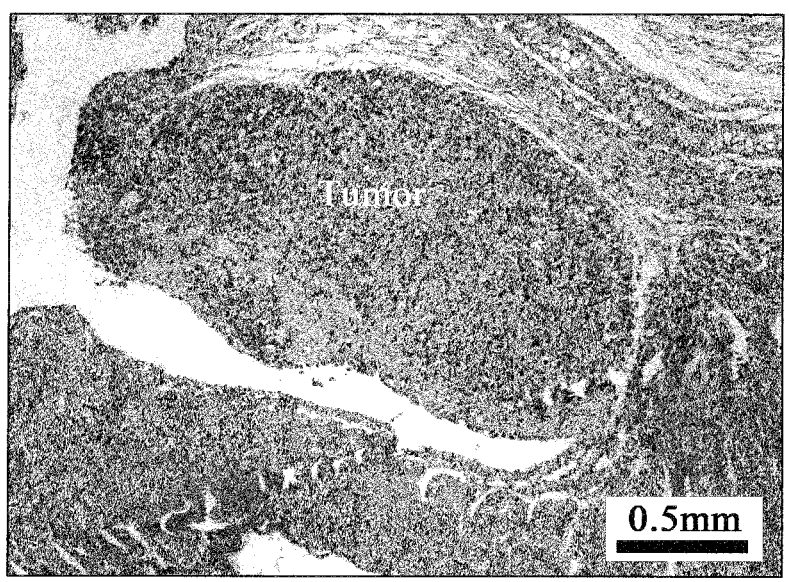
Figure 29A:
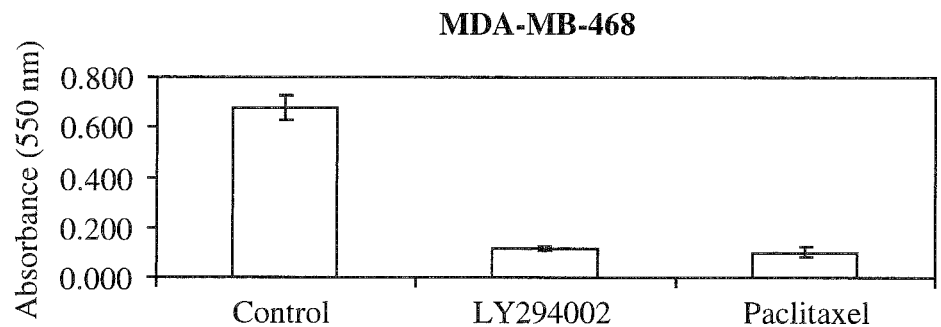
FIGS. 29A-29F show the proliferation of different cell lines cultured on Carbylan™-GSX in the presence of LY294002 and paclitaxel.
Figure 29B:
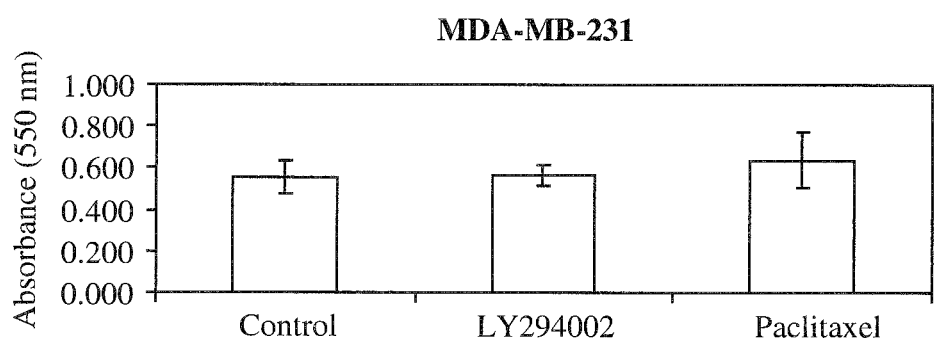
Figure 29C:
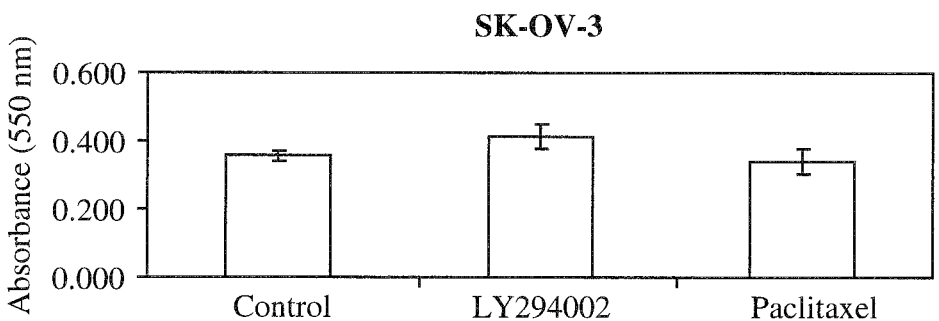
Figure 29D:
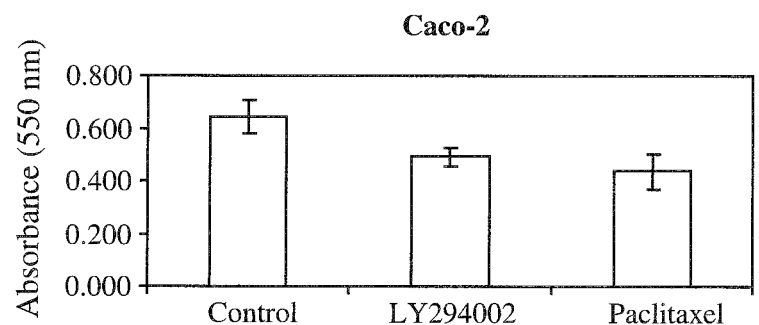
Figure 29E:
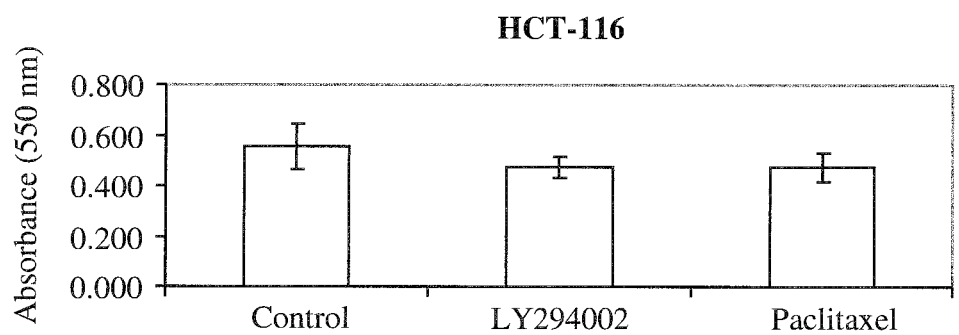
Figure 29F:
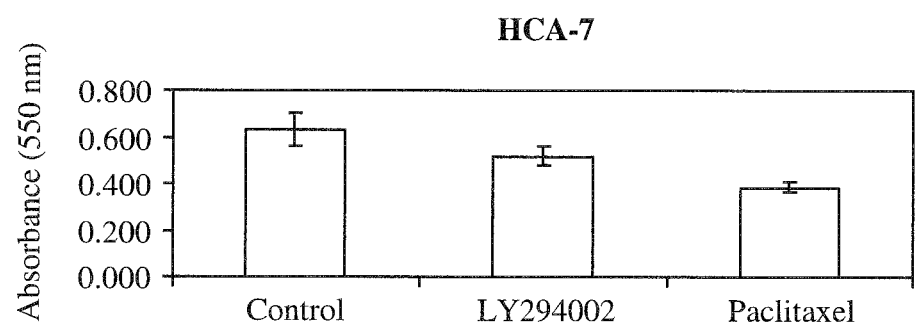

FIGS. 24A-24B show the histological examination of newly formed tumors after subcutaneous injection of Caco-2 cells loaded in (a) DPBS buffer (FIG. 24A) and (b) Carbylan™-GSX hydrogel (FIG. 24B). The H&E staining scale bar is 0.5 mm. FIGS. 25A-C show a mouse one month after the intraperitoneal injection of Caco-2 cells suspended in DPBS buffer. The waistline was increased significantly. There were multiple tumors formed in the peritoneal cavity. FIGS. 26A-C show a mouse one month after the colon injection of Caco-2 cells encapsulated in Carbylan™-GSX hydrogels. The general status of the mouse was good and there was no significant increase on the waistline after the injection. The tumors were individually distributed on the surface of the colon. FIGS. 27A-C show a mouse one month after the intraperitoneal injection of Caco-2 cells suspended in DPBS buffer. The waistline was increased significantly. There were multiple tumors formed in the peritoneal cavity. FIGS. 28A-28C show a mouse one month after the colon injection of Caco-2 cells encapsulated in Carbylan™-GSX hydrogels. The general status of the mouse was good and there was no significant increase on the waistline after the injection. The tumors individually distributed on the surface of the colon.

Based on the results presented above, the following conclusions were made.

(1) Breast tumors formed following the subcutaneous injection of MDA-MB-468 cells in both DPBS and Carbylan™-GSX hydrogel, but the quality of tumors formed was different. Necrosis was found in the tumors formed from the injection of MDA-MB-468 cells suspended in DPBS buffer but not in the sECM-grown tumors (2) The intraperitoneal injection of Caco-2 cells in both DPBS and Carbylan™-GSX hydrogel had multiple tumors formed in the peritoneal cavity and the tumors were separate from the colon and intestine. The body weight and waistline of the mouse increased significantly and more bloody peritoneal fluid was found in the peritoneal cavity. Tumor metastases were found on the liver. The same phenomenon was found in the colon injection of Caco-2 cells suspended in DPBS buffer. Individual tumors formed on the colon after the injection of Caco-2 cells loaded in Carbylan™-GSX hydrogel into subserosal layer of colon. There were no liver metastases observed and no significant increase in body weight or waistline. No bloody peritoneal fluid was found.

(3) The same above results for Caco-2 colon cancer cells were found using HCT-116 colon cancer cells.

(4) The intraperitoneal injection of SK-OV-3 cells in both DPBS and Carbylan™-GSX hydrogel had multiple tumors formed in the peritoneal cavity and the tumors were separate from the colon and intestine. The body weight and waistline of the mouse increased significantly and more bloody peritoneal fluid were found in the peritoneal cavity. Tumor metastasis to the liver was observed. There was no tumor formed in the injection of SK-OV-3 cells loaded in Carbylan™-GSX hydrogel into ovarian capsules.

(5) Taken together, the tumors cultured in the sECM (Carbylan™-GSX) hydrogels more resemble tumors in human patients than do i.p. or s.c. injected tumor cell lines in mouse xenograft models.

8. Effects of a PI3K Inhibitor and Taxol Using Cancer Cells Cultured in 3-D Culture (Carbylan™-GSX Hydrogels)

a. Cell Lines and Culture

Human breast cancer cell lines (MDA-MB-231 and MDA-MB-468), colon adenocarcinoma cell lines (Caco2, HCT116, and HCA7), and ovarian cancer cell (SK-OV-3) were obtained from American Type Culture Collections (ATCC) and maintained in RPMI 1640 medium (GIBCO) supplemented with 10 mM HEPES, 10% fetal bovine serum (Hyclone), 0.4 mM sodium pyruvate, and 0.5 mg/ml hydrocortisone, 100 U/ml penicillin, and 100 ug/ml streptomycin.

b. The Sensitivity of Cell Lines to a Known PI3K Inhibitor and to Taxol

When reaching 80-90% confluence, the above cell lines were trypsinized with 0.25% trypsin containing 1 mM EDTA and suspended in 1.25% (w/v) Carbylan™-S and 3% (w/v) gelatin-DTPH in a 50:50 (v/v) ratio in serum-free RPMI medium (pH 7.4), and then 4% (w/v) solution of PEGDA in DPBS buffer was added to the Carbylan™-S/gelatin-DTPH solution at a ratio of 4:1 (Carbylan™-S :PEGDA, v:v) and mixed by vortexing for 30 second. The final concentration of cells in Carbylan™-GSX solution was $2.0 \times 10^6$/ml. Aliquots (100 ml) of each reaction mixture loaded with cells were transferred by pipette into 24-well cell culture inserts (Corning incorporated, Corning, N.Y.) with 6.5 mm in diameter and 8.0 mm pore size. The cell loaded inserts were incubated in incubator (37° C. and 5% CO2) for two hours and then 2 ml of RPMI 1640 medium containing 10% FBS was added into each into each insert. The media were changed every two days. Two weeks after the initial culture, the media were removed from the inserts and changed with 10 mM of LY-294002 (Sigma) and 1 mg/ml of paclitaxel (Sigma) in RPMI 1640 medium containing 0.5% FBS. There were total eight inserts for each reagent each cell line. The media were also changed every two days. Two weeks after the media were changed to LY-294002 and paclitaxel containing media, the media were removed from the inserts and changed with 1.5 ml RPMI 1640 media containing 5% FBS and 15% (v/v) Cell-Titer 96 aqueous one solution cell proliferation assay (Promega, Madison, Wis.) and incubated in incubator (37° C. and 5% CO2) for three hours and then the reaction solution was transferred into 96-well plate (150 ml/per well) and the absorbance was read at 550 nm with an OPTI Max microplate reader (Molecular Devices). The inserts were rinsed twice with DPBS buffer and stained with FDA and PI at RT for 5 min and observed using a confocal laser scanning microscope (LSM 510, Carl Zeiss Microimaging, Inc., Thornwood, N.Y.).

c. Results

Figure 30:
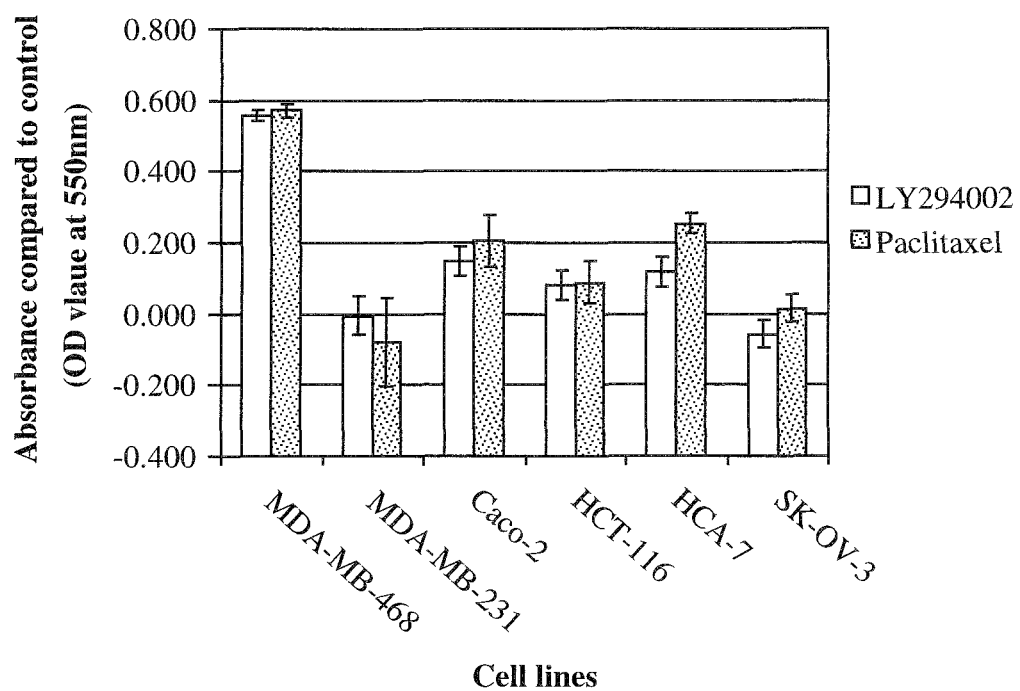
FIG. 30 shows the proliferation of different cell lines compared to untreated controls (difference=control–treatment).
Figure 31A:
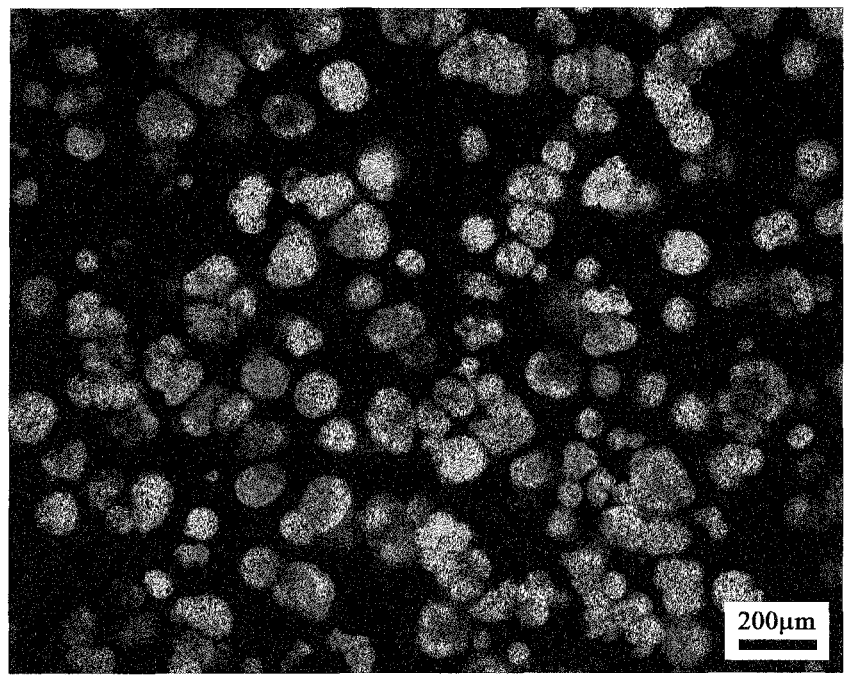
FIGS. 31A-31F show the 3-D morphology of Caco-2 and SK-OV-3 cells grown in Carbylan™-GSX in normal drug-free medium (A and D) and in the presence of LY294002 (B and E) and Paclitaxel (C and F) after stained with FDA (living cells, green) and PI (dead cells, red), Scale bar: 200 μm.
Figure 31B:
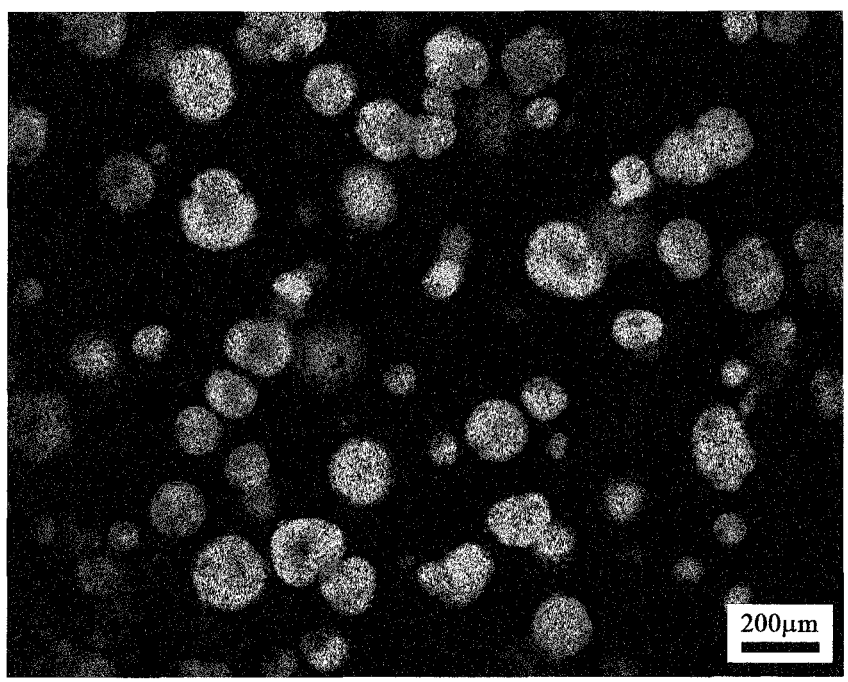
Figure 31C:
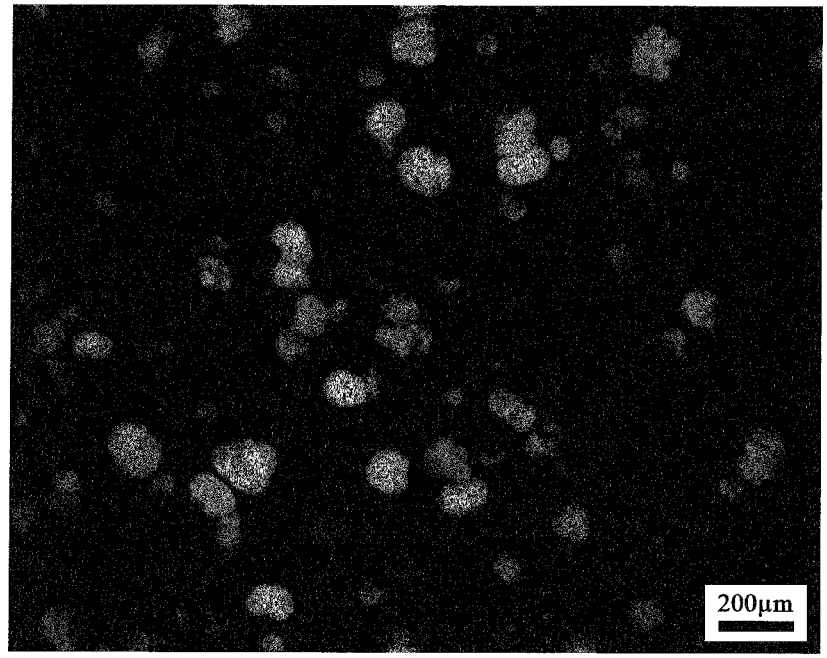
Figure 31D:
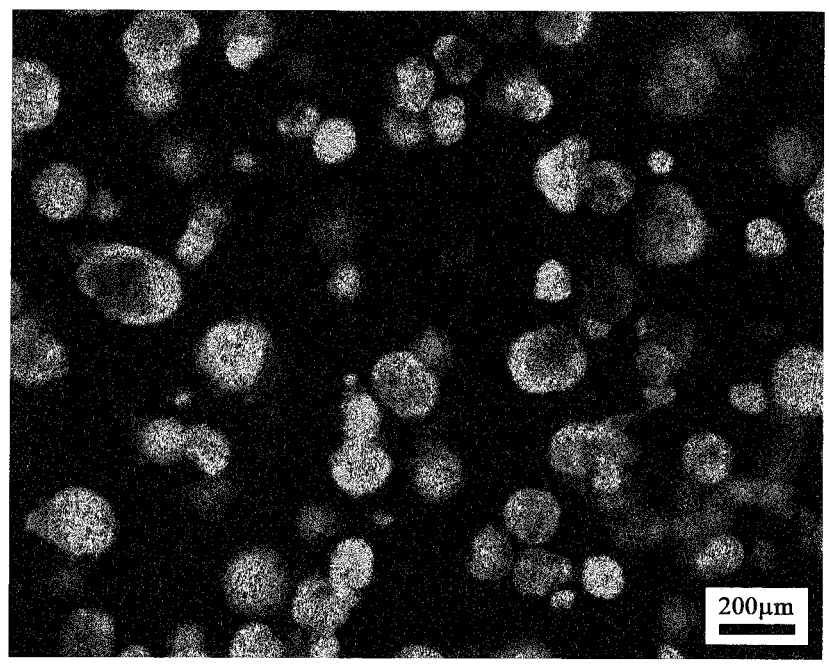
Figure 31E:
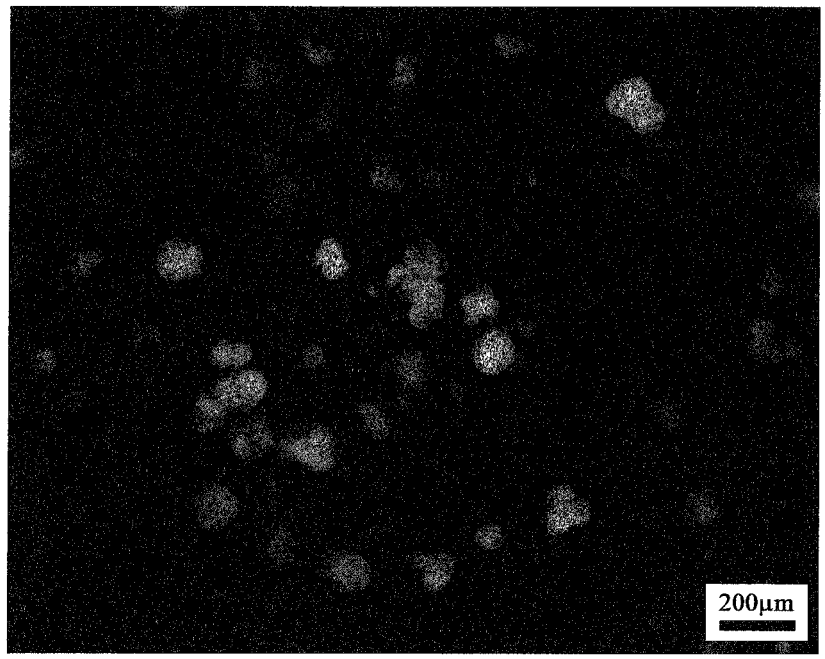
Figure 31F:
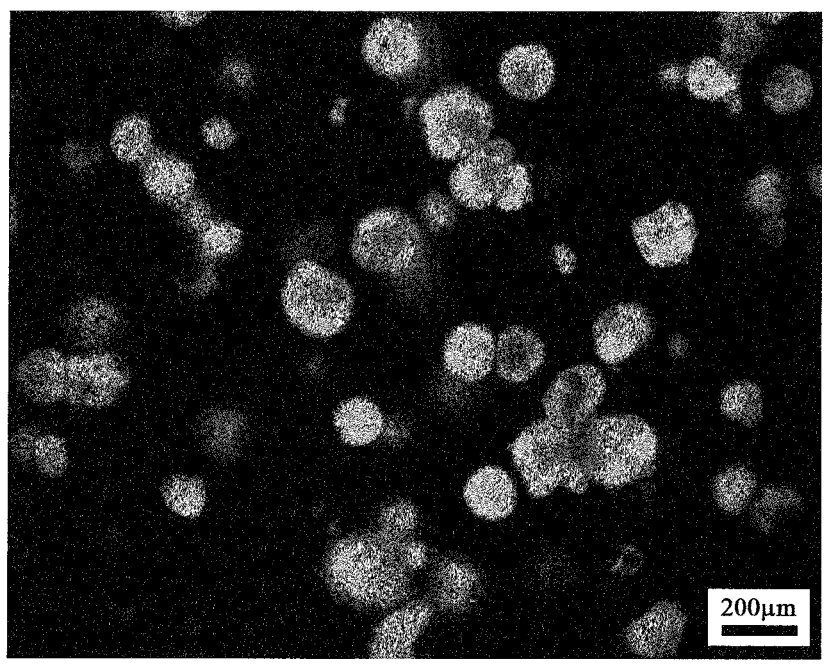

FIGS. 29A-F show the proliferation of different cell lines in the presence of LY294002 and paclitaxel. FIG. 30 replots the data to compare the differential responses of each cell line in normal medium to the same two drugs. In FIG. 30, for each pair of bars, a positive absorbance difference indicates that the drugs are cytotoxic, while a negatve value indicates that the drugs have little or no effect on the cells treated at the doses employed. The proliferation of MDA-MB-468, CaCo-2, HCT116, and FICA7 cell lines was inhibited by LY294002 and paclitaxel, in which MDA-MB-468 revealed the greatest response to LY294002 and paclitaxel. It also demonstrated that the anti-tubulin drug paclitaxel exhibited somewhat stronger inhibition effects than the PI 3-K inhibitor LY294002. Neither LY294002 and paclitaxel showed any inhibition effects on MDA-MB-231 and SK-OV-3 cell lines at the doses employed. FIGS. 31A-F show the 3-D morphology of Caco-2 and SK-OV-3 in normal medium (A and D) and in the presence of LY294002 (B and E) and Paclitaxel (C and F) after stained with FDA (living cells, green) and PI (dead cells, red) (scale bar is 200 μm). FDA/PI staining revealed that Caco-2 cell density in sECM hydrogels decreased in the presence of LY294002 and paclitaxel compared to the cells cultured in normal medium. Dead cells (in red color) and living cell debris were also observed in LY294002 and paclitaxel treated samples (FIGS. 31A, 31B, and 31C). In contrast, no obvious difference was observed in SK-OV-3 cells when cultured in normal medium or in the presence of LY294002 and paclitaxel (FIGS. 31D, 31E, and 31F).

9. The Isolation and Culture of Hepatocyte in 3-D Carbylan™-GSX Hydrogels and in 2-D Polystyrene Plate a. The Isolation of Hepatocytes The rat was anesthetized with chloral hydrate (360 mg/kg) by i.p. injection. The abdomen of the rat was shaved and washed with 70% ethanol. The abdominal cavity was then opened, the intestines were gently moved to the right, the portal vein was dissected, and a suture (4/0) was placed around the portal vein and tied. Next, another 4/0 suture was placed around the portal vein above the tie, a small incision on the portal vein was made, a PE tube was inserted into the portal vein, and the suture was tied. Next, the lower abdominal vena cava was dissected, and a hemostat was placed around the vein. The diaphragm was cut to expose inferior vena cava, and the vein was cut.

The liver was then perfused with Hanks' solution for 4 min (40 ml/min, total about 160 ml), and then perfused with enzyme solution for about 10 min (20 ml/min, total about 200 ml). The liver was excised from the body and transferred to a petri dish (100 mm) containing 15 ml of collagenase perfusate. Excess tissue and debris was then trimmed from the liver. The gall bladder can be removed carefully to prevent the leakage of bile.

Hepatocytes were stripped from the connective tissue stroma with a stainless steel dog comb in fresh, room temperature collagenase, and the residual white fibrous tissue was discarded. The cells were separated by repeated pipetting (10 times) with wide-mouth pipette. An equal volume of L15 medium supplemented with 1% calf serum can be added to the cell suspension. The cells were passed through a cell strainer (70 μm) into a 50 ml centrifuge tube, and the tube was centrifuged at 50×g for 5 min at 10° C. The cells were resuspended in modified L15 medium containing 10% heat inactivated fetal bovine serum, and gentamicin (50 ug/ml). The viable cells were counted after incubating the cells in 0.4% trypan blue for 5 min and the total number of cells was calculated.

b. The Culturing of Hepatocytes

Figure 33:
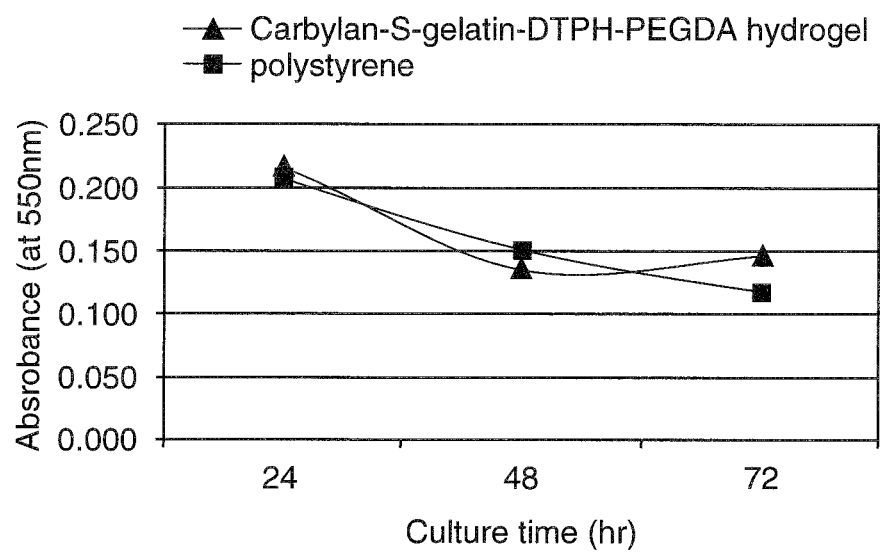
FIG. 33 shows the proliferation of hepatocytes on a 2D-polystyrene plate and 3-D Carbylan™-GSX as evaluated by MTS.

The cells were cultured in 2-D or 3-D. Two media were tested for hepatocyte culture: Leibovitz modified medium (L15) and Williams' medium E (MWE). L15 was good for the hepatocyte culture. Moreover, collagen coating to polystyrene plate was useful for hepatocyte attachment. FIG. 32 shows a hepatocyte culture on a polystyrene plate in L15 medium. The pictures on the left were taken in transmission light. The pictures on the right were taken after double fluorescence staining (FDA/PI staining). FIG. 33 shows that the proliferation of hepatocytes on 3D Carbylan™-GSX was similar to that of the 2-D polystyrene plate when evaluated by MTS. The cell morphology of hepatocytes on the 3D-Carbylan™-GSX was also similar to that of the 2-D polystyrene plate after cultured for three days (FIG. 34, double staining with FDA/PI).

III. Synthesis of Aminooxy Derivatives of Hyaluronan

1. Synthesis of Unsubstituted Aminooxy Derivatives

For this study three different Pluronic were chosen: F88 ($PEO_{103}$-$PPO_{39}$-$PEO_{103}$) (1a), F108 $PEO_{132}PO_{50}EO_{132}$) (1b), and F127 ($PEO_{100}$-$PPO_{65}$-$PEO_{100}$) (1c), characterized by different PPO/PEO ratio and molecular weight, respectively: 11,400, 14,600 and 12,600 kDa. A reaction scheme for producing the aminooxy derivatives is shown in FIG. 35.

The bis-aminooxy derivative of Pluronic F88 (1a) was synthesized under Mitsunobu reaction's conditions, (Ishikawa, T., Kawakami, M., Fukui, M., Yamashita, A., Urano, J., Saito, S. *J. MA. Chem. Soc.* 2001, 123, 7734-7735) in the presence of large excess triphenylphosphine ($Ph_3P$), N-hydroxyphtalimide and diethyl azodicarboxylate (DEAD). The crude product (2a) was precipitated from the reaction mixture with petroleum ether and re-crystallized four times using two solvent systems: THF/diethyl ether and THF/petroleum ether. The pure product was analyzed by $^1H$ NMR 400 MHz in $CDCl_3$. The choice of the solvent was made to obtain completely resolved terminal methylene peaks of bis-phtalimide derivative. The terminal methylene peak-triplet (δ 4.33 ppm, 4H, J=4.4), was identified and integrated against the multiple signal of phtalimide aromatic rings (δ 7.81-7.73 ppm, 8H), which confirmed, that received Pluronic derivative 2a was double protected by phtalimide. Next, deprotection reaction of phtalimide with hydrazine monohydrate in methylene chloride gave, after crystallization, bis-aminooxy Pluronic 3a, with good overall yield. All three Pluronics F88, F108 and F127 were converted into bis-AO derivatives using the same general method. Presented synthetic pathway allows producing that kind of derivatives in good yields, basing on simple chemical transformations and purification methods.

Experimental Section

General Methods. Chemicals were obtained from Aldrich, Acros and BASF and were used without further purification. Solvents were reagent-grade and distilled before use: THF was distilled from sodium wire, and $CH_2Cl_2$ was distilled from $CaH_2$. Reactions requiring anhydrous conditions were carried out in oven-dried glassware (2 h, 120° C.) under inert atmosphere (Ar) unless otherwise indicated. Concentration in vacuo refers to the use of rotary evaporator for solvent removal; NMR spectra were recorded at 400 MHz ($^1H$) and 101 MHz ($^{13}C$) at ambient temperature. Chemical shifts are reported relative to those of internal chloroform ($δ_H$ 7.24), for $^1H$; chloroform ($δ_C$ 77.0) for $^{13}C$.

Pluronic F88 bis-O-phtalimide derivative (2a). To a stirred solution of Pluronic F88 (13.98 g, 1.16 mmol) and $Ph_3P$ (6.1 g, 23.3 mmol), N-hydroxyphtalimide (3.78 g, 23.2 mmol) in THF (75 ml) was added DEAD (3.5 ml, 23.2 mmol) at 10° C. The reaction was stirred overnight at room temperature and finished by precipitation of the product with petroleum ether. The crude 2a was re-crystallized four times using two solvent systems: THF/petroleum ether and THF/diethyl ether (two times for each system). The pure product 2a was obtained in form of white loose solid (12.28 g, 86%). $^1H$ NMR (400 MHz, $CDCl_3$) δ 7.80-7.78 (4H, m), 7.72-7.69 (4H, m), 4.32 (t, 4H, J=4.4 Hz), 3.83-3.68 (m, 9H), 3.60-3.27 (m, 1052H), 2.21 (s, 9H), 1.10-1.08 (m, 123H). $^{13}C$ NMR (101 MHz, $CDCl_3$) δ 134.2, 123.2, 75.2, 75.0, 74.8, 73.1, 72.6, 70.26, 33.2, 17.2, 17.1

Pluronic F88 bis-aminooxy derivative (3a). Hydrazine monohydrate (0.71 ml) was added to a stirred solution of 2a (12.38 g) in $CH_2Cl_2$ (50 ml) at 0° C. It was stirred for 1.5 h at room temperature and precipitate was filtered off. After concentration the residue was dissolved in THF and precipitated using diethyl ether. Re-crystallization using THF/petroleum ether led to obtain pure compound 3a as a white loose solid (11 g, 90%). $^1H$ NMR (400 MHz, $CDCl_3$) δ 3.81-3.78 (m, 8H), 3.71-3.30 (m, 874H), 2.02 (s, 10H), 1.24-0.98 (m, 100H); $^{13}C$ NMR (101 MHz, $CDCl_3$) δ 75.5, 75.3, 75.2, 73.3, 72.9, 70.5, 33.3, 17.4, 17.3.

2. Synthesis of Substituted Aminooxy Derivatives

Low molecular weight HA (190 KDa) (0.458 g, 1.145 mmol) was dissolved in 46 ml distilled water. Then, 0.5 g O-phenylhydroxylamine hydrochloride (OPH) (3.434 mmol) was added, and the solution pH was adjusted to 4.75 by adding 1.0 N HCl. Next, 0.11 g EDCI (0.057 mmol) was added under magnetic stirring, and the solution pH was maintained at 4.75 for 4 h by adding 0.1 N HCl. The solution was dialyzed extensively against 100 mM NaCl, followed by dialysis against distilled water. After that the solution was filtered to remove extraneous solids and lyophilized to give the HA-OPH product as a white powder.

Figure 36:
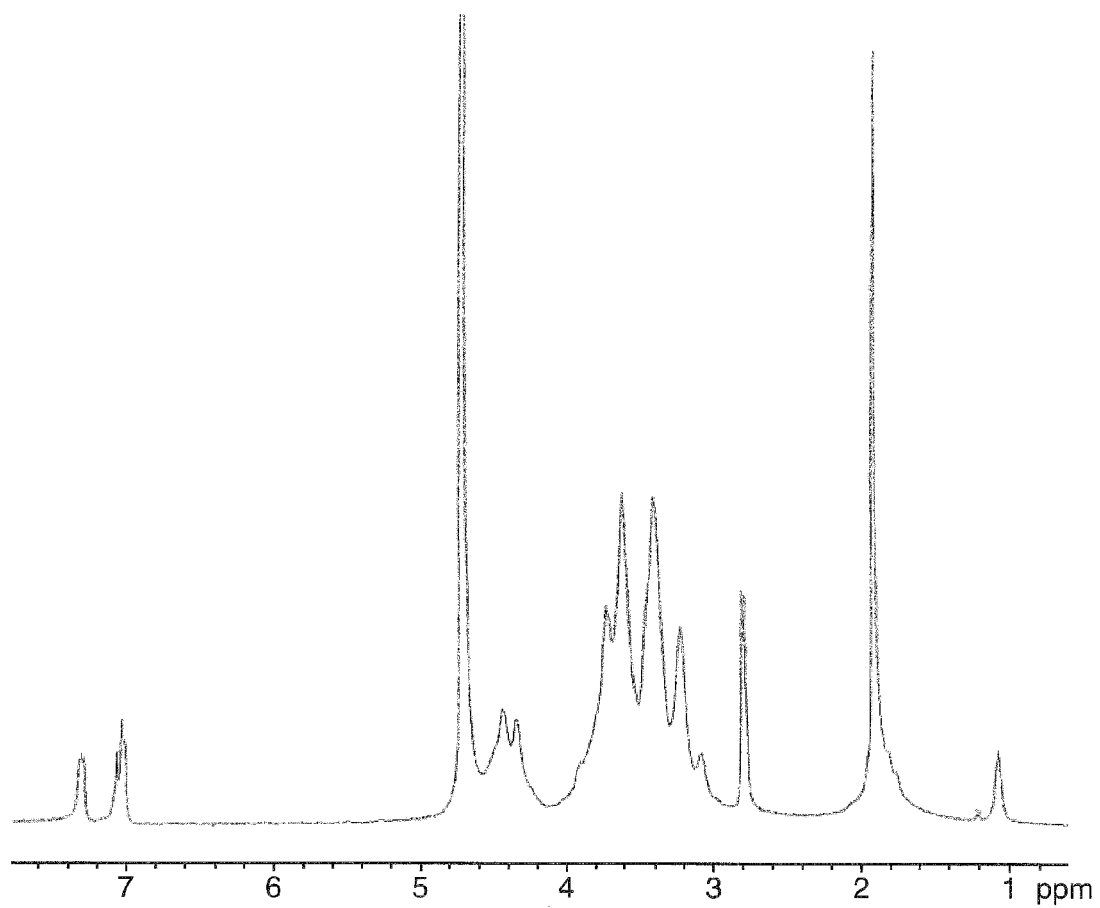
FIG. 36 is the $^1$H NMR spectrum of HA-aminooxy ether.

The peaks at δ 7.30 (2 protons) and 7.05 (3 protons) (FIG. 36) were from the phenyl group, and the degree of substitution was found to be ca. 21% based on integration of the proton NMR resonances. Expected resonances for N-acetylurea-modified hyaluronan were detected at δ 1.10 and δ 2.78.

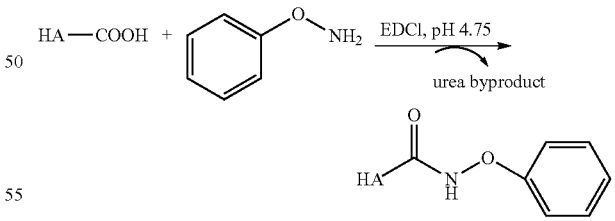

3. Coupling of an Aminooxy-Derivatized Polymer with Hyaluronan

An experiment was designed to test whether an aminooxy (AO) derivative of Pluronic F108 could be employed for covalent coupling with resulting surface immobilization of HA. Pluronic F108 is commonly used to coat plastic surfaces via hydrophobic adsorption of the PPO block of the PEO-PPO-PEO triblock, rendering the surface resistant to protein adsorption. In addition, amine-reactive Pluronic derivatives are commercially available from allvivo, inc., and can be used to immobilize specific growth factors and proteins on surfaces. In this experiment, it was demonstrated that a fluorescent derivative of HA, fluorescein-HA, can be covalently attached to a surface-adsorbed bis-aminooxy derivatized pluronic.

Materials and Methods

F108-BisAO was dissolved in distilled water to give 0.5% (w/v) solution. Then 0.1 ml solution was added into each well of 96-well plate. After 12 h, the plate was washed 5 times with distilled water. Then 0.1 ml EDCI (10 mg/ml in 0.1 N MOPS) (pH 4.7) was added into each well, and then 0.1 ml fluorescein-HA (MW 150 kDa) (2 mg/ml in 0.1 N MOPS) (pH 4.7) was added. (Note: fluorescein—HA was separately prepared using fluorescein hydrazide (Molecular Probes, Inc.), EDCI, 150 kDa HA, at pH 4.75 following standard hydrazide coupling protocols.) This surface reaction was allowed to proceed for 3 days in the dark. Next, the plate was washed 5× with DPBS, and the fluorescence was measured in a fluorescence plate reader using $\lambda_{ex}$=496 nm and $\lambda_{em}$=520 nm.

Results

Figure 39:
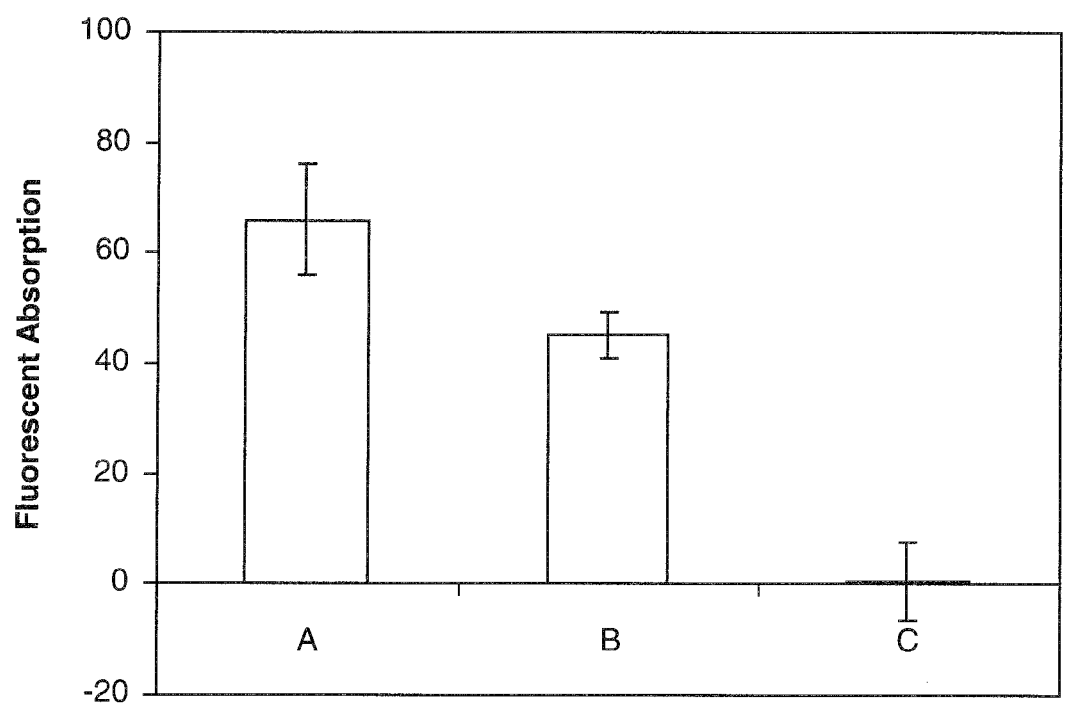
FIG. 39 shows the fluorescence of immobilized fluorescein-HA with (A) a bis-aminooxy derivatized pluronic, (B) a bis-aminooxy derivatized pluronic and EDCI, and (C) no bis-aminooxy derivatized pluronic.

FIG. 39 shows the fluorescence of immobilized fluorescein-HA with (A) a bis-aminooxy derivatized pluronic, (B) a bis-aminooxy derivatized pluronic and EDCI, and (C) no bis-aminooxy derivatized pluronic. The fluorescent absorption of experimental group (A) was significantly higher than the control groups (B, no EDCI, and C, no Pluronic). This result indicated that F-108 BisAO was adsorbed to the 96-well plate through hydrophobic interactions, and that EDCI-mediated coupling of fluorescein-HA via the F-108 BisAO aminooxy to HA carboxylate condensation was achieved on the plate surface. The high absorption in control group B may result from the hydrophobic and charge interactions of fluorescein-HA to F-108 BisAO on the surface.

4. Self-Assembling Hyaluronan Hydrogels Formation with Monofunctional Pluronic-AO The hypothesis that the attachment of a Pluronic to HA would result in a self-assembling hydrogel based on the intermolecular and intramolecular hydrophobic interactions of multiple PEO-PPO-PEO triblock polymers attached to HA was tested. The experiment also tested the feasibility of using the aminooxy condensation as a new chemistry for chemical modification of HA carboxylate groups with aminooxy-containing polymers in solution as claimed and validated for small molecule aminooxy compounds.

Materials and Methods

A 50-mg sample of HA (830 kDa) was dissolved in 20 ml of distilled water to give 0.5% (w/v) solution, and then 1.5 g of the monomethoxy, monoaminooxy-Pluronic F88 derivative, MeO-F88-AO, was added. Next, the solution pH was adjusted to ca. 4.7, and 50 mg of EDCI was added. After 15 min, a gel formed. After 2 h, the gel was put in dialysis tubing (MW cut-off 50,000), and dialysis against 0.1 N NaCl solution was allowed to proceed for 3 days, followed by dialysis against water for one day. The gel is only 0.3% HA w/v at present and is a gel at both room temperature and 4° C.

Results

Neither Pluronic F88 nor the chemically-synthesized MeO-F88-AO formed gels at 20° C. or 4° C. at concentrations up to 5 mg/ml. In contrast, the covalent coupling of MeO-F88-AO to make HA through carbodiimide-mediated coupling of the HA carboxylates to the aminooxy groups of one or more MeO-F88-AO molecules led to the formation of a physical gel. Not wishing to be bound by theory, the driving force for formation of this physically crosslinked gel is consistent with the proposed hydrophobic interaction of the multiple PPO blocks present in the covalently-modified macromolecules. Both intermolecular and intramolecular hydrophobic interactions may contribute to this gelation effect. The loose physical gel has significant potential as a novel hyperviscous, slowly degraded HA material for use in adhesion prevention, injection as a dermal filler, incorporation in topical cosmetics or drug delivery formulations, injection for reduction of pain and inflammation in osteoarthritis, for ophthalmic surgery, for soft tissue bulking in plastic surgery, for injection into the vocal folds for prophylaxis or treatment of dysphonias, and other clinical applications.

5. Conjugation of Heparin with Bis-Aminooxy Derivatized Pluronic

Materials and Methods

BisA0-F108 in water (5 mg/ml) was loaded at 0.1 ml per well and incubated for overnight on 96-well plate. The wells were washed with distilled water (5×) and then 0.1 ml per well of a solution of EDCI (10 mg/ml) in MOPS (0.1 N, pH 4.7) was added, followed by 0.1 ml per well of heparin sodium salt (average Mw 15 kD, in 1:2 serial dilutions from 4 mg/ml to 0.25 mg/ml) in MOPS (0.1N, pH 4.7). The heterogeneous reaction allowed to proceed for 3 days at room temperature. The plate was washed 5× with Tris-HCl buffer (TBS, 20 mM, pH 7.5), and blocked with StabilGuard solution (Surmodics) at 200 µl/well for 1 hr.

The immobilized heparin on plate was examined with using an ELISA based on a published method (S. Cai, J. L. Dufner-Beattie, and G. D. Prestwich, "A Selective Protein Sensor for Heparin Detection," *Analyt. Biochem.*, 326, 33-41 (2004)). Briefly, after the plate was blocked and washed 3× with, a heparin binding protein GST-HB3 (100 µg/ml) was added at 100 µl/well. The plate was incubated for 1 hr and washed again with TBS, followed by addition with 1:1000 anti-GST (Sigma) in TBS at 100 µl/well and incubation for 1 hr. Next, 1:3000 anti-mouse IgG-HRP conjugate (Sigma) in TBS of 100 µl/well was added and incubated for another 1 hr. Finally, the substrate 3,3',5,5'-tetramethylbenzidine (TMB, Sigma) as added at 100 µl/well was added and the reaction was quenched with 1 M $H_2SO_4$ as the color appearance became stable. The plate was read at 450 nm and the absorbance was corrected by subtracting the blank wells loaded with GST-HB3 followed by the same ELISA procedure (background reading).

Results

Figure 40:
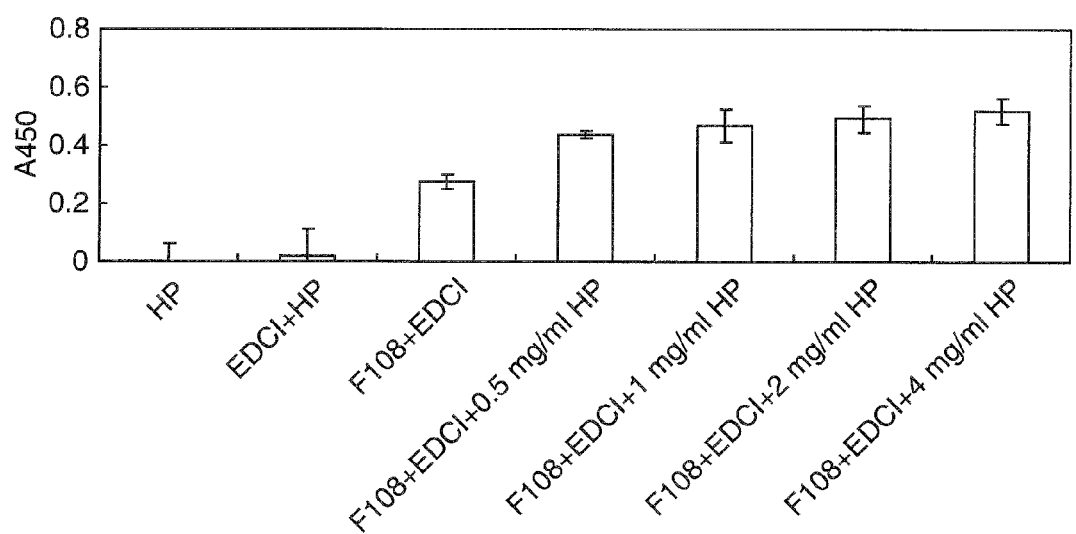
FIG. 40 shows ELISA results for surface immobilization of heparin with bisAO-pluronic.

FIG. 40 shows clearly that neither heparin alone nor heparin plus EDCI result in surface immobilization of heparin. (Note: for these two groups—HP and EDCI+HP—the heparin concentration tested was 2 mg/ml). The use of the EDC1 and F108 alone, however, creates a surface that appears to show some nonspecific binding to the ELISA reagents in this preliminary test. A similar effect was observed from the combined hydrophobic and charge interactions of fluorescein-HA to F108-bisAO on the surface.

Nonetheless, the conjugation and absorption of heparin in this proof of concept experiment shows a trend toward heparin dose-dependency, despite the fact that the GST-HB3 protein detection is at maximal binding capacity and the top of its dynamic range. In our experience, changing wash conditions and adjusting immobilization amounts and detection reagent amounts can produce a lower background, improve sensitivity, and yield a quantitative assay based on this method.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A modified-glycosaminoglycan comprising from 0.1% to 30% of its primary hydroxyl groups chemically substituted with -L-$CO_2$H, or a salt or ester thereof, where L is a polyalkylene group having the formula —$(CH_2)_n$—, and n is an integer in a range from 1-10, wherein when the glycosaminoglycan is hyaluronan, the primary hydroxyl groups are primary 0-6 hydroxyl groups of an N-acetyl-glucosamine residue, and when the glycosaminoglycan is other than hyaluronan, the primary hydroxyl groups are C-6 hydroxyl groups of a non-uronic acid sugar component of a repeating disaccharide subunit.

2. The modified-glycosaminoglycan of claim 1, wherein the glycosaminoglycan is selected from the group consisting of chondroitin, chondroitin sulfate, dermatan, dermatan sulfate, heparin, heparan sulfate, and hyaluronan.

3. The modified-glycosaminoglycan of claim 1, wherein the glycosaminoglycan is a hyaluronan.

4. The modified-glycosaminoglycan of claim 3, wherein L is —$CH_2$—.

5. The modified-glycosaminoglycan of claim 3, further comprising at least one secondary hydroxyl group of the hyaluronan substituted with -L$CO_2$H, or a salt or ester thereof.

6. The modified-glycosaminoglycan of claim 1, wherein the glycosaminoglycan is selected from the group consisting of chondroitin, chondroitin sulfate, dermatan, dermatan sulfate, heparin, and heparan sulfate.

7. The modified-glycosaminoglycan of claim 1, wherein L is —$CH_2$—.

8. The modified-glycosaminoglycan of claim 1, wherein the glycosaminoglycan is hyaluronan and from 0.1%, 0.5%, 1%, 2%, 3%, 5%, 10%, 15%, 20%, 25%, to 30%, of the primary hydroxyl groups of hyaluronan are chemically substituted, where any lower endpoint can be combined with any upper endpoint.

* * * * *

UNITED STATES PATENT AND TRADEMARK OFFICE
CERTIFICATE OF CORRECTION

| | | |
|---|---|---|
| PATENT NO. | : 8,691,793 B2 | Page 1 of 1 |
| APPLICATION NO. | : 13/184401 | |
| DATED | : April 8, 2014 | |
| INVENTOR(S) | : Prestwich et al. | |

It is certified that error appears in the above-identified patent and that said Letters Patent is hereby corrected as shown below:

In the Claims

Column 71, line 8, Claim 1.: change "...primary 0-6 hydroxyl groups of an N-acetyl-glucosamine..." to --primary C-6 hydroxyl groups of an N-acetyl-glucosamine--

Signed and Sealed this
Fourteenth Day of October, 2014

Michelle K. Lee
*Deputy Director of the United States Patent and Trademark Office*